(12) United States Patent
Lundberg et al.

(10) Patent No.: US 9,334,487 B2
(45) Date of Patent: May 10, 2016

(54) METHODS FOR DIAGNOSING RHEUMATOID ARTHRITIS

(71) Applicant: Imperial Innovations Limited, London (GB)

(72) Inventors: Karin Lundberg, London (GB);
Patrick Venables, London (GB);
Andrew Kinloch, London (GB)

(73) Assignee: IMPERIAL INNOVATIONS LIMITED, London (GB)

(*) Notice: Subject to any disclaimer, the term of this patent is extended or adjusted under 35 U.S.C. 154(b) by 0 days.

(21) Appl. No.: 13/657,612

(22) Filed: Oct. 22, 2012

(65) Prior Publication Data

US 2013/0078654 A1 Mar. 28, 2013

Related U.S. Application Data

(63) Continuation of application No. 12/524,465, filed as application No. PCT/GB2008/000267 on Jan. 25, 2008.

(30) Foreign Application Priority Data

Jan. 25, 2007 (GB) .................................. 0701417.8
Nov. 9, 2007 (GB) .................................. 0722035.3

(51) Int. Cl.
*C12N 9/88* (2006.01)

(52) U.S. Cl.
CPC ........................................ *C12N 9/88* (2013.01)

(58) Field of Classification Search
None
See application file for complete search history.

(56) References Cited

FOREIGN PATENT DOCUMENTS

| EP | 1456662 B1 | 6/2006 |
|---|---|---|
| WO | 0146222 A2 | 6/2001 |
| WO | 03050542 A2 | 6/2003 |
| WO | 2006048556 A1 | 5/2006 |

OTHER PUBLICATIONS

Pedersen, M., et al., "Environmental risk factors differ between rheumatoid arthritis with and without auto-antibodies against cyclic citrullinated peptides", "Arthritis Research & Therapy", Jul. 27, 2006, p. R133, vol. 8, No. 4.
Perosa, F., et al., "Generation of biologically active linear and cyclic peptides has revealed a unique fine specificity of rituximab and its possible cross-reactivity with acid sphingomyelinase-like phosphodiesterase 3b precursor", "Blood", Oct. 13, 2005, pp. 1070-1077, vol. 107.
Petkova, S., et al., "Human antibodies induce arthritis in mice deficient in the low-affinity inhibitory IgG receptor Fc gamma RIIB", "J Exp Med", Feb. 13, 2006, pp. 275-280, vol. 203, No. 2.
Pratesi, F., et al., "Autoantibodies specific for alpha-enolase in systemic autoimmune disorders", "Journal of Rheumatology", 2000, pp. 109-115, vol. 27.
Rantapaeae-Dahlqvist, S., et al., "Antibodies against cyclic citrullinated peptide and IgA rheumatoid factor predict the development of rheumatoid arthritis", "Arthritis & Rheumatism", Oct. 2003, pp. 2741-2749, vol. 48, No. 10.
Ren, G., et al., "Cellular targets of anti-alpha-enolase autoantibodies of patients with autoimmune retinopathy", "Journal of Autoimmunity", 2004, pp. 161-167, vol. 23.
Roozendaal, C., et al., "Catalase and alpha-enolase: two novel granulocyte autoantigens in inflammatory bowel disease (IBD)", "Clin Exp Immunol", 1998, pp. 10-16, vol. 112.
Rosenstein, E., et al., "Hypothesis: the humoral immune response to oral bacteria provides a stimulus for the development of rheumatoid arthritis", "Inflammation", Dec. 2004, pp. 311-318, vol. 28, No. 6.
Saal, J., et al., "Persistence of B19 parvovirus in synovial membranes of patients with rheumatoid arthritis", "Rheumatol Int", 1992, pp. 147-151, vol. 12.
Saraux, A., et al., "Value of antibodies to citrulline-containing peptides for diagnosing early rheumatoid arthritis", "J Rheumatol", 2003, pp. 2535-2539, vol. 30.
Saulot, V., et al., "Presence of Autoantibodies to the Glycolytic Enzyme alpha-enolase in Sera From Patients With Early Rheumatoid Arthritis", "Arthritis & Rheumatism", May 2002, pp. 1196-1201, vol. 46, No. 5.
Schellekens, G., et al., "Citrulline is an essential constituent of antigenic determinants recognized by rheumatoid arthritis-specific autoantibodies", "J Clin Invest", Jan. 1998, pp. 273-281, vol. 101, No. 1.
Schellekens, G., et al., "The diagnostic properties of rheumatoid arthritis antibodies recognizing a cyclic citrullinated peptide", "Arthritis & Rheumatology", Jan. 2000, pp. 155-163, vol. 43, No. 1.
Sebbag, M., et al., "The Antiperinuclear Factor and the So-called Antikeratin Antibodies Are the Same Rheumatoid Arthritis-Specific Autoantibodies", "J Clin Invest", Jun. 1995, pp. 2672-2679, vol. 95.
Silman, A., et al., "Epidemiology and genetics of rheumatoid arthritis", "Arthritis Res", May 9, 2002, pp. 5265-5272, vol. 4, Supplement 3.
Symmons, D., et al., "The world of biologics", "Lupus", Mar. 2006, pp. 122-126, vol. 15, No. 3.
Takahashi, Y., et al., "Human parvovirus B19 as a causative agent for rheumatoid arthritis", "Proc Natl Acad Sci", Jul. 1998, pp. 8227-8232, vol. 95.
Tamai, M., et al., "The presence of anti-cyclic citrullinated peptide antibody is associated with magnetic resonance imaging detection of bone marrow oedema in early stage rheumatoid arthritis", "Ann Rheum Dis", Jan. 2006, pp. 133-134, vol. 65, No. 1.

(Continued)

*Primary Examiner* — Gerald R Ewoldt
(74) *Attorney, Agent, or Firm* — Oblon, McClelland, Maier & Neustadt, L.L.P.

(57) ABSTRACT

The present invention relates to methods of diagnosing, prognosing, preventing or delaying onset of or treating rheumatoid arthritis, methods of distinguishing between different types or stages of rheumatoid arthritis, of identifying an individual at risk of developing rheumatoid arthritis, and of monitoring efficacy of a treatment regime in an individual being treated for rheumatoid arthritis, using a citrullinated enolase peptide to detect or capture antibodies associated with rheumatoid arthritis.

14 Claims, 17 Drawing Sheets

(56) References Cited

OTHER PUBLICATIONS

Tanaka, S., et al., "Anti-alpha-enolase Antibodies in Pituitary Disease", "Endocrine Journal", 2003, pp. 697-702, vol. 50, No. 6.
Terrier, B., et al., "Alpha-enolase: A target of antibodies in infectious and autoimmune diseases", "Autoimmunity Reviews", Dec. 1, 2006, pp. 176-182, vol. 6.
Thompson, J., et al., "Clustal W: improving the sensitivity of progressive multiple sequence alignment through sequence weighting, position-specific gap penalties and weight matrix choice", "Nucleic Acids Research", 1994, pp. 4673-4680, vol. 22, No. 22.
Vallbracht, I., et al., "Diagnostic and clinical value of anti-cyclic citrullinated peptide antibodies compared with rheumatoid factor isotypes in rheumatoid arthritis", "Ann Rheum Dis", 2004, pp. 1079-1084, vol. 63.
Van Gaalen, F., et al., "Autoantibodies to Cyclic Citrullinated Peptides Predict Progression to Rheumatoid Arthritis in Patients With Undifferentiated Arthritis", "Arthritis & Rhemuatism", Mar. 2004, pp. 709-715, vol. 50, No. 3.
Van Gaalen, F., et al., "Association between HLA class II genes and autoantibodies to cyclic citrullinated peptides (CCPs) influences the severity of rheumatoid arthritis", "Arthritis & Rheumatism", Jul. 2004, pp. 2113-2121, vol. 50, No. 7.
Van Venrooij, W., et al., "Anticitrullinated protein/peptide antibody and its role in the diagnosis and prognosis of early rheumatoid arthritis", "Neth J Med", Nov. 2002, pp. 383-388, vol. 60, No. 10.
Van Der Helm-Van Mil, A., et al., "The HLA-DRB1 shared epitope alleles are primarily a risk factor for anti-cyclic citrullinated peptide antibodies and Are Not an Independent Risk Factor for Development of Rheumatoid Arthritis", "Arthritis & Rheumatism", Apr. 2006, pp. 1117-1121, vol. 54, No. 4.
Venables, P., et al., "Quantitation and Detection of Isotypes of Anti-SS-B Antibodies by ELISA and FARR Assays Using Affinity Purified Antigens", "Arthritis & Rheumatism", Feb. 1983, pp. 146-155, vol. 26, No. 2.
Vencovsky, J., et al., "Autoantibodies can be prognostic markers of an erosive disease in early rheumatoid arthritis", "Ann Rheum Dis", 2003, pp. 427-430, vol. 62.
Vossenaar, E., et al., "Citrullination of Synovial Proteins in Murine Models of Rheumatoid Arthritis", "Arthritis & Rheumatism", Sep. 2003, pp. 2489-2500, vol. 48, No. 9.
Vossenaar, E., et al., "Rheumatoid arthritis specific anti-Sa antibodies target citrullinated vimentin", "Arthritis Research & Therapy", Feb. 5, 2004, pp. R142-R150, vol. 6, No. 2.
Vossenaar, E., et al., "Expression and activity of citrullinating peptidylarginine deiminase enzymes in monocytes and macrophages", "Ann Rheum Dis", 2004, pp. 373-381, vol. 63.
Vossenaar, E., et al., "The presence of citrullinated proteins is not specific for rheumatoid synovial tissue", "Arthritis & Rheumatism", 2004, pp. 3485-3494, vol. 50, No. 11.
Vossenaar, E., et al., "Anti-CCP antibodies, a highly specific marker for (early) rheumatoid arthritis", "Clin Applied Immunol Rev", 2004, pp. 239-262, vol. 4.
Wakui, H., et al., "Circulating antibodies against alpha-enolase in patients with primary membranous nephropathy (MN)", "Clin Exp Immunol", 1999, pp. 445-450, vol. 118.
Young, B., et al., "Anti-keratin antibodies in rheumatoid arthritis", "British Medical Journal", 1979, pp. 97-99, vol. 2.
Nijenhuis, S., et al., "Autoantibodies to citrullinated proteins in rheumatoid arthritis clinical performance and biochemical aspects of an RA-specific marker", "Clinica Chemica Acta", 2004, pp. 17-34, vol. 350.
Pancholi, V., "Multifunctional alpha-enolase: its role in diseases", "Cell Mol Life Sci", 2001, pp. 902-920, vol. 58.
Albert, L., et al., "Molecular mimicry and autoimmunity", "N. Engl. Journal of Medicine", Dec. 30, 1999, pp. 2068-2074, vol. 341, No. 27.
Anzilotti, C., et al., "Antibodies to Viral Citrullinated Peptide in Rheumatoid Arthritis", "J. Rheumatology", Mar. 1, 2006, pp. 647-651, vol. 33, No. 4.

Arnett, F., et al., "The American Rheumatism Association 1987 revised criteria for the classification of rheumatoid arthritis", "Arthritis and Rheumatism", Mar. 1988, pp. 315-324, vol. 31, No. 3.
Balandraud, N., et al., "Epstein-Barr Virus and Rheumatoid Arthritis", "Automimmunity Reviews", Apr. 9, 2004, pp. 362-367, vol. 3.
Blaschke, S., et al., "Epstein-Barr virus infection in peripheral blood mononuclear cells, synovial fluid cells, and synovial membranes of patients with rheumatoid arthritis", "Journal of Rheumatology", 2000, pp. 866-873, vol. 27, No. 4.
Burkhardt, H., et al., "Humoral immune response to citrullinated collagen type II determinants in early rheumatoid arthritis", "Eur J Immunol", 2005, pp. 1643-1652, vol. 35.
Cantaert, T., et al., "Citrullinated Proteins in Rheumatoid Arthritis", "Arthritis & Rheumatism", Nov. 2006, pp. 3381-3389, vol. 54, No. 11.
Carty, S., et al., "Should Infection Still be Considered as the Most Likely Triggering Factor for Rheumatoid Arthritis?", "Annal Rhem Dis", 2004, pp. 1146-1149, vol. 63, Supplement II.
Despres, N., et al., "The SA System: A Novel Antigen-Antibody System Specific for Rheumatoid Arthritis", "J Rheumatology", 1994, pp. 1027-1033, vol. 21, No. 6.
Eming, R., et al., "Immunoadsorption in pemphigus", "Autoimmunity", Nov. 1, 2006, pp. 609-616, vol. 39, No. 7.
Ioan-Facsinay, A., et al., "Marked Differences in Fine Specificity and Isotype Usage of the Anti-Citrullinated Protein Antibody in Health and Disease", "Arthritis & Rheumatism", Oct. 2008, pp. 3000-3008, vol. 58, No. 10.
Forslind, K., et al., "Prediction of radiological outcome in early rheumatoid arthritis in clinical practice: role of antibodies tocitrullinated peptides (anti-CCP)", "Ann Rheum Disease", 2004, pp. 1090-1095, vol. 63.
Fujii, A., et al., "Autoantibodies against the amino terminal of alpha-enolase are a useful diagnostic marker of Hashimoto's encephalopathy", "Journal of Neuroimmunology", 2005, pp. 130-136, vol. 162.
Girbal-Neuhauser, E., et al., "The epitopes targeted by the rheumatoid arthritis-associated antifilaggrin autoantibodies are post-translationally generated on various sites of (pro)filaggrin by deimination of arginine residues", "Journal of Immunology", 1999, pp. 585-594, vol. 162.
Havemose-Poulsen, A., et al., "Periodontal and hematological characteristics associated with aggressive periodontitis, juvenile idiopathic arthritis, and rheumatoid arthritis", "J Periodontol", Feb. 2006, pp. 280-288, vol. 77, No. 2.
Huizinga, T., et al., "Refining the Complex Rheumatoid Arthritis Phenotype Based on Specificity of the HLA—DRB1 Shared Epitope for Antibodies to Citrullinated Proteins", "Arthritis & Rheumatism", 2005, pp. 3433-3438, vol. 52, No. 11.
Euro-Diagnostica AB, "Immunoscan RA Anti-CCP Test Kit: A microtitre plate based enzyme immunoassay for detection of Rheumatoid Arthritis specific antibodies (anti-CCP)", "Catalogue No. RA-96RT", Nov. 2005, pp. 1-90, Published in: Sweden.
Ishigami, A., et al., "Abnormal Accumulation of Citrullinated Proteins Catalyzed by Peptidylarginine Deiminase in Hippocampal Extracts From PatientsWith Alzheimer's Disease", "Journal of Neuroscience Research", Feb. 9, 2005, pp. 120-128, vol. 80.
Jansen, L., et al., "The predictive value of anti-cyclic citrullinated peptide antibodies in early arthritis", "J Rheumatology", 2003, pp. 1691-1695, vol. 30.
Kastbom, A., et al., "Anti-CCP antibody test predicts the disease course during 3 years in early rheumatoid arthritis (the Swedish TIRA project)", "Ann Rheum Dis", 2004, pp. 1085-1089, vol. 63.
Katz, J., et al., "Human leukocyte antigen (HLA) DR4: Positive association with rapidly progressing periodontitis", "J Periodontol", Sep. 1987, pp. 607-610, vol. 58, No. 9.
Kinloch, A., et al., "Identification of citrullinated alpha-enolase as a candidate autoantigen in rheumatoid arthiritis", "Arthiritis Research & Therapy", Oct. 19, 2005, pp. R1421-R1429, vol. 7.
Kinloch, A., et al., "Pathogenic role of antibodies to citrullinated proteins in rheumatoid arthritis", "Expert Rev. Clin. Immunol.", May 2006, pp. 365-375, vol. 2, No. 3.

(56) References Cited

OTHER PUBLICATIONS

Klareskog, L., et al., "A new model for an etiology of rheumatoid arthritis: smoking may trigger HLA-DR (shared epitope)-restricted immune reactions to autoantigens modified by citrullination", "Arthritis & Rheumatism", Jan. 2006, pp. 38-46, vol. 54, No. 1.

Kroot, E., et al., "The prognostic value of anti-cyclic citrullinated peptide antibody in patients with recent-onset rheumatoid arthritis", "Arthritis & Rheumatism", Aug. 2000, pp. 1831-1835, vol. 43, No. 8.

Kuhn, K., et al., "Antibodies against citrullinated proteins enhance tissue injury in experimental autoimmune arthritis", "Journal of Clinical Investigation", Apr. 2006, pp. 961-973, vol. 116, No. 4.

Lee, K., et al., "Human alpha-enolase from endothelial cells as a target antigen of anti-endothelial cell antibody in Behcet's disease", "Arthritis & Rheumatism", Jul. 2003, pp. 2025-2035, vol. 48, No. 7.

Lu, G., et al., "Improved Synthesis of 4-Alkoxybenzyl Alcohol Resin", "J Org Chem", 1981, pp. 3433-3436, vol. 46.

Mageed, R., "The RF antigen", "Manual of Biological Markers of Disease", 1994, pp. 1-27, vol. B1.1, Publisher: Kluwer Academic Publishers, Published In: Netherlands.

Makrygiannakis, D., et al., "Citrullination is an inflammation-dependent process", "Ann Rheum Dis.", Mar. 15, 2006, pp. 1219-1222, vol. 65, No. 9.

Marotte, H., et al., "The association between periodontal disease and joint destruction in rheumatoid arthritis extends the link between the HLA-DR shared epitope and severity of bone destruction", "Ann Rheum Dis", Nov. 10, 2005, pp. 905-909, vol. 65.

Masson-Bessiere, C., et al., "In the rheumatoid pannus, anti-filaggrin autoantibodies are produced by local plasma cells and constitute a higher proportion of IgG than in synovial fluid and serum", "Clin Exp Immunol", 2000, pp. 544-552, vol. 119.

McGraw, W., et al., "Purification, Characterization, and Sequence Analysis of a Potential Virulence Factor from Porphyromonas gingivalis, Peptidylarginine Deiminase", "Infection and Immunity", Jul. 1999, pp. 3248-3256, vol. 67, No. 7.

Mercado, F., et al., "Is there a relationship between rheumatoid arthritis and periodontal disease?", "J Clin Periodontol", 2000, pp. 267-272, vol. 27.

Mercado, F., et al., "Inter-relationships between rheumatoid arthritis and periodontal disease. A review", "J Clin Periodontol", 2003, pp. 761-772, vol. 30.

Mewar, D., et al., "Autoantibodies in rhematoid arthirits: a review", "Biomedicine & Pharmacotherapy", Oct. 10, 2006, pp. 648-655, vol. 60.

Meyer, O., et al., "Anticitrullinated protein/peptide antibody assays in early rheumatoid arthritis for predicting five year radiographic damage", "Ann Rheum Dis", 2003, pp. 120-126, vol. 62.

Meziere, C., et al., "In Vivo T Helper Cell Response to Retro-Inverso Peptidomimetics", "Journal of Immunology", 1997, pp. 3230-3237, vol. 159.

Moscarello, M., et al., "Myelin in multiple sclerosis is developmentally immature", "J Clin Invest", Jul. 1994, pp. 146-154, vol. 94.

Giallongo, A., et al., "Alpha-enolase (2-phospho-D-glycerate hydro-lyase) (Non-neural enolase) (NNE) (Enolase 1) (Phosphopyruvate hydratase) (C-myc promoter-binding protein) (MBP-1) (MPB-1) (Plasminogen-binding protein)", "NCBI Accession No. P06733", 1986, pp. 1-5.

Nielen, M., et al., "Specific autoantibodies precede the symptoms of rheumatoid arthritis: a study of serial measurements in blood donors", "Arthritis & Rheumatism", Feb. 2004, pp. 380-386, vol. 50, No. 2.

Nienhuis, R., et al., "A New Serum Factor in Patients With Rheumatoid Arthritis the Antiperinuclear Factor", "Ann Rheum Dis", 1964, pp. 302-305, vol. 23.

Nishimura, K., et al., "Meta-analysis: Diagnostic Accuracy of AntiCyclic Citrullinated Peptide Antibody and Rheumatoid Factor for Rheumatoid Arthritis", "Ann Intern Med.", Jun. 5, 2007, pp. 797-808, vol. 146, No. 11.

O'Dell, J., et al., "Treatment of Early Seropositive Rheumatoid Arthritis", "Arthritis & Rheumatism", Feb. 2006, pp. 621-627, vol. 54, No. 2.

O'Dwyer, D., et al., "Identification of the 49-kDa Autoantigen Associated with Lymphocytic Hypophysitis as alpha-Enolase", "J Clin Endocrinol & Metab", Feb. 2002, pp. 752-757, vol. 87, No. 2.

Ogrendik, M., et al., "Serum antibodies to oral anaerobic bacteria in patients with rheumatoid arthritis", "MedGenMed", Jun. 16, 2005, pp. 1-11, vol. 7, No. 2.

Oliver, J., et al., "Risk factors for the development of rheumatoid arthritis", "Scand J Rheumatol", May-Jun. 2006, pp. 169-174, vol. 35, No. 3.

Origuchi, T., et al., "Increased levels of serum IgM antibody to staphylococcal enterotoxin B in patients with rheumatoid arthritis", "Annals of the Rheumatic Diseases", 1995, pp. 713-720, vol. 54.

Orth, T., et al., "Identification and characterization of autoantibodies against catalase and alpha-enolase in patients with primary sclerosing cholangitis", "Clin Exp Immunol", 1998, pp. 507-515, vol. 112.

A  MTX+INF

B  MTX

A

B

METHODS FOR DIAGNOSING RHEUMATOID ARTHRITIS

CROSS-REFERENCE TO RELATED APPLICATIONS

This application is a continuation of U.S. patent application Ser. No. 12/524,465, filed Jul. 24, 2009, which in turn claims priority under 35 U.S.C. §371 of International Patent Application No. PCT/GB08/00267 filed Jan. 25, 2008, which in turn claims priority of United Kingdom Patent Application No. 0722035.3 filed Nov. 9, 2007 and United Kingdom Patent Application No. 0701417.8 filed Jan. 25, 2007. The disclosures of all such applications are hereby incorporated herein by reference in their respective entireties, for all purposes.

REFERENCE TO SEQUENCE LISTING

This application contains a Sequence Listing submitted as an electronic text file named "Sequence_Listing.txt", having a size in bytes of 12.3 kb, and created on Mar. 28, 2008. The information contained in this electronic file is hereby incorporated by reference in its entirety pursuant to 37 CFR §1.52 (e)(5).

FIELD OF THE INVENTION

The present invention relates to methods of diagnosing, prognosing, preventing or delaying onset of or treating rheumatoid arthritis, methods of distinguishing between different types or stages of rheumatoid arthritis, of identifying an individual at risk of developing rheumatoid arthritis, and of monitoring efficacy of a treatment regime in an individual being treated for rheumatoid arthritis, using a citrullinated enolase peptide to detect or capture antibodies associated with rheumatoid arthritis.

BACKGROUND OF THE INVENTION

Rheumatoid arthritis (RA) is a chronic, inflammatory joint disorder that is considered to be autoimmune, although the autoantigens that trigger and sustain the immune response remain unknown. There are several known genetic and environmental risk factors for development of the disease. The main genetic risk factor is a sequence common to several HLA DRB1 alleles known as the shared epitope (SE) (reviewed in Silman and Pearson (2002) *Arthritis Res* 4:S265-S272). Environmental factors which affect the risk of RA are thought to include female sex hormones, diet, cigarette smoking and exposure to silica dust (reviewed in Oliver and Silman (2006) *Scand J Rheumatol* 35: 169-174. Exposure to infection has been suggested to act as a trigger for RA, and a number of agents have been implicated, including Epstein-Barr virus, parvovirus, *Proteus* and *Mycoplasma* (Silman and Pearson, supra). Findings which make Epstein-Bar virus a promising candidate include the discovery that antibodies in RA cross-react with EBV nuclear antigen, sequence similarity between EBV glycoprotein and HLA DRB1-SE and EBV DNA load in peripheral blood mononuclear cells of RA patients has been found to be 10 times that of controls (Oliver and Silman, supra; Balandraud, Roudier and Roudier (2004) *Autoimmunity Rev* 3:362-367). The staphylococcal enterotoxin B has also been suggested to play a critical role in the pathogenesis of RA (Origuchi et al (1995) *Ann Rheum Dis* 54:713-720), as has human parvovirus B19 (Takahashi et al (1998) *Proc Natl Acad Sci USA* 95:8227-8232). However, other researchers have cautioned against ignoring the possibility that RA is unrelated to infection, concluding that there is no overwhelming evidence linking any single known infectious agent with RA (Carty, Snowden and Silman (2004) *Ann Rheum Dis* 63:46-49). According to those authors, reported links could in fact be explained in other ways, for example evidence of the presence of bacteria in synovial fluid could be explained by inflamed synovium acting as a non-specific trap for bacterial fragments. Furthermore, studies identifying elevated antibodies to particular infectious agents were not always reproducible.

Unlike most other autoimmune rheumatic diseases, the dominant autoantigens in RA are unknown. Circulating IgM antibodies that are specific for IgG are present in up to 75% of patients with RA, and are known as rheumatoid factors. However, rheumatoid factors are also present in patients with other diseases and in up to 5% of healthy individuals (Mageed RA: The RF antigen. In *Manual of Biological Markers of Disease* Edited by: van Venrooij W J, Maini R N. Dordrecht: Kluwer Academic Publishing; 1996:1-27). Other antibodies are also present in sera from patients with RA, including antiperinuclear factor (Nienhuis R L & Mandema E, *Ann Rheum Dis* 1964, 23:302-305) and antikeratin antibodies (Young B J et al, *Br Med J* 1979, 2:97-99). Because both antiperinuclear factor and antikeratin antibodies react with human filaggrin (Sebbag M et al, *J Clin Invest* 1995, 95:2672-2679) they were collectively designated "antifilaggrin antibodies". It was subsequently reported that binding of anti-filaggrin antibody epitopes is dependent on the presence of citrulline, an amino acid derived from arginine as a result of a post-translational modification catalysed by the enzyme peptidylarginine deiminase (PAD) (Schellekens G A et al, *J Clin Invest* 1998, 101:273-281; Girbal-Neuhauser E et al, *J Immunol* 1999, 162:585-594). Anti-filaggrin antibodies have been found at higher concentrations in synovial membrane than in synovial fluid and peripheral blood (Masson-Bessiere C et al, *Clin Exp Immunol* 2000, 199:544-552) from patients with RA. However, filaggrin is notably absent from the RA joint (Nijenhuis S et al, *Clin Chim Acta* 2004, 350:17-34). Citrullinated fibrin, on the other hand, is present in interstitial deposits in the synovial membrane (Masson-Bessiere C et al (supra)) and is recognised by anti-filaggrin antibodies. Endogenous citrullination of fibrin has also been demonstrated in murine models of arthritis (Vossenaar E R et al, *Arthritis Rheum* 2003, 48-2489-2500). These antibodies have collectively been named ACPAs (anti-citrullinated protein antibodies) and also include anti-SA antibodies, which bind citrullinated vimentin (Vossenaar E R et al, *Arthritis Res Ther* 2004, 6:R142-R150; Vossenaar E R et al, *Ann Rheum Dis* 2004, 63:373-381; Despres N et al, *J Rheumatol* 1994, 21:1027-1033). Anti-citrullinated collagen type II antibodies have also been described (Burkhardt et al (2005) *Eur. J. Immunol.* 35:1643-1652), as well as antibodies recognising a synthetic citrullinated peptide corresponding to a sequence in Epstein-Barr nuclear antigen 1 (EBNA-1) (Anzilotti C et al (2006) *J Rheumatol.* 33(4):647-51). A further candidate is citrullinated α-enolase (Kinloch et al (2005) *Arthritis Research & Therapy* 7:R1421-R1429). Sera of RA patients reacted with citrullinated α-enolase, and a commercially available antibody against α-enolase recognized a band co-migrating with purified α-enolase in synovial cell lysates from RA patients. The band which RA sera reacted with was excised and identified by mass spectrometry as citrullinated α-enolase.

The identification of new antigens and epitopes in RA would supplement or complement existing diagnostic and prognostic tests for RA and might also suggest therapeutic strategies.

A single cyclic citrullinated peptide derived from filaggrin (anti-CCP1) has been used as the basis of an ELISA test for rheumatoid arthritis, although the sensitivity of the test was not as high as the sensitivity of IgM rheumatoid factors (reviewed in E. R. Vossenaar W. J. van Venrooij, *Clin. Applied Immunol. Rev,* 4 (2004) 239-262). A second generation test, anti-CCP2, based on synthetic cyclic citrullinated peptides having no homology with filaggrin or other known proteins is preferred (Vossenaar & van Venrooij (supra)). The anti-CCP2 assay is more sensitive (up to 80%) and specific (97%) for RA than rheumatoid factors are (Nijenhuis S et al, *Clin Chim Acta* 2004, 350:17-34). Anti-CCPs may occur early in disease (van Gaalen Fa et al, *Arthritis Rheum* 2004, 50:709-715), or even before clinical manifestations (Rantapaa-Dahlqvist S et al, *Arthritis Rheum* 2003, 48:2741-2749). Anti-CCP positivity also predicts a more aggressive form of RA (Vencovsky J et al, *Ann Rheum Dis* 2003, 62:427-430; Forslind K et al, *Ann Rheum Dis* 2004, 63:1090-1095). Schellekens et al (*Arthritis Rheum*. (2000) 43(1):155-63) used a cyclic peptide having the sequence HQCHQESTXGRSRGRCGRSGS (SEQ ID NO. 1) where X is citrulline as the basis for a anti-CCP test. WO 01/46222 to Innogenetics N.V. describes synthetic citrulline-containing peptides which are recognised by RA sera. WO 03/050542 and EP 1 456 662 B1 to Stichting voor de Technische Wetenschappen describe a number of peptides that were identified after screening a library of synthetic cyclic citrullinated peptides with a pool of RA sera. The commercial anti-CCP2 assay was developed based on a proprietary composition using some or all of these peptides, to facilitate and standardise the screening of RA sera for the presence of anti-citrullinated protein reactivity. The assay is available from Euro-diagnostica AB, Medeon, SE-205 12 Malmo, Sweden as "Immunoscan RA" (Catalogue No. RA-96RT). Vossenaar & van Venrooij (supra) report that the anti-CCP2 ELISA is commercially available from Euro-Diagnostica, Arnhem, The Netherlands; Axis-Shield, Dundee, Scotland; INOVA, San Diego, USA and that all of these companies use the same type of CCP2 peptides in their assay. The assay has been reported to have a sensitivity of 60%-80%. Average sensitivity is around 70%. However, since anti-CCP positivity is also a severity factor for RA, the sensitivity will depend on the RA-population in which the sensitivity was determined. Although the commercial anti-CCP2 test is useful, it is based on several different artificial synthetic peptides that do not correspond to any known protein sequences, rather than a single peptide derived from a genuine RA epitope. Therefore, reactivity in the anti-CCP2 test may not reflect a causative mechanism. It is also a poor marker of disease subsets. Since the CCP2 test comprises several different epitopes, it diagnoses CCP positive RA, but this group of patients might comprise several disease subsets, with different disease course, that might need different treatments.

SUMMARY OF THE INVENTION

Surprisingly, the present inventors have found that a citrullinated α-enolase peptide can form the basis of a new diagnostic test for RA, which complements the existing anti-CCP assay. It is surprising that this test is highly specific for RA, as antibodies to α-enolase have been detected in a wide range of autoimmune and other diseases.

Enolase is a glycolytic enzyme which is believed to have been conserved through millions of years of evolution, and which generally has a cytoplasmic location (reviewed in Pancholi (2001) *Cell Mol Life Sci* 58:902-920). In vertebrates, the enzyme occurs as three isoforms: α-enolase is found in a variety of tissues including liver and joints; β-enolase is almost exclusively found in muscle tissues; and γ-enolase is found in neuron and neuroendocrine tissues. In addition to its enzymatic functions, α-enolase is thought to be a receptor for plasminogen, and is expressed on the surface of various eukaryotic cells including neutrophils, monocytes, T cells and B cells. Enolase also acts as a plasminogen receptor on the surface of group A streptococci. α-enolase has been reported to be an immunodominant antigen in patients suffering from systemic candidiasis (Pancholi 2001(supra)) and bakers' yeast (*Saccharomyces cerevisiae*) enolase has been identified as an important allergen in inhalant allergies to bakers' yeast (Pancholi 2001(supra)). As well as being directed to enolases of non-self origin, immune reactions to self enolases have also been described. Anti-enolase antibodies have been identified in a variety of autoimmune diseases, in particular systemic lupus erythromatosus (SLE), vasculitis, nephritis, ulcerative colitis, Crohn's disease, primary sclerosing cholangitis, biliary cirrhosis, autoimmune hepatitis, polyglandular candidal ectodermal dystrophy, discoid lupus erythematosus, cancer-associated retinopathy, endometriosis and acute rheumatic fever. α-enolase has also more recently been identified as an autoantigen in early rheumatoid arthritis (Saulot et al (2002) *Arthritis & Rheumatism* 46:1196-1201), Hashimoto's encephalopathy (Fujii et al (2005) *J Neuroimmunol* 162: 130-136) and lymphocytic hypophysitis (O'Dwyer et al (2002) *J Clin Endocrinol & Metab* 87:752-757). Interestingly, in this latter study, antibodies present in patient sera were additionally found to react with *S. cerevisiae* enolase.

Four major enolase epitopes that bound strongly to the sera from cancer-associated retinopathy patients were identified as residues 31-38 ($^{31}$FRAAVPSG$^{38}$(SEQ ID NO: 2)), 176-183 ($^{176}$ANFREAMR$^{183}$(SEQ ID NO: 3)), 421-428 ($^{421}$AK-FAGRNF$^{428}$(SEQ ID NO: 4)) and 56-63 ($^{56}$RYMGKGVS$^{63}$ (SEQ ID NO: 5)) (Pancholi (supra)). Two peptides 53-87 and 207-238 within the sequence of enolase were significantly recognized by sera from endometriosis patients. Notably, the first such peptide spans a region of enolase overlapping with the 56-63 epitope recognized by sera of patients with cancer-associated retinopathy. The amino terminal region of α-enolase (1-157) was recognized by 5/6 patients with Hashimoto's encephalopathy, but not by sera from controls (Fujii et al (2005) *J Neuroimmunol* 162: 130-136). In contrast, sera from all patients and controls apparently reacted non-specifically with a recombinant carboxy region (246-436) and full length enolase, but did not react detectably with its mid-region (148-304).

In contrast to the immunodominant epitopes identified in cancer-associated retinopathy and endometriosis defined above, the present inventors surprisingly found that antibodies in sera from RA patients reacted preferentially to a single peptide 5-21 of citrullinated human α-enolase, of which an immunodominant epitope was identified surrounding the second citrulline residue, at position 15.

The listing or discussion of a prior-published document in this specification should not necessarily be taken as an acknowledgement that the document is part of the state of the art or is common general knowledge.

One dot represents one individual for each of the nine citrullinated α-enolase peptides. Horizontal lines indicate mean $OD_{450}$ for the individual peptides.

Figure 2:
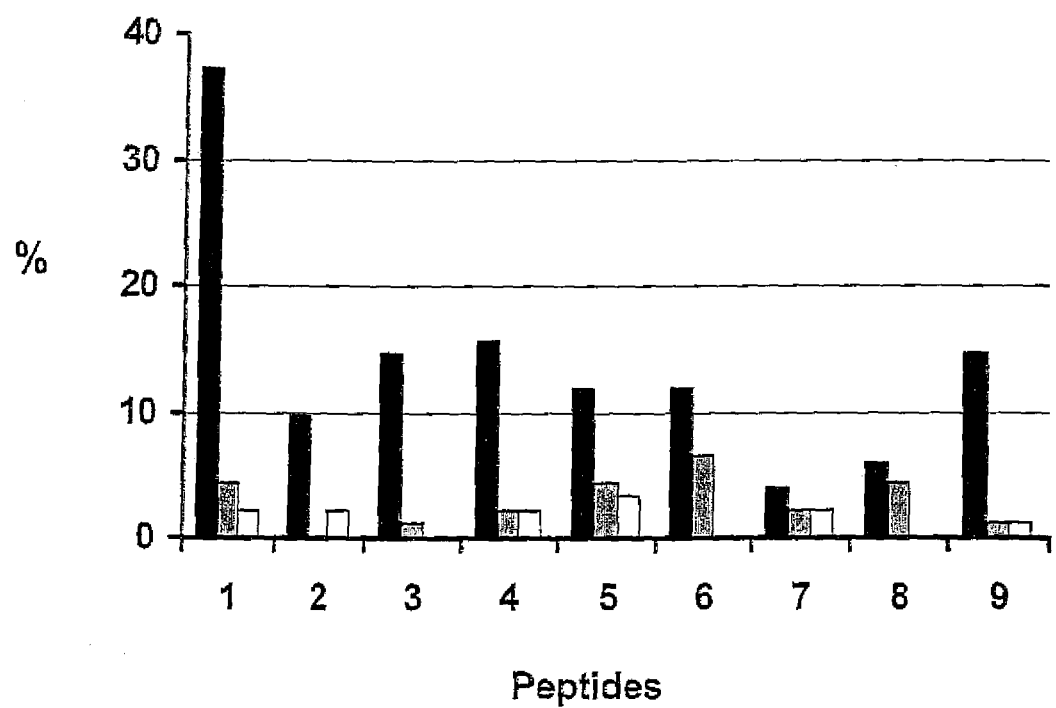

FIG. 2 is a chart showing the percentage of positive individuals (y-axis) for antibodies to each of the nine citrullinated α-enolase peptides (x-axis). Data for RA patients are represented by black columns, non-RA patients by grey columns and healthy controls by white columns Data were generated by ELISA using sera from 102 RA patients, 92 non-RA patient controls and 92 healthy controls.

FIGS. 3A and 3B are charts showing results where RA patient sera were tested for antibodies to each of Peptides 1A to 1D. FIG. 3A shows the percentage of RA patient sera scored as positive for antibodies to each of Peptides 1A to 1D. FIG. 3B shows the quantity of IgG in patient sera reactive with each of Peptides 1A to 1D, reflected by OD450 in ELISA. Horizontal bars indicate mean $OD_{450}$ for each peptide. *$P<0.0001$; $P<0.01$.

FIGS. 4A-D are graphs showing the results of treating RA-patients with a combination of methotrexate (MTX) and Infliximab (INF) (n=11) 18 and 52 weeks post treatment (4A and 4B), or MTX alone (n=13) (4C and 4D). DAS28 (CRP (C-reactive protein) and ESR (erythrocyte sedimentation rate)) were assessed, by a rheumatologist, pre-treatment as well as 6, 18 and 52 weeks post treatment. The horizontal bars indicate mean CRP and ESR at the different time points.

FIG. 5A is a chart showing that anti-Peptide 1A antibody levels decreased over time in RA patients treated with MTX+ INF (n=11). FIG. 5B is a chart showing that anti-Peptide 1A antibody levels increased in patients treated with MTX alone (n=13). Data did not reach statistical significance at any time point investigated. Sera were collected pre-treatment, as well as 6, 18 and 52 weeks post treatment. IgG was measured by ELISA and presented as $OD_{450}$ (peptide)–$OD_{450}$(carbonate buffer). The horizontal bars indicate mean $OD_{450}$ at the different time points. Methotrexate=MTX; Infliximab=INF.

FIGS. 6A-B are graphs showing the short IgG responses to citrullinated Peptide 1A (black circles) and to the arginine containing control Peptide 1D (white circles) were measured by ELISA for various dilutions of rabbit anti-Peptide 1A antisera (FIG. 6A) or affinity purified human anti-Peptide 1A antisera (FIG. 6B). Data are presented as $OD_{450}$ (peptide)-$OD_{450}$ (background).

Figure 7:
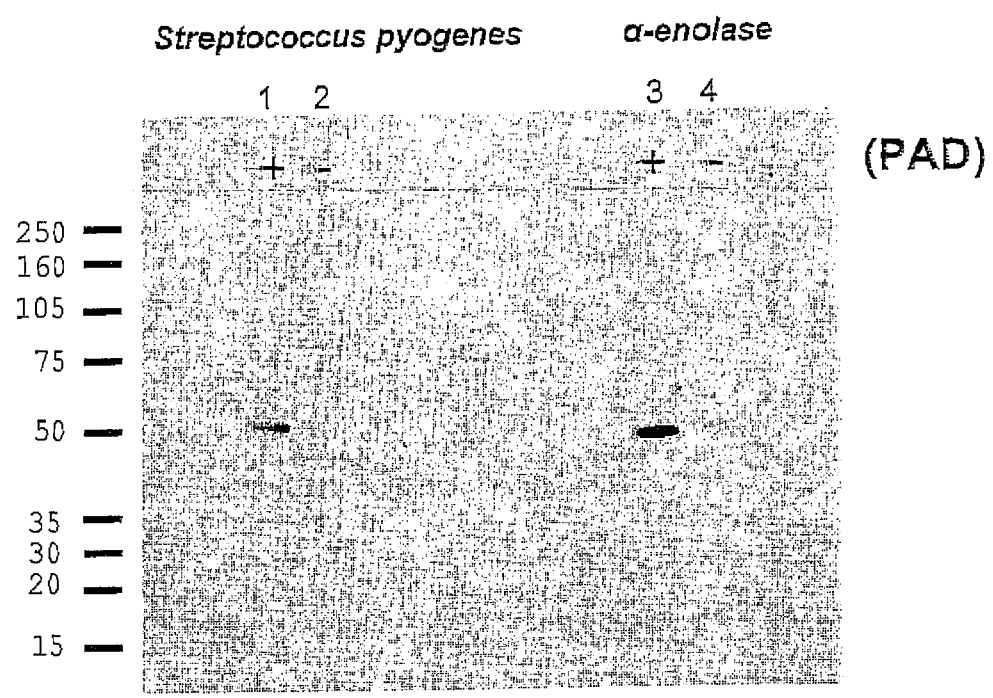

FIG. 7 is a chart showing the detection of enolases using rabbit polyclonal antibody in a western blot assay. Rabbit polyclonal anti-Peptide 1A antibodies bound a protein of around 50 kD in PAD-treated *Streptococcus pyogenes* lysates (lane 1), but not in untreated bacterial lysates (lane 2). α-enolase treated with PAD was used as a positive control (lane 3), while untreated α-enolase served as a negative control (lane 4). Molecular weights (kDa) are indicated at the left of the panel.

Figure 8:
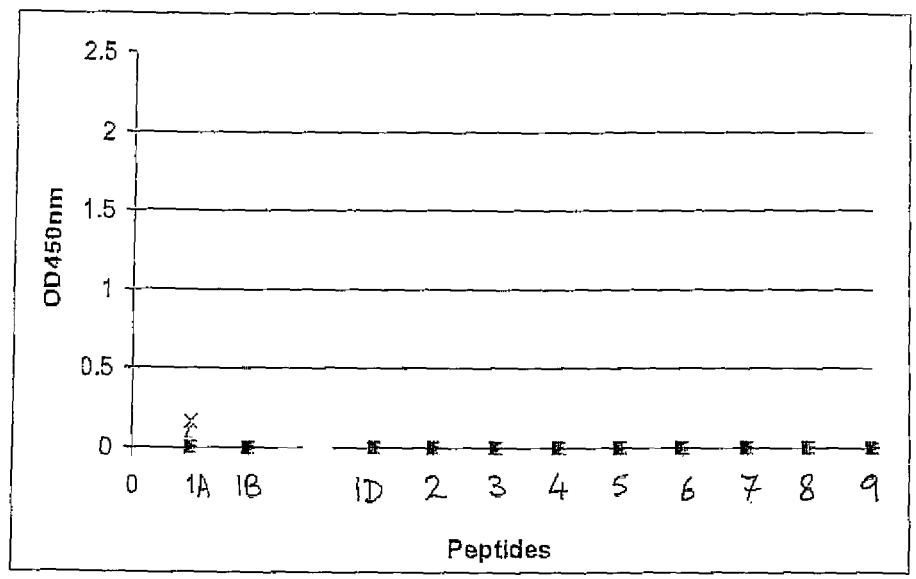
Figure 8:
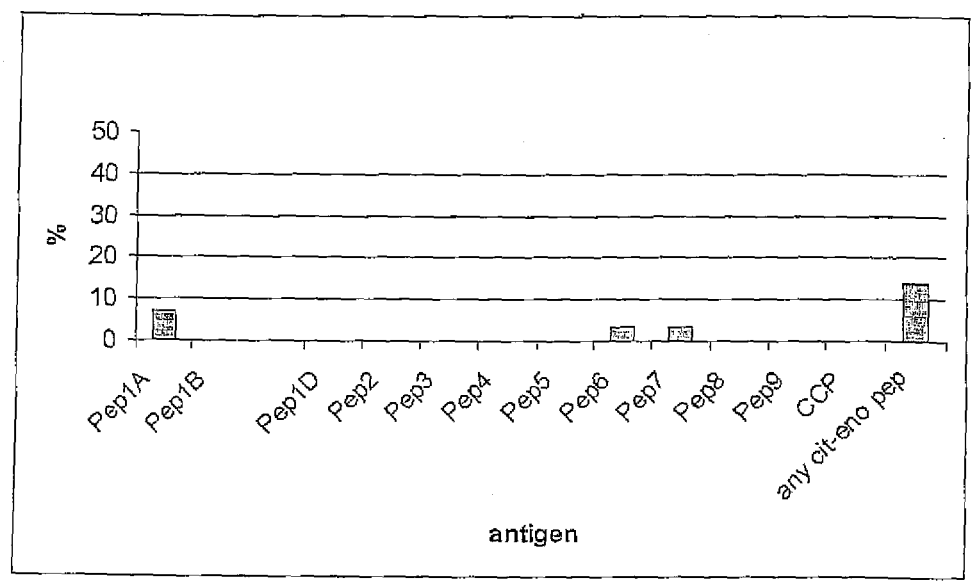

FIG. 8A is a chart showing $OD_{450}$ values (after subtraction of background) of sera samples of each of 29 SLE patients in ELISA for quantification of antibody to each of Peptides 1A, 1B, 1D and 2 to 9. Results of each patient are represented by a different symbol, but for most peptides, the symbols overlap. FIG. 8B is a chart showing the percentage of SLE (systemic lupus erythematosus) patients scored positive for antibodies to each of Peptides 1A, 1B, 1D and 2 to 9, any of these peptides (any cit-eno pep) or a commercially available anti-cyclic citrullinated peptides assay (CCP).

FIGS. 9A-C are charts showing that RA-patients (n=102) (FIG. 9A) have a stronger IgG response to citrullinated α-enolase peptides than disease controls (n=110) (FIG. 9B) and healthy controls (FIG. 9C) (n=92). IgG was measured by ELISA and data presented as peptide $OD_{450}$ with the background (carbonate buffer) $OD_{450}$ subtracted. One dot represents the reactivity of one serum sample with each of the eleven citrullinated α-enolase peptides. The grey lines indicate mean $OD_{450}$ for the antibody response to the individual peptides. nd=not done.

Figure 10:
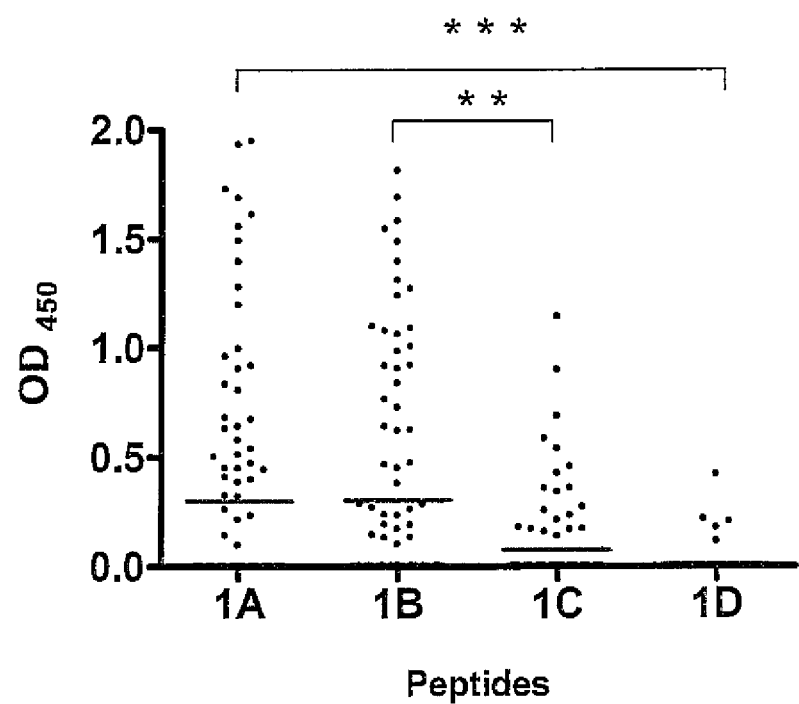

FIG. 10 is a chart showing that the antibody response to the immunodominant peptide 1 is dependent on the presence of citrulline, demonstrated by the low IgG-levels recorded towards the arginine-containing control peptide 1D, *$P<0.0001$. It is the second citrulline residue, rather than the first, that generates the high IgG levels for this B cell epitope (compare peptide 1B and 1C), $P<0.01$. Data was generated by ELISA on sera from 102 RA patients and presented as $OD_{450}$ (peptide)-$OD_{450}$ (background).

Figure 11:
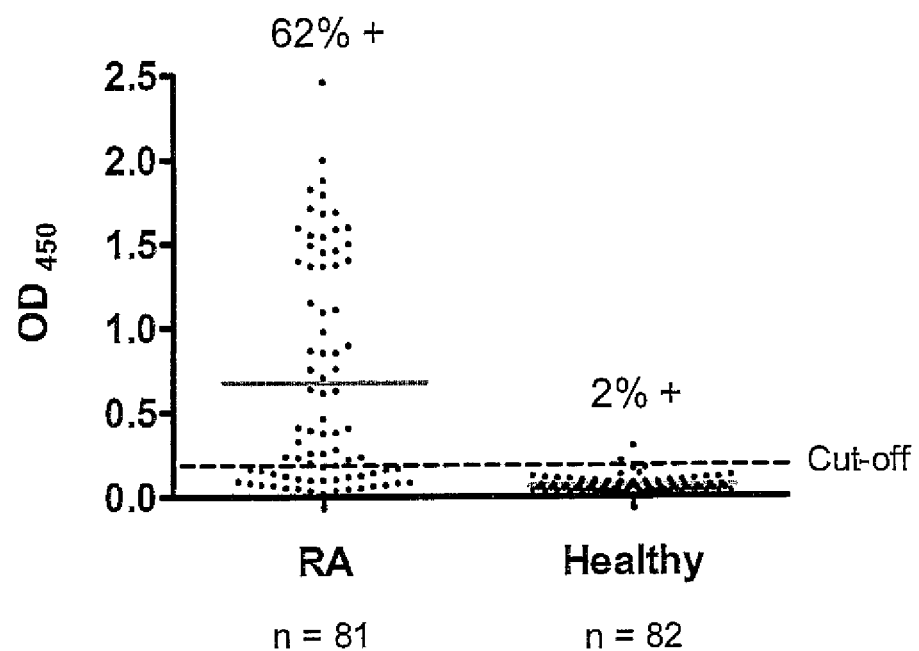

FIG. 11 is a chart showing that a strong anti-CEP-1 antibody response was also found in the US RA cohort. 62% of patients (n=81) had anti-CEP-1 antibodies compared to 2% of healthy controls (n=82). Data was generated by ELISA and presented as $OD_{450}$ (peptide)-$OD_{450}$ background. The dotted line indicates the cut-off value for positive samples, based on the 98th percentile of controls.

FIGS. 12A-F are charts showing that anti-CEP-1 antibodies do not cross-react with other citrullinated α-enolase epitopes. A dose dependent decrease in binding to CEP-1-coated plates was seen in six anti-CEP-1 positive RA serum samples pre-incubated with increasing concentrations of CEP-1 (FIG. 12A), while pre-incubation with the control peptide 1D (FIG. 12B), peptide 4 (FIG. 12C), peptide 7 (FIG. 9D) peptide 9 (FIG. 12E) or peptide 11 (FIG. 12F) did not result in decreased antibody binding. Sera were pre-incubated in liquid phase with increasing concentrations (0, 1, 10 and 100 µg/ml) of peptides before transferred to CEP-1-coated ELISA plates. Data are presented as $OD_{450}$ for each of the peptide concentrations.

Figure 13:
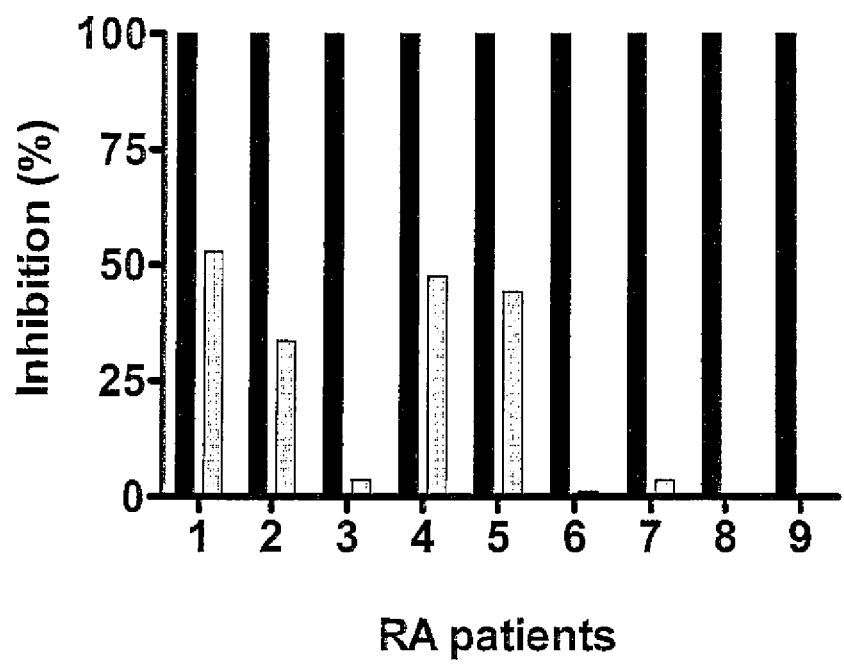

FIG. 13 is a chart showing that RA patients have anti-CEP-1-specific as well as CCP-cross-reactive anti-CEP-1 antibodies. Individual sera exhibited differing degrees of cross-reactivity, as demonstrated by a reduction in antibody binding that ranged between 0 and 53%, following pre-incubation with CCP (grey bars). Sera from nine double positive (anti-CEP-1 positive and anti-CCP positive) RA patients were pre-absorbed on CEP-1- or CCP-coated plates before transferred to CEP-1-coated plates. Results are expressed as the percentage of maximum inhibition, which by definition was set to 100% for pre-incubation with CEP-1 (black bars).

Figure 14:
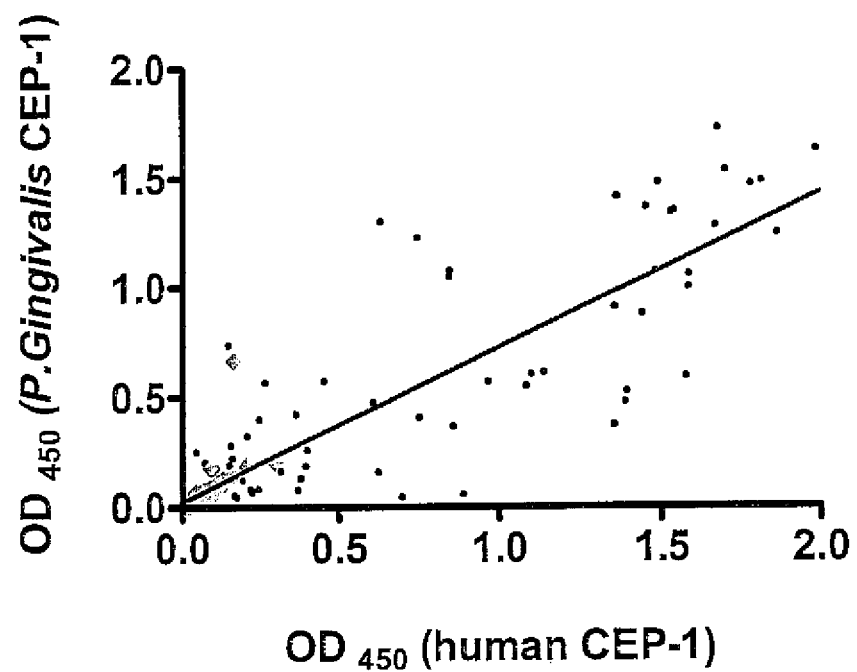

FIG. 14 is a chart showing that RA patients have antibodies to the *P. gingivalis* version of CEP-1. Fifty four percent of rheumatoid patients were positive for anti-*P. gingivalis* CEP-1 antibodies (black circles) in comparison to 2% of healthy controls (grey diamonds). The antibody response to *P. gingivalis* CEP-1 (y-axis) correlates strongly with the antibody response to the human version of this peptide (x-axis) ($r^2=0.803$, $p<0.0001$). IgG was measured by ELISA in serum from 81 RA patients and 82 healthy controls. Data are presented as $OD_{450}$.

Figure 15:
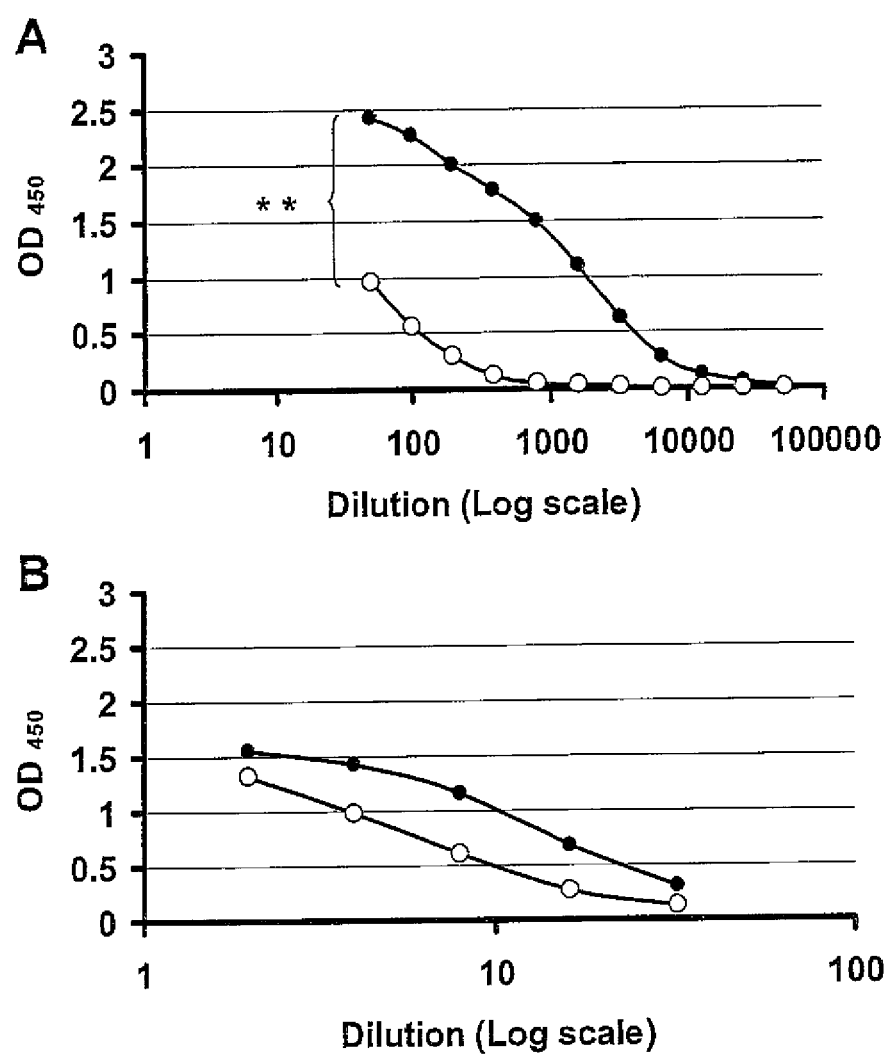

FIGS. 15A-B are charts showing the specificity of affinity purified rabbit and human antibodies for the immunodominant epitope CEP-1. A high degree of CEP-1-specificity was demonstrated for the rabbit polyclonal antibody (FIG. 15A), **$P<0.01$, while cross-reactivity with the control peptide was observed for the affinity purified human immunoglobulins (FIG. 15B). IgG responses to CEP-1 (peptide 1A) (black circles) and to the arginine containing control peptide (peptide 1D) (white circles) was measured in serial dilutions by ELISA. Data are presented as $OD_{450}$ (peptide)-$OD_{450}$ (background).

FIGS. 16A-F are graphs showing that Anti-CEP-1 antibodies cross-react with bacterial enolase. Rabbit polyclonal anti-CEP-1 antibodies (FIG. 16A) as well as anti-CEP-1 antibodies purified from an RA patient (FIG. 16B), bound a protein of around 50 kDa in the PAD-treated (lane 1) and in the untreated (lane 2) *P. gingivalis* lysates. Bacterial enolase was demonstrated in both lane 1 and 2 (FIG. 16C). Presence of citrullinated proteins was also detected in both *P. gingivalis* lysates (FIG. 16D). *S. pyogenes* lysates treated with PAD was bound by the rabbit anti-CEP-1 antibody (lane 5), whilst the untreated lysate (lane 6) was not (FIG. 16E). Citrullinated proteins were present in the PAD-treated *S. pyogenes* lysate (lane 5), but not in the untreated lysate (lane 6) (FIG. 16F). Citrullinated α-enolase (lanes 3 and 7) and uncitrullinated α-enolase (lanes 4 and 8) served as controls. Proteins were separated on SDS-PAGE gels and blotted with affinity purified rabbit or human anti-CEP-1 antibodies, a rabbit anti-enolase antibody or an anti-citrulline (modified) detection kit. nd=not done.

Figure 17:
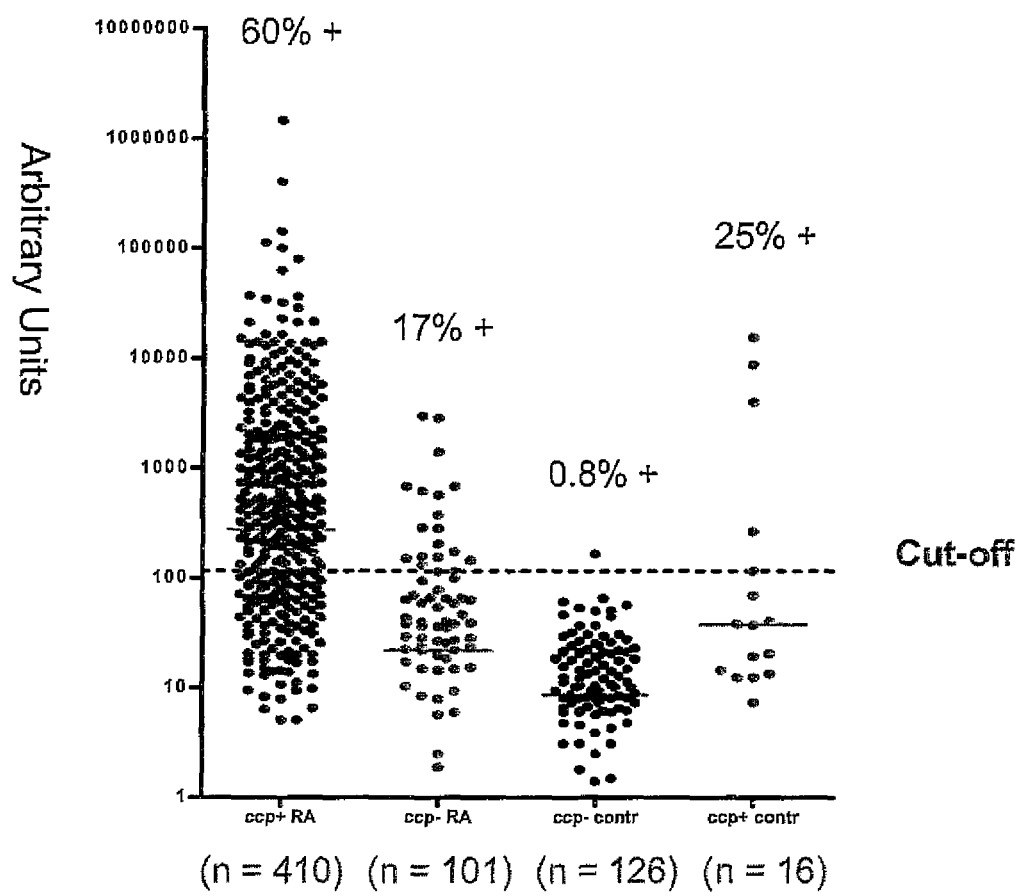

FIG. 17 is a chart showing an antibody response to CEP-1 in a Swedish cohort. Rheumatoid arthritis patients (RA) and healthy controls (contr) were assigned to ccp+ or ccp– groups according to the reactivity of their sera in the commercial CCP ELISA, thus providing four groups: ccp+ RA, ccp– RA, ccp– contr and ccp+ contr. Reactivities of sera in the assay for CEP-1 were determined Data are presented as Arbitrary Units (AU), that were calculated based on a standard curve of a pool of strongly anti-CEP-1 positive RA sera, which was given an AU of 10 000. Each dot represents the reactivity of one serum sample. The grey lines indicate the mean for each group. Data points above the cut-off value are considered positive for antibodies to CEP-1.

DETAILED DESCRIPTION

A first aspect of the invention provides a citrullinated enolase peptide with an amino acid sequence comprising or consisting of the amino acid sequence of a region of human α-enolase consisting of five to 150 amino acids encompassing amino acids 14 to 16 of human α-enolase in which amino acid 15 is citrulline or an analogue thereof; or a variant thereof, for use in medicine.

Amino acids 14 to 16 of human α-enolase are SRG (SXG when citrullinated, with X representing a citrulline residue), which the present inventors believe to be a key region of the immunodominant epitope of citrullinated human α-enolase in RA. The full length human α-enolase protein sequence (NCBI Accession No. P006733, SEQ ID NO. 6) is given below.

By "a region of human α-enolase" we mean a single contiguous sequence of human α-enolase. Thus, "a region of human α-enolase consisting of five to 150 amino acids encompassing amino acids 14 to 16 of human α-enolase in which amino acid 15 is citrulline or an analogue thereof" is a region in which SXG must be contiguous with at least two amino acids which occur immediately adjacent to SXG in human α-enolase. Thus, the region of human α-enolase consists of or comprises a pentapeptide motif selected from FDSXG, DSXGN and SXGNP. The region of human α-enolase may comprise further contiguous sequence, which may be N-terminal to the first residue of any one of these pentapeptide motifs, or C-terminal to the last residue of any one of these pentapeptide motifs, or both. Preferably, the region of human α-enolase consists of fewer than 150, 125, 100, 75, 70, 65, 60, 55, 50, 45, 40, 35, 30, 25, 20 or fewer than 15 amino acids. For example, it may consist of 14, 13, 12, 11, 10, 9, 8, 7, 6, or 5 amino acids. The citrullinated enolase peptide comprises the region of human α-enolase or a variant thereof and may also comprise further amino acids (not derived from human α-enolase), typically N-terminal or C-terminal to the region. For example, the citrullinated enolase peptide may contain a short peptide tag such as a glutathione S-transferase tag to facilitate purification of the citrullinated enolase peptide. Thus, the citrullinated enolase peptide may be a fusion of a region of human α-enolase and a further polypeptide sequence. Where the citrullinated enolase peptide is to be rendered cyclic by virtue of a cysteine bridge, a cysteine residue may be included at each of the N- and C-termini Preferably, the region of human α-enolase comprises or consists of KIHAXEIFDSXGNPTVE (SEQ ID NO. 7) or KIHAREIFDSXGNPTVE (SEQ ID NO. 8) in which X is citrulline or an analogue thereof, which corresponds to positions 5-21 of the full length human α-enolase protein. Preferably, the citrullinated enolase peptide is CKIHAXEIFDSXGNPTVEC (Peptide 1A, SEQ ID NO. 9) or CKIHAREIFDSXGNPTVEC (Peptide 1B, SEQ ID NO. 10).

Suitable analogues of citrulline are disclosed in WO 03/050542 to Stichting Voor de Technische Wetenschappen (incorporated herein by reference).

A "variant" of a region of human α-enolase consisting of five to 150 amino acids encompassing amino acids 14 to 16 of human α-enolase in which amino acid 15 is citrulline or an analogue thereof is a region wherein at one or more positions there have been amino acid insertions, deletions, or substitutions, either conservative or non-conservative, compared to the corresponding positions of the full length human α-enolase sequence. Such variations may occur within SXG, and/or within the pentapeptide motif comprising SXG, and/or elsewhere in the region of human α-enolase. Variations in the region of human α-enolase may be naturally occurring varia-

```
  1 msilkihare ifdsrgnptv evdlftskgl fraavpsgas tgiyealelr dndktrymgk 61 gvskavehin ktiapalvsk klnvteqeki dklmiemdgt enkskfgana ilgvslavck 121 agavekgvpl yrhiadlagn sevilpvpaf nvinggshag nklamqefmi lpvgaanfre 181 amrigaevyh nlknvikeky gkdatnvgde ggfapnilen keglellkta igkagytdkv 241 vigmdvaase ffrsgkydld fkspddpsry ispdqladly ksfikdypvv siedpfdqdd 301 wgawqkftas agiqvvgddl tvtnpkriak avnekscncl llkvngigsv teslqackla 361 qangwgvmvs hrsgetedtf iadlvvglct gqiktgapcr serlakynql lrieeelgsk 421 akfagrnfrn plak
``` tions, such as may be encoded by variant alleles of the human α-enolase gene, or encoded by an α-enolase gene of another organism, such as a mammal or bird. The term "variants" also encompasses peptides having variations from regions of α-enolase proteins wherein the variations have not been observed in nature.

By "conservative substitutions" is intended combinations such as Val, Ile, Leu, Ala, Met; Asp, Glu; Asn, Gln; Ser, Thr, Gly, Ala; Lys, Arg, His; and Phe, Tyr, Trp. Preferred conservative substitutions include Gly, Ala; Val, Ile, Leu; Asp, Glu; Asn, Gln; Ser, Thr; Lys, Arg; and Phe, Tyr.

A "variant" may have modified amino acids. Suitable modifications include acetylation, glycosylation, hydroxylation, methylation, nucleotidylation, phosphorylation, ADP-ribosylation, and other modifications known in the art. Such modifications may occur postranslationally where the peptide is made by recombinant techniques. Otherwise, modifications may be made to synthetic peptides using techniques known in the art. Modifications may be included prior to incorporation of an amino acid into a peptide. Carboxylic acid groups may be esterified or may be converted to an amide, an amino group may be alkylated, for example methylated.

A "variant" typically has at least 25%, at least 50%, at least 60% or at least 70%, preferably at least 80%, more preferably at least 90%, even more preferably at least 95%, yet more preferably at least 99%, most preferably at least 99.5% sequence identity to the polypeptide from which it is derived.

The percent sequence identity between two polypeptides may be determined using suitable computer programs, for example the GAP program of the University of Wisconsin Genetic Computing Group and it will be appreciated that percent identity is calculated in relation to polypeptides whose sequences have been aligned optimally.

The alignment may alternatively be carried out using the Clustal W program (Thompson et al., (1994) *Nucleic Acids Res.*, 22(22), 4673-80). The parameters used may be as follows:

Fast pairwise alignment parameters: K-tuple(word) size; 1, window size; 5, gap penalty; 3, number of top diagonals; 5. Scoring method: x percent.

Multiple alignment parameters: gap open penalty; 10, gap extension penalty; 0.05.

Scoring matrix: BLOSUM.

Such variants may be natural or made using the methods of protein engineering and site-directed mutagenesis as are well known in the art.

Typically, a variant may have one or no substitutions, either conservative or non-conservative, within SXG. The "X" residue of SXG is typically unchanged. The variant typically has two, one or no substitutions, either conservative or non-conservative, within the pentapeptide motif comprising SXG, whether it is FDSXG, DSXGN or SXGNP. Where the variant is a variant of KIHAXEIFDSXGNPTVE (SEQ ID NO. 7), the variant may typically have fewer than 8, 7, 6, 5, 4, 3, or 2 substitutions, or no substitutions, either conservative or non-conservative, within KIHAXEIFDSXGNPTVE (SEQ ID NO. 7). The "X" residue at position 5 of KIHAXEIFD-SXGNPTVE (SEQ ID NO. 7), which corresponds to position 9 of the full length human α-enolase protein, is citrulline or an analogue thereof. The "X" residue corresponding to this position of the variant is typically unchanged, but where it is changed, it is typically changed to an arginine residue. A variant may typically have fewer than 40, 35, 30, 25, 20, 18, 16, 14, 12, 11, 10, 9, 8, 7, 6, 5, 4, 3 or 2 substitutions, or no substitutions, either conservative or non-conservative, elsewhere in the region of human α-enolase.

A variant citrullinated enolase peptide typically is one which, when used in a test for diagnosing or prognosing rheumatoid arthritis as described herein, does not result in a significantly reduced sensitivity or specificity of that test as compared to the test using the citrullinated enolase peptide lacking the variation. Preferably, the sensitivity and specificity for RA of the test based on the variant citrullinated enolase peptide is at least equivalent to the sensitivity and specificity for RA of the test using the citrullinated enolase peptide lacking the variation. More preferably, either or both of the sensitivity and specificity for RA are improved when the variant citrullinated enolase peptide is used. As described in Example 1, peptide variants based on the sequence of Peptide 1 (KIHAXEIFDSXGNPTVE, SEQ ID NO. 7) were assessed for their sensitivity for RA by immunoassay. Peptide 1A (CKIHAXEIFDSXGNPTVEC, SEQ ID NO. 9) had a sensitivity of about 37.3% and Peptide 1B (CKIHAREIFD-SXGNPTVEC, SEQ ID NO. 10) had a sensitivity of about 40%. Accordingly, Peptide 1B is considered to be a variant of Peptide 1A within the meaning given above. On the other hand, Peptide 1C (CKIHAXEIFDSRGNPTVEC, SEQ ID NO. 11) had a sensitivity of about 20% and Peptide 1D (CKIHAREIFDSRGNPTVEC, SEQ ID NO. 12) had a sensitivity of about 4.9%. Peptides 1C and 1D are not considered to be variants of Peptide 1A within the meaning given above.

By "peptide" we include not only molecules in which amino acid residues are joined by peptide (—CO—NH—) linkages but also molecules in which the peptide bond is reversed. Such retro-inverso peptidomimetics may be made using methods known in the art, for example such as those described in Meziere et al (1997) *J. Immunol.* 159, 3230-3237, incorporated herein by reference. This approach involves making pseudopeptides containing changes involving the backbone, and not the orientation of side chains. Retro-inverse peptides, which contain NH—CO bonds instead of CO—NH peptide bonds, are much more resistant to proteolysis.

Similarly, the peptide bond may be dispensed with altogether provided that an appropriate linker moiety which retains the spacing between the Cα atoms of the amino acid residues is used; it is particularly preferred if the linker moiety has substantially the same charge distribution and substantially the same planarity of a peptide bond.

It will be appreciated that the peptide may conveniently be blocked at its N- or C-terminus so as to help reduce susceptibility to exoproteolytic digestion.

Peptides (at least those containing peptide linkages between amino acid residues) may be synthesised by the Fmoc-polyamide mode of solid-phase peptide synthesis as disclosed by Lu et al (1981) *J. Org. Chem.* 46, 3433 and references therein. Temporary N-amino group protection is afforded by the 9-fluorenylmethyloxycarbonyl (Fmoc) group. Repetitive cleavage of this highly base-labile protecting group is effected using 20% piperidine in N,N-dimethyl-formamide. Side-chain functionalities may be protected as their butyl ethers (in the case of serine threonine and tyrosine), butyl esters (in the case of glutamic acid and aspartic acid), butyloxycarbonyl derivative (in the case of lysine and histidine), trityl derivative (in the case of cysteine) and 4-methoxy-2,3,6-trimethylbenzenesulphonyl derivative (in the case of arginine). Where glutamine or asparagine are C-terminal residues, use is made of the 4,4'-dimethoxybenzhydryl group for protection of the side chain amido functionalities. The solid-phase support is based on a polydimethyl-acrylamide polymer constituted from the three monomers dimethylacrylamide (backbone-monomer), bisacryloylethylene diamine (cross linker) and acryloylsarcosine methyl ester (functionalising agent). The peptide-to-resin cleavable linked agent used is the acid-labile 4-hydroxymethyl-phenoxyacetic acid derivative. All amino acid derivatives are added as their preformed symmetrical anhydride derivatives with the exception of asparagine and glutamine, which are added using a reversed N,N-dicyclohexyl-carbodiimide/1-hydroxybenzotriazole mediated coupling procedure. All coupling and deprotection reactions are monitored using ninhydrin, trinitrobenzene sulphonic acid or isotin test procedures. Upon completion of synthesis, peptides are cleaved from the resin support with concomitant removal of side-chain protecting groups by treatment with 95% trifluoroacetic acid containing a 50% scavenger mix. Scavengers commonly used are ethanedithiol, phenol, anisole and water, the exact choice depending on the constituent amino acids of the peptide being synthesised. Trifluoroacetic acid is removed by evaporation in vacuo, with subsequent trituration with diethyl ether affording the crude peptide. Any scavengers present are removed by a simple extraction procedure which on lyophilisation of the aqueous phase affords the crude peptide free of scavengers. Reagents for peptide synthesis are generally available from Calbiochem-Novabiochem (UK) Ltd, Nottingham NG7 2QJ, UK. Purification may be effected by any one, or a combination of, techniques such as size exclusion chromatography, ion-exchange chromatography and (principally) reverse-phase high performance liquid chromatography. Analysis of peptides may be carried out using thin layer chromatography, reverse-phase high performance liquid chromatography, amino-acid analysis after acid hydrolysis and by fast atom bombardment (FAB) mass spectrometric analysis.

As an alternative to solid phase peptide synthesis techniques, peptides may also be produced by recombinant protein expression or in vitro translation systems (Sambrook et al, "Molecular cloning: A laboratory manual", 2001, $3^{rd}$ edition, Cold Spring Harbor Laboratory Press, Cold Spring Harbor, N.Y.). Of course, it is only peptides which contain naturally occurring amino acid residues joined by naturally-occurring peptide bonds which are encodable by a polynucleotide. Such methods are preferred over solid phase peptide synthesis techniques where the peptide is particularly large, such as larger than 50 amino acids, or larger than 100 amino acids. Recombinant peptides may be subjected to deimination in vitro with the enzyme peptide arginine deiminase to convert the arginine side chain in the polypeptide as defined in relation to the first aspect of the invention to citrulline. This process also converts other arginines present in the peptide to citrulline. Citrullinated peptides may be made by recombinant methods, in which the host organism expresses functional PAD. Synthetic peptides may also be deiminated in vitro, or can be generated with citrulline de novo.

A second aspect of the invention provides a use of a citrullinated enolase peptide with an amino acid sequence comprising or consisting of the amino acid sequence of a region of human α-enolase consisting of five to 150 amino acids encompassing amino acids 14 to 16 of human α-enolase in which amino acid 15 is citrulline or an analogue thereof; or a variant thereof in the manufacture of an agent for aiding in diagnosing rheumatoid arthritis, aiding in distinguishing between different types or stages of rheumatoid arthritis, aiding in prognosing rheumatoid arthritis, aiding in identifying an individual at risk of developing rheumatoid arthritis, treating rheumatoid arthritis, preventing or delaying onset of rheumatoid arthritis, or monitoring efficacy of a treatment regime in an individual being treated for rheumatoid arthritis.

Each of the above options for the use of the agent relate to methods of using the citrullinated enolase peptide as described below.

A third aspect of the invention provides a method of aiding in diagnosing rheumatoid arthritis in an individual comprising exposing a citrullinated enolase peptide with an amino acid sequence comprising or consisting of the amino acid sequence of a region of human α-enolase consisting of five to 150 amino acids encompassing amino acids 14 to 16 of human α-enolase in which amino acid 15 is citrulline or an analogue thereof; or a variant thereof, to a sample from said individual and detecting antibody which has bound to the peptide.

The inventors have identified that the citrullinated enolase peptide defined in relation to the first aspect of the invention has surprising serological properties, which allow it to be used in a method of aiding in diagnosing rheumatoid arthritis. In particular, by testing serum samples from patients with rheumatoid arthritis, disease control patients and healthy individuals for reactivity against Peptide 1A; as described in Example 1, Peptide 1A was found to have a sensitivity of nearly 40% for rheumatoid arthritis and a specificity of 97%. Peptide 1A is a cyclic peptide based on Peptide 1, having the sequence CKIHAXEIFDSXGNPTVEC (SEQ ID NO. 9), where X is citrulline. "Sensitivity" is the percentage of individuals known to have the disease scored as positive for antibody which can bind to the peptide. "Specificity" is the percentage of individuals not having the disease scored as negative for antibody which can bind to the peptide. It is surprising that the presence of antibodies reactive with Peptide 1A is so specific for rheumatoid arthritis, as antibodies reactive with enolase have been detected in many different diseases (Pancholi 2001(supra)). Anti-α-enolase antibodies were detected in 27% of systemic lupus erythromatosus (SLE) patient sera (Pratesi et al (2000) *J Rheumatol* 27:109-115). Surprisingly, antibodies reactive with Peptide 1A were found only at very low frequency in sera from patients with SLE, as shown in Example 2.

The sensitivity of Peptide 1A for rheumatoid arthritis is likely to vary depending on the patient group tested. It is envisaged that the method of this aspect of the invention, which, as is apparent, is intended to determine whether the individual has antibodies reactive with the region of human α-enolase consisting of five to 150 amino acids encompassing amino acids 14 to 16 of human α-enolase in which amino acid 15 is citrulline or an analogue thereof; or a variant thereof, may be complemented by other diagnostic tests, such as tests for rheumatoid factor and tests for antibodies to cyclic citrullinated peptides (ccp), for examples, tests disclosed in Rantapaa-Dahlqvist S et al (2003) *Arthritis Rheum.* 48(10): 2741-9 or WO 03/050542 (supra) or WO 01/46222 to Innogenetics N. V. et al. Combining tests may increase the sensitivity for diagnosing rheumatoid arthritis. It is known, for example, that not all rheumatoid arthritis patients are positive for antibodies to ccp. As described in Example 3, the percentage of rheumatoid arthritis patients scored negative for antibodies to ccp was 19.8%. Even though this group of patients were negative for ccp, a proportion of them (17%) were positive for antibodies to Peptide 1A, and so the presence of antibodies to Peptide 1A can assist in the diagnosis of rheumatoid arthritis in this subset of patients.

Numerous techniques are known in the art to detect antibody which has bound to a peptide. Immunoassays are particularly appropriate for obtaining a quantitative estimate of antibody. Western blotting provides a semi-quantitative estimate.

Immunoassays can be competitive or noncompetitive. In a typical competitive immunoassay, the antibody in the sample competes with labeled antibody to bind with the peptide. The amount of labeled antibody bound to the peptide is then measured. There is an inverse relationship between concentration of antibody in the sample and the quantity of labelled antibody detected. In noncompetitive immunoassays, antibody in the sample is bound to the peptide, then a labeled detection reagent, typically an anti-immunoglobulin antibody, is bound to the antibody. The amount of labeled detection reagent bound to the antibody is then measured. Unlike the competitive method, the results of the noncompetitive method will be directly proportional to the concentration of the antibody.

In a noncompetitive immunoassay or western blot, a labelled detection reagent, typically an anti-immunoglobulin antibody, is used to detect antibody bound to the peptide. A suitable anti-immunoglobulin antibody must bind specifically to immunoglobulin of the species from which the sample is obtained. It may bind to all immunoglobulin isotypes of that species, or only a subset of isotypes. For example, it may bind only to IgA, IgD, IgE, IgG or IgM, or combinations of two or more of these isotypes. The anti-immunoglobulin antibody may bind specifically only to certain subtypes of any given isotype. Subtypes of human IgA are IgA1 and IgA2. The anti-immunoglobulin antibody may bind only to one of these subtypes. Subtypes of human IgG are IgG1, IgG2, IgG3 and IgG4. The anti-immunoglobulin may bind to one or more of these human IgG subtypes. It will be appreciated that there are different isotypes and subtypes in different vertebrate species. Typically, the immunogloubulin isotyope measured in the immunoassays of the invention is IgG and so, typically, the detection reagent is an anti-IgG antibody.

In radioimmunoassay, the antibody or detection reagent is labelled with a radioisotope, such as $^{131}$I or $^{125}$I. In enzyme immunoassays, the antibody or detection reagent is labelled with an enzyme. Suitable enzymes are capable of being detected with the use of a chromogenic substrate. A chromogenic substrate is a substance which, as a result of the reaction with the enzyme, gives rise to a coloured product which can thus be detected spectrophotometrically. Enzymes such as horse radish peroxidase, alkaline phosphatase, beta-galactosidase, and pyrophosphatase from *E. coli* have been widely employed. Chemi-luminescent systems based on enzymes such as luciferase can also be used. Other labels include fluorescent labels such as fluorophores of the Alexa series.

Conjugation of the antibody or detection reagent with the vitamin biotin is frequently used since this can readily be detected by its reaction with enzyme- or fluorophore-linked avidin or streptavidin to which it binds with great specificity and affinity.

In a typical noncompetitive enzyme immunoassay, the sample to be analyzed is placed in contact and incubated with the citrullinated enolase peptide adsorbed on a solid substrate. Any anti-citrullinated enolase peptide antibodies that are possibly present in the sample are thus specifically bound by the peptide adsorbed on the solid substrate, producing a citrullinated enolase peptide/anti-citrullinated enolase peptide antibody complex. The sample is then separated from the solid substrate so as to eliminate non-bound materials, for example, by washing. In the next step of the method, an indicator antibody capable of binding any anti-citrullinated enolase peptide antibodies that are present on the substrate in the form of a citrullinated enolase peptide/anti-citrullinated enolase peptide antibody complex is added to the solid substrate, thus producing a citrullinated enolase peptide/anti-citrullinated enolase peptide antibody/indicator antibody complex. The indicator antibody may, for example, be an anti-human IgG immunoglobulin raised in a non-human animal species. Finally, the presence of the citrullinated enolase peptide/anti-citrullinated enolase peptide antibody/indicator antibody complex on the solid substrate is detected, the presence of said complex on the solid substrate being indicative of the presence of anti-citrullinated enolase peptide antibodies in the sample from the individual.

Typically, the solid substrate is a micro-titration plate, for example, of the type commonly used for performing ELISA immunological assays. The micro-titration plate is preferably a polystyrene plate. Other suitable solid substrates are latex particles, beads and coated red blood cells. Conveniently, the citrullinated enolase peptide is adsorbed to the solid substrate by incubating the peptide in a buffer with the solid substrate. Suitable buffers include carbonate buffer or phosphate buffered saline. Alternatively, the citrullinated enolase peptide may be covalently linked to the solid substrate. Typically, after adsorption or covalent linkage of the citrullinated enolase peptide to the solid substrate, the solid substrate is incubated with a blocking agent to reduce non-specific binding of matter from the sample to the solid substrate. Suitable blocking agents include bovine serum albumin.

It is preferred that a quantitative estimate of antibody which can bind to the citrullinated enolase peptide is obtained by one or more of the above techniques. In typical non-competitive assays, a linear relationship between the measured variable, whether it be optical density or some other read-out, and antibody concentration, is assumed. For example, if sample A has double the optical density of sample B in the assay (background having been subtracted from both), it is assumed that the concentration of antibody is double in A compared to B. However, it is preferable to construct a standard curve of serial dilutions of a pool of positive serum samples. Preferably, such dilutions are assayed at the same time as the test samples. By doing this, any variation from the linear relationship may be taken into account in determining the quantity of antibody in the samples. This provides improved quantitation and reproducibility and is now a standard method for most ELISAs (Venables P J et al (1983) *Arthritis Rheum.* 1983 February; 26(2): 146-55).

Typically, quantitative data are analysed to classify samples as being either positive or negative for the presence of such antibody. A sample having at least a particular quantity, greater or equal to a cut-off value, of citrullinated enolase peptide-binding antibody, is classified as positive. A sample having less than the cut-off value is classified as negative. Suitably, the cut-off value may be defined with reference to the range of concentrations of citrullinated enolase peptide-binding antibody found in a group of samples, particularly a group of control samples obtained from individuals who do not have rheumatoid arthritis. Suitably, values above a particular percentile may be classified as positive. For example, values for control samples above the 95$^{th}$ percentile may be classified as positive. In that case, 5% of control individuals are classified as positive for citrullinated enolase peptide-binding antibody. The concentration of citrullinated enolase peptide-binding antibody in a sample from an individual to be tested is compared against the cut-off value to determine whether that individual is classified as positive or negative for citrullinated enolase peptide-binding antibody. The skilled person will appreciate that other approaches may be used to define the cut-off value for classifying a sample as being positive or negative for citrullinated enolase peptide-binding antibody. For example, the cut-off may be defined by an arbitrarily selected value. It will also be appreciated that concentrations of citrullinated enolase peptide-binding antibody could be categorised into more than two groups. For example, concentrations could be classified as "low", "medium" or "high.

A fourth aspect of the invention provides a method of aiding in distinguishing between different types or stages of rheumatoid arthritis in an individual comprising exposing a citrullinated enolase peptide with an amino acid sequence comprising or consisting of the amino acid sequence of a region of human α-enolase consisting of five to 150 amino acids encompassing amino acids 14 to 16 of human α-enolase in which amino acid 15 is citrulline or an analogue thereof; or a variant thereof, to a sample from said individual and detecting antibody which has bound to the peptide.

The serological properties of the citrullinated enolase peptide as defined in relation to the first aspect of the invention are exploited in the method of the fourth aspect of the invention. The experiments performed by the inventors, as described in the examples, indicate that not all patients suffering from rheumatoid arthritis can be scored as positive for antibody which can bind to the citrullinated enolase peptide. Therefore, testing individuals for the presence or absence of citrullinated enolase peptide-binding antibodies can identify subsets of rheumatoid arthritis. One subset of rheumatoid arthritis patients produce citrullinated enolase peptide-binding antibodies and the other subset does not. Where the test for citrullinated enolase peptide-binding antibodies is complemented with other tests, a more complex diagnostic picture would emerge. For example, as illustrated in Example 3, where rheumatoid arthritis patients are also tested for antibodies which bind in a commercial ELISA to cyclic citrullinated peptides (CCP), patients may be positive for both indicators, negative for both indicators, positive for citrullinated enolase peptide-biding antibodies only, or positive for anti-CCP antibodies only. A suitable anti-CCP test is "Immunoscan RA" (Catalogue No. RA-96RT) from Euro-diagnostica AB, Medeon, SE-205 12 Malmo, Sweden. By combining two tests, patients may accordingly be categorised into four subsets. The outcome of the various tests will be informative in prognosing rheumatoid arthritis and informing clinical decisions relating to treatment regimes.

A fifth aspect of the invention provides a method of aiding in prognosing rheumatoid arthritis in an individual comprising exposing a citrullinated enolase peptide with an amino acid sequence comprising or consisting of the amino acid sequence of a region of human α-enolase consisting of five to 150 amino acids encompassing amino acids 14 to 16 of human α-enolase in which amino acid 15 is citrulline or an analogue thereof; or a variant thereof, to a sample from said individual and detecting antibody which has bound to the peptide.

The serological properties of the citrullinated enolase peptide as defined in relation to the first aspect of the invention are exploited in the method of the fifth aspect of the invention. As discussed in relation to the third aspect of the invention, different types or stages of rheumatoid arthritis may be distinguished by testing individuals for antibodies which bind to the citrullinated enolase peptide. It is considered that determination of the presence of antibodies which bind to the citrullinated enolase peptide are useful in predicting disease progression. Studies can be performed to determine disease progression in a group of patients testing positive for antibodies which bind to the citrullinated enolase peptide, and a group of patients testing negative for antibodies which bind to the citrullinated enolase peptide. In this way, correlations between the presence of the antibodies and disease progression can be identified. This information can then be used in prognosis of new patients presenting with antibodies to the citrullinated enolase peptide. Study designs in which the presence of a predictor is correlated with disease progression are known in the art and have been used, for example, to correlate the presence of antibodies which bind cyclic citrullinated peptides in a commercial test to a more severe and destructive form of rheumatoid arthritis (Forslind et al, *Ann Rheum Dis* 2004. 63: 1090-1095; Jansen et al, *J Rheumatol* 2003. 30: 1691-1695; Kastbom et al, *Ann Rheum Dis* 2004. 63: 1085-1089).

A sixth aspect of the invention provides a method of aiding in identifying an individual at risk of developing rheumatoid arthritis comprising exposing a citrullinated enolase peptide with an amino acid sequence comprising or consisting of the amino acid sequence of a region of human α-enolase consisting of five to 150 amino acids encompassing amino acids 14 to 16 of human α-enolase in which amino acid 15 is citrulline or an analogue thereof; or a variant thereof, to a sample from said individual and detecting antibody which has bound to the peptide.

It is considered that the serological properties of the citrullinated enolase peptide as defined in relation to the first aspect of the invention are useful in the method of the sixth aspect of the invention. As discussed above, and described in the examples, the inventors found that Peptide 1A has a specificity of approximately 97% or 98% for rheumatoid arthritis. In other words, only about 3% or 2% of individuals tested who did not have rheumatoid arthritis were scored as positive for antibodies which can bind to Peptide 1A. These individuals may be at increased risk of developing rheumatoid arthritis, as they have already tested positive for a predictor of the disease. A cohort of individuals not suffering from rheumatoid arthritis but scoring positive for anti-citrullinated enolase peptide antibodies can be studied to determine if they develop rheumatoid arthritis over the course of months or years, as compared to a control group of individuals scoring negative for anti-citrullinated enolase peptide antibodies. Alternatively, retrospective studies may be performed, for example by examining samples collected prior to a person developing RA to identify anti-citrullinated enolase peptide antibodies. Such samples may be available for individuals who have donated blood prior to diagnosis of RA. Such approaches can be used to show that the presence of antibodies against the citrullinated enolase peptide is a risk factor in development of rheumatoid arthritis.

The idea that the presence of antibodies against citrullinated enolase peptide in healthy individuals is a risk factor in development of rheumatoid arthritis is supported by the finding that certain other disease predictors can be detected years before clinical symptoms. In particular, antibodies which bind to cyclic citrullinated peptides in a commercial ELISA have been identified years before clinical symptoms of rheumatoid arthritis (Nielen et al, *Arthritis Rheum* 2004. 50: 380-386; Rantapaa-Dahlqvist et al, *Arthritis Rheum* 2003. 48: 2741-2749). Interestingly, as described in Example 3, there is a correlation between the presence of antibodies to Peptide 1A and positivity in the cyclic citrullinated peptides assay amongst healthy people. 25% of healthy people positive in the ccp assay were also positive for antibodies to Peptide 1A, whereas only 0.8% of healthy people negative in the ccp assay were positive for antibodies to Peptide 1A. This correlation between the presence of antibodies to Peptide 1A and the presence of a known predictor of rheumatoid arthritis suggests that antibodies to Peptide 1A may themselves be predictive of the future development of rheumatoid arthritis among healthy people.

A seventh aspect of the invention provides a method of treating rheumatoid arthritis in an individual comprising:
  (i) exposing a citrullinated enolase peptide with an amino acid sequence comprising or consisting of the amino acid sequence of a region of human α-enolase consisting of five to 150 amino acids encompassing amino acids 14 to 16 of human α-enolase in which amino acid 15 is citrulline or an analogue thereof; or a variant thereof, to a sample from said individual and detecting antibody which has bound to the peptide; and (ii) administering anti-TNF therapy or an antibiotic to said individual.

Preferably, the sample from the individual is found to contain antibody capable of binding to the citrullinated enolase peptide as defined in relation to the first aspect of the invention, in step (i) of the seventh aspect. Anti-TNF therapy may be given in step (ii) of the seventh aspect, typically with methotrexate (Symmons D P M and Silman A J (2006) *Lupus* 15(3): 122-126). Other treatments for RA may also be given, for example treatment with Rituximab.

Preferably, in step (ii) an antibiotic is administered. *Porphyromonas gingivalis*, which can inhabit the human mouth and cause periodontal disease, is the only prokaryote known to express a functional peptidylarginine deaminase (PAD) enzyme (Rosenstein E D et al (2004) *Inflammation* 28(6): 311-8). The inventors have surprisingly found that the amino acid sequence of Peptide 1 shares a high degree of sequence identity with the enolase of *P. gingivalis*. This finding raises the possibility that the antibody response to the citrullinated enolase peptide represents a cross-reactivity of antibodies directed to the *P. gingivalis* enolase, or perhaps another microbial enolase, during infection or colonisation. According to this theory, prevention or treatment of infection or colonisation may cause a prevention or reduction of the production of anti-citrullinated enolase peptide antibodies by the individual and hence an improvement in symptoms of rheumatoid arthritis. Accordingly, administration of an antibiotic according to the seventh aspect of the invention may be an effective treatment of rheumatoid arthritis.

An eighth aspect of the invention provides a method of preventing or delaying onset of rheumatoid arthritis in an individual comprising:

(i) exposing a citrullinated enolase peptide with an amino acid sequence comprising or consisting of the amino acid sequence of a region of human α-enolase consisting of five to 150 amino acids encompassing amino acids 14 to 16 of human α-enolase in which amino acid 15 is citrulline or an analogue thereof; or a variant thereof to a sample from said individual and detecting antibody which has bound to the peptide; and (ii) administering an antibiotic to said individual.

In this aspect, individuals not suffering from rheumatoid arthritis are tested for antibodies which are capable of binding to the citrullinated enolase peptide as defined in relation to the first aspect of the invention. The individual tested may be an individual considered at risk for other reasons, for example family history or genotype, as discussed above. Preferably, an individual scored as positive for such antibodies in step (i) of the method is administered an antibiotic in step (ii). As discussed in relation to the seventh aspect of the invention, administration of an antibiotic is intended to prevent or treat infection or colonisation of the individual with a microbe which can produce a citrullinated enolase having a region sharing a high degree of sequence identity with the citrullinated enolase peptide. According to the theory outlined above, this may cause a prevention or reduction of the production of anti-citrullinated enolase peptide antibodies by the individual, which could have the effect of preventing or delaying onset of rheumatoid arthritis, particularly where the anti-citrullinated enolase peptide contributes to the pathogenesis of rheumatoid arthritis.

Preferably, in the method of the seventh and eight aspects of the invention, the antibiotic is doxycycline. An antibiotic dose of doxycycline may be administered, for example as described in O'Dell et al (Arthritis & Rheumatism (2006) 54:621-627). Preferably, doxycycline is administered with methotrexate (O'Dell et al (supra)).

Preferably, the methods of any of the third to eighth aspects of the invention further comprise exposing a control peptide to a sample from the same individual and detecting antibody which has bound to the control peptide, wherein the control peptide is identical to the citrullinated enolase peptide except that:

(a) the residue corresponding to human α-enolase amino acid 15 is replaced by a residue other than citrulline or an analogue thereof, preferably an arginine residue; and, (b) where the citrullinated enolase peptide comprises a residue corresponding to amino acid 9 of human α-enolase, which residue is citrulline or an analogue thereof, the residue corresponding to amino acid 9 of human α-enolase in the control peptide is citrulline or an analogue thereof, or another residue, preferably an arginine residue.

Preferably, the citrulline (or citrulline analogue) residue corresponding to human α-enolase amino acid 15 is replaced by an arginine residue. Preferably, where the citrullinated enolase peptide comprises a citrulline (or analogue thereof) corresponding to position 9 of human α-enolase, this is replaced by an arginine residue in the control peptide.

The purpose of this further step is to provide an estimate of the quantity of antibody in the sample which binds specifically to the citrullinated enolase peptide, compared to the quantity of antibody which binds to the control peptide which lacks the citrulline residue (or citrulline analogue residue) corresponding to human α-enolase amino acid 15 and, optionally, amino acid 9. The inventors believe that the presence of the citrulline residue corresponding to amino acid 15 is a key determinant which gives rise to the high specificity of Peptides 1A and 1B for rheumatoid arthritis. Therefore, the quantity of antibody which binds only to the peptide having the key citrulline residue may be more relevant for determining whether an individual should be scored as positive or negative for anti-enolase antibody. If all or the majority of antibody binding to the citrullinated enolase peptide also binds to the control peptide, the individual may be scored as negative for antibodies to the citrullinated enolase peptide.

Preferably, where a control peptide is used:

(a) the citrullinated enolase peptide comprises or consists of KIHAXEIFDSXGNPTVE (SEQ ID NO. 7) or a variant thereof and the control peptide comprises or consists of KIHAXEIFDSRGNPTVE (SEQ ID NO. 13) or a variant thereof or KIHAREIFDSRGNPTVE (SEQ ID NO. 14) or a variant thereof, wherein X is citrulline or an analogoue thereof; or, (b) the citrullinated enolase peptide comprises or consists of KIHAREIFDSXGNPTVE (SEQ ID NO. 8) or a variant thereof and the control peptide comprises or consists of KIHAREIFDSRGNPTVE (SEQ ID NO. 14) or a variant thereof, wherein X is citrulline or an analogoue thereof.

Thus, where Peptide 1A is used as the citrullinated enolase peptide, Peptide 1C or Peptide 1D are suitable control peptides. Where Peptide 1B is used as the citrullinated enolase peptide, Peptide 1D is a suitable control peptide.

Preferably, the methods of any of the third to eighth aspects of the invention further comprise testing a sample from the same individual for antibodies which bind to cyclic citrullinated peptides. The commercial anti-CCP2 ELISA test for cyclic citrullinated peptides "Immunoscan RA" (Catalogue No. RA-96RT) available from Euro-diagnostica AB, Medeon, SE-205 12 Malmo, Sweden, and based on WO 03/050542, is considered as particularly complementary to the test for anti-citrullinated enolase peptide antibodies as described herein because, as described in the examples, rheumatoid arthritis patients have been identified who are scored negative in this test but who, nonetheless, are positive for antibodies to the citrullinated enolase peptide.

Preferably, the methods of any of the third to eighth aspects of the invention further comprising exposing the citrullinated enolase peptide to a control sample and detecting antibody which has bound to the peptide. Preferably, the control sample is from one or more individuals not suffering from RA. This test confirms that the citrullinated enolase peptide has a high specificity for rheumatoid arthritis and is not bound non-specifically by antibodies.

Preferably, in the methods of any of the third to eighth aspects of the invention, the individual is a human.

Preferably, in the methods of any of the third to eighth aspects of the invention, the sample from the individual is serum. Other suitable samples include saliva and synovial fluid. Where available, samples of antibodies eluted from tissue samples may be used.

A ninth aspect of the invention provides a method of monitoring efficacy of a treatment regime in an individual being treated for rheumatoid arthritis comprising:
  (i) obtaining a first sample from said individual;
  (ii) obtaining a second sample from said individual after said individual has been subject to the treatment regime for a period of time;
  (iii) providing a citrullinated enolase peptide with an amino acid sequence comprising or consisting of the amino acid sequence of a region of human α-enolase consisting of five to 150 amino acids encompassing amino acids 14 to 16 of human α-enolase in which amino acid 15 is citrulline or an analogue thereof; or a variant thereof
  (iv) exposing said citrullinated enolase peptide to said first sample and detecting antibody which has bound to said peptide; and
  (v) exposing said citrullinated enolase peptide to said second sample and detecting antibody which has bound to said peptide.

The citrullinated enolase peptide and the step of exposing the citrullinated enolase peptide to a sample and detecting antibody which has bound to the peptide are as described above in relation to the third aspect of the invention. However, in this case, rather than one sample, two samples are obtained, the second after the individual has been subject to a treatment regime for a period of time. Preferably, the two samples are of the same type of biological fluid, for example serum, saliva or synovial fluid.

As described in the examples, the inventors have found that anti-citrullinated enolase peptide antibodies can decrease in response to therapy with a combination of anti-TNF and methotrexate. Accordingly, the method of the ninth aspect of the invention allows for the efficacy of the treatment regime to be monitored.

Preferably, the treatment regime comprises anti-TNF therapy (Symmons D P M and Silman A J (2006) *Lupus* 15(3): 122-126 or doxycycline therapy (O'Dell et al (2006) *Arthritis & Rheumatism* 54:621-627). Preferably, anti-TNF or doxycycline are administered with methotrexate.

Preferably, the second sample is obtained up to one month, two months, three months, six months, 1 year or 2 years after the first sample was obtained. It is also envisaged that samples may be obtained at intervals during the treatment regime, such as intervals of up to one month, two months, three months, six months, 1 year or 2 years. The number of samples obtained may be 2, 3, 4, 5, 6, 7, 8, 9, 10, 15, 20, 30 or more.

Preferably, the ninth aspect of the invention further comprises exposing a control peptide to a sample from the same individual collected at substantially the same time as the first sample, and to a sample from the same individual collected at substantially the same time as the second sample, and, for each of the samples, detecting antibody which has bound to the control peptide, wherein the control peptide is identical to the peptide except that:
  (a) the residue corresponding to human α-enolase amino acid 15 is replaced by a residue other than citrulline or an analogue thereof, preferably an arginine residue; and,
  (b) where the citrullinated enolase peptide comprises a residue corresponding to amino acid 9 of human α-enolase, which residue is citrulline or an analogue thereof, the residue corresponding to amino acid 9 of human α-enolase in the control peptide is citrulline or an analogue thereof, or another residue, preferably an arginine residue.

Preferably, the citrulline (or citrulline analogue) residue corresponding to human α-enolase amino acid 15 is replaced by an arginine residue. Preferably, where the citrullinated enolase peptide comprises a citrulline (or analogue thereof) corresponding to position 9 of human α-enolase, this is replaced by an arginine residue in the control peptide.

The rationale for performing this further step is as described above.

Preferably, where a control peptide is used:
(a) the citrullinated enolase peptide comprises or consists of KIHAXEIFDSXGNPTVE (SEQ ID NO. 7) or a variant thereof and the control peptide comprises or consists of KIHAXEIFDSRGNPTVE (SEQ ID NO. 13) or a variant thereof or KIHAREIFDSRGNPTVE (SEQ ID NO. 14) or a variant thereof, wherein X is citrulline or an analogoue thereof; or,
(b) the citrullinated enolase peptide comprises or consists of KIHAREIFDSXGNPTVE (SEQ ID NO. 8) or a variant thereof and the control peptide comprises or consists of KIHAREIFDSRGNPTVE (SEQ ID NO. 14) or a variant thereof, wherein X is citrulline or an analogoue thereof.

Thus, where Peptide 1A is used as the citrullinated enolase peptide, Peptide 1C or Peptide 1D are suitable control peptides. Where Peptide 1B is used as the citrullinated enolase peptide, Peptide 1D is a suitable control peptide.

Preferably, in the method of the ninth aspect of the invention, the individual is a human.

Preferably, in the method of the ninth aspect of the invention, the sample is serum.

A tenth aspect of the invention provides a method of treating an individual with rheumatoid arthritis comprising:
  (i) providing a citrullinated enolase peptide with an amino acid sequence comprising or consisting of the amino acid sequence of a region of human α-enolase consisting of five to 150 amino acids encompassing amino acids 14 to 16 of human α-enolase in which amino acid 15 is citrulline or an analogue thereof; or a variant thereof, which peptide is immobilised to a support; and
  (ii) performing immunoapheresis with the peptide immobilised to the support.

An eleventh aspect of the invention provides a use of a citrullinated enolase peptide with an amino acid sequence comprising or consisting of the amino acid sequence of a region of human α-enolase consisting of five to 150 amino acids encompassing amino acids 14 to 16 of human α-enolase in which amino acid 15 is citrulline or an analogue thereof; or a variant thereof in the manufacture of an agent for performing immunoapheresis to treat an individual with rheumatoid arthritis wherein the agent comprises the peptide immobilised to a support, and immunoapheresis is performed with the peptide immobilised to the support.

The purpose of the tenth and eleventh aspects of the invention is to remove antibodies which can bind to citrullinated enolase peptides from an individual with rheumatoid arthritis. This is expected to be of therapeutic benefit where the antibodies contribute to the pathogenesis of the disease and has been used successfully in treatment of autoimmune diseases. For example, Eming R & Hertl M (Immunoadsorption in pemphigus. (2006) *Autoimmunity*. November; 39(7):609-16) describe treatment of a patient for pemphigus (a serious blistering skin disease) by extracorporeal immunosorption of pathogenic autoantibodies which bound to the autoantigen immobilized on the adsorber. The techniques described in Eming R & Hertl M (supra) could be adapted by the skilled person to perform the tenth and eleventh aspects of the invention.

Preferably in the methods or uses of the first to tenth aspects of the invention, the peptide is a cyclic peptide. Cyclisation of a citrullinated peptide has been shown to increase its sensitivity in an RA test, without loss of specificity for RA (Schellekens G A et al (2000) *Arthritis Rheum.* 43(1):155-63). It is thought that cyclisation may constrain a peptide to conformations that favour antibody binding. Cyclisation may also improve the adsorption of the peptide to a solid substrate, as required in certain immunoassay techniques as described above. Suitably, and as described in Schellekens et al (supra), cyclisation can be achieved by forming a cysteine bridge between a pair of cysteine residues. Where conveniently placed cysteine residues are not present in the peptide, they may be inserted or may be included as substitutes for one or more other amino acids. Conveniently, the pair of cysteine residues may be located at the N- and C-termini of the peptide, although in an alternative arrangement, one or both of the cysteines may be present in the body of the peptide. Cysteine bridge formation may be effected by oxidation, such as iodine/methanol oxidation.

Preferably in the methods or uses of the first to tenth aspects of the invention, the citrullinated enolase peptide comprises or consists of KIHAXEIFDSXGNPTVE (SEQ ID NO. 7) or KIHAREIFDSXGNPTVE (SEQ ID NO. 8) or a variant thereof wherein X is citrulline or an analogoue thereof. Preferably, the citrullinated enolase peptide is a cyclic peptide.

Preferably, the citrullinated enolase peptide comprises or consists of CKIHAXEIFDSXGNPTVEC (SEQ ID NO. 9) or CKIHAREIFDSXGNPTVEC (SEQ ID NO. 10) wherein X is citrulline or an analogoue thereof.

Variants of the citrullinated enolase peptide are as defined in relation the first aspect of the invention.

An eleventh aspect of the invention provides a citrullinated enolase peptide with an amino acid sequence comprising or consisting of the amino acid sequence of a region of human α-enolase consisting of five to 150 amino acids encompassing amino acids 14 to 16 of human α-enolase in which amino acid 15 is citrulline or an analogue thereof; or a variant thereof wherein the peptide does not consist of IHAXEEIFDSXGNPTVEVDLFTSK (SEQ ID NO. 15).

Suitable citrullinated enolase peptides are as described above in relation to the first aspect of the invention. Variants of the citrullinated enolase peptide are as defined in relation the first aspect of the invention.

Preferably, the citrullinated enolase peptide of the eleventh aspect comprises or consists of KIHAXEIFDSXGNPTVE (SEQ ID NO. 7) or KIHAREIFDSXGNPTVE (SEQ ID NO. 8) or a variant thereof wherein X is citrulline or an analogoue thereof.

Preferably, the citrullinated enolase peptide of the eleventh aspect comprises or consists of CKIHAXEIFDSXGNPTVEC (SEQ ID NO. 9) or CKIHAREIFDSXGNPTVEC (SEQ ID NO. 10) wherein X is citrulline or an analogoue thereof.

Preferably, the citrullinated enolase peptide of the eleventh aspect is a cyclic peptide.

A twelfth aspect of the invention provides a control peptide which is identical to the citrullinated enolase peptide of the eleventh aspect except that:
(a) the citrulline (or citrulline analogue) residue corresponding to human α-enolase amino acid 15 is replaced by a different residue, preferably an arginine residue; and,
(b) where the citrullinated enolase peptide comprises a residue corresponding to amino acid 9 of human α-enolase, which residue is citrulline or an analogue thereof, the residue corresponding to amino acid 9 of human α-enolase in the control peptide is citrulline or an analogue thereof, or another residue, preferably an arginine residue.

Preferably, the control peptide is a cyclic peptide.

Variants of the control peptide are as defined in relation to the first aspect of the invention, with the exception that the control peptide does not have the same sensitivity for RA in an assay as does the corresponding citrullinated enolase peptide. On the contrary, the control peptide has a much lower sensitivity for RA. It may have a higher or equal specificity for RA, in that a higher or equal proportion of samples from healthy donors may be negative for binding to the control peptide compared to the corresponding citrullinated enolase peptide. In some instances, it may have a lower specificity for RA.

A thirteenth aspect of the invention provides a kit of parts comprising:
(i) the peptide as defined in any of the first to eleventh aspects of the invention, and
(ii) a reagent which binds to an antibody.

The reagent may be a detection reagent as described in relation to the third aspect of the invention, which binds to the antibody, and which allows detection of the antibody bound to the peptide in an assay such as has already been described. A suitable detection reagent is an anti-immunoglobulin antibody, as described above.

Preferably, the kit of the thirteenth aspect also comprises a control peptide as defined in the twelfth aspect. Suitably, the control peptide is identical to the citrullinated enolase peptide provided in the kit, except that:
(a) the citrulline (or citrulline analogue) residue corresponding to human α-enolase amino acid 15 is replaced by a different residue, preferably an arginine residue; and,
(b) where the citrullinated enolase peptide comprises a residue corresponding to amino acid 9 of human α-enolase, which residue is citrulline or an analogue thereof, the residue corresponding to amino acid 9 of human α-enolase in the control peptide is citrulline or an analogue thereof, or another residue, preferably an arginine residue.

FIG. 1

IgG responses to citrullinated α-enolase peptides in A RA patients (n=102); B non-RA patient controls (n=92), and; C healthy controls C (n=92). RA patients have a stronger IgG response to citrullinated α-enolase peptides than either control group. IgG was measured by ELISA and data presented as peptide OD450 with the background (carbonate buffer) OD450 subtracted. One dot represents one individual for each of the nine citrullinated α-enolase peptides. Horizontal lines indicate mean OD450 for the individual peptides.

FIG. 2

Percentage of positive individuals (y-axis) for antibodies to each of the nine citrullinated α-enolase peptides (x-axis). Data for RA patients are represented by black columns, non-RA patients by grey columns and healthy controls by white columns A larger percentage of RA-patients have antibodies to citrullinated α-enolase peptides, than do non-RA patients and healthy controls. Antibodies to the immunodominant peptide 1A were detected in 37.3% of the RA-patients, but only in 4.3% and 2.2% of the controls respectively, resulting in a specificity of 97%. Data were generated by ELISA using sera from 102 RA patients, 92 non-RA patient controls and 92 healthy controls.

FIG. 3

RA patient sera were tested for antibodies to each of Peptides 1A to 1D. A Percentage of RA patient sera scored as positive for antibodies to each of Peptides 1A to 1D. B Quantity of IgG in patient sera reactive with each of Peptides 1A to 1D, reflected by OD450 in ELISA. Horizontal bars indicate mean OD450 for each peptide. *P<0.0001; P<0.01. The antibody response observed towards the immunodominant Peptide 1A, is dependent on the presence of citrulline, demonstrated here by the low number of RA patients positive for antibodies to the control Peptide 1D and by the low IgG-levels recorded towards this peptide. It is the second citrulline residue, rather than the first, that generates the high sensitivity and IgG levels, for this B-cell epitope (compare Peptides 1B and 1C).

FIG. 4

RA-patients treated with a combination of methotrexate (MTX) and Infliximab (INF) (n=11) had a significant decrease in DAS28 (CRP and ESR) 6, 18 and 52 weeks post treatment (A and B), *P<0.05 (6 and 18 weeks) and **P<0.01 (52 weeks). MTX alone (n=13), however, did not result in such statistically significant decrease, not for DAS28 (CRP) nor for DAS28 (ESR) (C and D). DAS28 (CRP and ESR) were assessed, by a rheumatologist, pre-treatment as well as 6, 18 and 52 weeks post treatment. The horizontal bars indicate mean CRP and ESR at the different time points.

FIG. 5

A Anti-Peptide 1A antibody levels decreased over time in RA patients treated with MTX+INF (n=11). B Anti-Peptide 1A antibody levels increased in patients treated with MTX alone (n=13). Data did not reach statistical significance at any time point investigated. Sera were collected pre-treatment, as well as 6, 18 and 52 weeks post treatment. IgG was measured by ELISA and presented as OD450(peptide)-OD450(carbonate buffer). The horizontal bars indicate mean OD450 at the different time points. Methotrexate=MTX; Infliximab=INF.

FIG. 6

IgG responses to citrullinated Peptide 1A (black circles) and to the arginine containing control Peptide 1D (white circles) were measured by ELISA for various dilutions of A rabbit anti-Peptide 1A antisera or B affinity purified human anti-Peptide 1A antisera. A high degree of specificity for Peptide 1A compared to Peptide 1D was demonstrated for the rabbit polyclonal antibody, **P<0.01, while cross-reactivity with the control Peptide 1D was observed for the affinity purified human immunoglobulins. Data are presented as OD450 (peptide)-OD450 (background).

FIG. 7

Detection of enolases using rabbit polyclonal antibody in a western blot. Rabbit polyclonal anti-Peptide 1A antibodies bound a protein of around 50 kD in PAD-treated *Streptococcus pyogenes* lysates (lane 1), but not in untreated bacterial lysates (lane 2). α-enolase treated with PAD was used as a positive control (lane 3), while untreated α-enolase served as a negative control (lane 4). Molecular weights (kDa) are indicated at the left of the panel.

FIG. 8

A OD450 values (after subtraction of background) of sera samples of each of 29 SLE patients in ELISA for quantification of antibody to each of Peptides 1A, 1B, 1D and 2 to 9. Results of each patient are represented by a different symbol, but for most peptides, the symbols overlap. B Percentage of SLE patients scored positive for antibodies to each of Peptides 1A, 1B, 1D and 2 to 9, any of these peptides (any cit-eno pep) or a commercially available anti-cyclic citrullinated peptides assay (CCP).

FIG. 9

RA-patients (n=102) (A) have a stronger IgG response to citrullinated α-enolase peptides than disease controls (n=110) (B) and healthy controls (C) (n=92). IgG was measured by ELISA and data presented as peptide $OD_{450}$ with the background (carbonate buffer) $OD_{450}$ subtracted. One dot represents the reactivity of one serum sample with each of the eleven citrullinated α-enolase peptides. The grey lines indicate mean $OD_{450}$ for the antibody response to the individual peptides. nd=not done.

FIG. 10

The antibody response to the immunodominant peptide 1 is dependent on the presence of citrulline, demonstrated here by the low IgG-levels recorded towards the arginine-containing control peptide 1D, *P<0.0001. It is the second citrulline residue, rather than the first, that generates the high IgG levels for this B cell epitope (compare peptide 1B and 1C), P<0.01. Data was generated by ELISA on sera from 102 RA patients and presented as $OD_{450}$ (peptide)-$OD_{450}$ (background).

FIG. 11

A strong anti-CEP-1 antibody response was also found in the US RA cohort. 62% of patients (n=81) had anti-CEP-1 antibodies compared to 2% of healthy controls (n=82). Data was generated by ELISA and presented as $OD_{450}$ (peptide)-$OD_{450}$ background. The dotted line indicates the cut-off value for positive samples, based on the 98$^{th}$ percentile of controls.

FIG. 12

Anti-CEP-1 antibodies do not cross-react with other citrullinated α-enolase epitopes. A dose dependent decrease in binding to CEP-1-coated plates was seen in six anti-CEP-1 positive RA serum samples pre-incubated with increasing concentrations of CEP-1 (A), while pre-incubation with the control peptide 1D (B), peptide 4 (C), peptide 9 (D) or peptide 11 (E) did not result in decreased antibody binding. Sera were pre-incubated in liquid phase with increasing concentrations (0, 1, 10 and 100 µg/ml) of peptides before transferred to CEP-1-coated ELISA plates. Data are presented as $OD_{450}$ for each of the peptide concentrations.

FIG. 13

RA patients have anti-CEP-1-specific as well as CCP-cross-reactive anti-CEP-1 antibodies. Individual sera exhibited differing degrees of cross-reactivity, as demonstrated by a reduction in antibody binding that ranged between 0 and 53%, following pre-incubation with CCP (grey bars). Sera from nine double positive (anti-CEP-1 positive and anti-CCP positive) RA patients were pre-absorbed on CEP-1- or CCP-coated plates before transferred to CEP-1-coated plates. Results are expressed as the percentage of maximum inhibition, which by definition was set to 100% for pre-incubation with CEP-1 (black bars).

FIG. 14

RA patients have antibodies to the *P. gingivalis* version of CEP-1. Fifty four percent of rheumatoid patients were positive for anti-*P. gingivalis* CEP-1 antibodies (black circles) in comparison to 2% of healthy controls (grey diamonds). The antibody response to *P. gingivalis* CEP-1 (y-axis) correlates strongly with the antibody response to the human version of this peptide (x-axis) ($r^2$=0.803, p<0.0001). IgG was measured by ELISA in serum from 81 RA patients and 82 healthy controls. Data are presented as $OD_{450}$.

FIG. 15

Specificity of affinity purified rabbit and human antibodies for the immunodominant epitope CEP-1. A high degree of CEP-1-specificity was demonstrated for the rabbit polyclonal antibody (A), **P<0.01, while cross-reactivity with the control peptide was observed for the affinity purified human immunoglobulins (B). IgG responses to CEP-1 (peptide 1A) (black circles) and to the arginine containing control peptide (peptide 1D) (white circles) was measured in serial dilutions by ELISA. Data are presented as $OD_{450}$ (peptide)-$OD_{450}$ (background).

FIG. 16

Anti-CEP-1 antibodies cross-react with bacterial enolase. Rabbit polyclonal anti-CEP-1 antibodies (A) as well as anti-CEP-1 antibodies purified from an RA patient (B), bound a protein of around 50 kDa in the PAD-treated (lane 1) and in the untreated (lane 2) *P. gingivalis* lysates. Bacterial enolase was demonstrated in both lane 1 and 2 (C). Presence of citrullinated proteins was also detected in both *P. gingivalis* lysates (D). *S. pyogenes* lysates treated with PAD was bound by the rabbit anti-CEP-1 antibody (lane 5), whilst the untreated lysate (lane 6) was not (E). Citrullinated proteins were present in the PAD-treated *S. pyogenes* lysate (lane 5), but not in the untreated lysate (lane 6) (F). Citrullinated α-enolase (lanes 3 and 7) and uncitrullinated α-enolase (lanes 4 and 8) served as controls. Proteins were separated on SDS-PAGE gels and blotted with affinity purified rabbit or human anti-CEP-1 antibodies, a rabbit anti-enolase antibody or an anti-citrulline (modified) detection kit. nd=not done.

FIG. 17

Antibody response to CEP-1 in a Swedish cohort. Rheumatoid arthritis patients (RA) and healthy controls (contr) were assigned to ccp+ or ccp– groups according to the reactivity of their sera in the commercial CCP ELISA, thus providing four groups: ccp+ RA, ccp– RA, ccp– contr and ccp+ contr. Reactivities of sera in the assay for CEP-1 were determined Data are presented as Arbitrary Units (AU), that were calculated based on a standard curve of a pool of strongly anti-CEP-1 positive RA sera, which was given an AU of 10 000. Each dot represents the reactivity of one serum sample. The grey lines indicate the mean for each group. Data points above the cut-off value are considered positive for antibodies to CEP-1.

EXAMPLE 1

Introduction

Rheumatoid arthritis (RA) is a chronic, inflammatory joint disorder which is considered to be autoimmune, although the autoantigens which trigger and sustain the immune response remain unknown. In the last 10 years it has emerged that an essential feature of many disease-specific autoantigens in RA is the post-translational conversion of peptidylarginine to peptidyl citrulline. Anti-citrullinated protein autoantibodies (ACPA), are highly specific (98%) and sensitive (up to 80%) [1, 2] for RA, making citrullinated proteins strong candidates for driving the autoimmune response in this disease (reviewed in [3]). Kuhn et al, for example, have recently demonstrated that administration of anti-citrullinated fibrinogen antibodies enhanced disease severity in an experimental mouse model of arthritis (4). A number of studies have established that ACPA can be detected years before clinical symptoms [5, 6] and are associated with a more severe and destructive form of the disease [7-16], demonstrating their importance as diagnostic as well as prognostic markers. In the majority of patients, the presence of ACPA antedates disease onset (5, 6), and ACPA positive patients present with a more severe and erosive form of arthritis (7-16).

A commercial ELISA based on cyclic citrullinated peptides (CCP) detects ACPA and is now routinely used in the diagnosis of RA. Little is, however, known about the origin of this antibody response.

There are many situations where proteins are citrullinated in health and in disease, in the absence of an antibody response. Citrullinated proteins are present in all healthy individuals in the skin, the hair follicles and the myelin sheaths of nerve fibres. In addition, abnormal accumulation of citrullinated proteins have been described at sites of inflammation, including the joints of patients with all forms of arthritis [17], the brain of patients suffering from multiple sclerosis [18] or Alzheimer's disease [19] and in the muscle fibres of patients with myositis [20]. Hence, Citrullinated proteins are present in health and disease, while tolerance to citrullinated proteins appears to be selectively lost in patients with RA. Thus, in RA, it is the antibody response rather than the expression of antigen, which is specific to the disease.

RA is a complex and heterogeneous disease, where genes and environment are likely to interact in the development of pathology. Recent studies have demonstrated that the HLA-DRB1 shared epitope alleles (HLA-SE), the best known genetic risk factor for RA, are only associated with (anti-)CCP positive RA, not (anti-)CCP negative RA, indicating that HLA-SE may be a specific risk factor for the production of ACPA, rather than the disease itself [21, 22]. Furthermore, a strong gene-environment interaction between HLA-SE and the well established environmental risk factor cigarette smoking, is present in (anti-) CCP positive patients but not in (anti-)CCP negative patients [21] [23]. Other environmental factors proposed as implicated in the pathogenesis of RA, are infections, both bacterial and viral [24-27], though, to date, no single organism has survied as a compelling candidate for the aetiology of the disease. One theory has been that antigens from infectious agents are similar to host antigens and through molecular mimicry [30], the pathogen-specific immune response cross-reacts with self proteins and causes autoimmune disease. Interestingly, one pathogen, *Porphyromonas gingivalis*, expresses the citrullinating enzyme peptidylarginine deiminase (PAD) [28]. Thus, infections could give rise to citrullination of host proteins or of bacterial proteins, either by activation of host PAD or bacterial PAD. Tolerance to these modified proteins could then be broken in the presence of danger signals delivered by the pathogen. Infectious agents might therefore be involved in the generation of ACPA and the development of RA.

It is not clear which proteins harbour the epitopes targeted by ACPA, although we have recently identified α-enolase as a candidate [29]. Alpha-enolase is abundantly expressed in the rheumatoid synovial membrane and antibodies targeting only the citrullinated form of the molecule are specific for the disease. The molecule is also highly conserved throughout eukaryotes and prokaryotes, and could therefore be a candidate for molecular mimicry between bacterial and host proteins [30]. In the present study we have mapped the epitope of this anti-citrullinated α-enolase antibody response, using a number of citrullinated α-enolase peptides. We have identified a major B cell epitope, which shows high sequence similarity to bacterial enolase. We have also demonstrated that affinity purified antibodies, specific for the immunodominant epitope on citrullinated α-enolase, cross-reacts with bacterial enolase, suggesting that autoimmunity in the subset of RA-patients who have antibodies to citrullinated α-enolase could be primed by bacterial infection.

Materials and Methods
Patient Samples

Serum samples were obtained with informed consent and ethical approval from 102 patients with RA and 92 (or 110 patients for the results generally shown in FIGS. 9 to 16) patients with other arthritidies (including systemic lupus erythematosus (n=32), Sjogrens syndrome (n=31), psoriatic arthritis (n=5), Behçet's syndrome (n=18; FIGS. 9 to 16) and miscellaneous other rheumatic diseases (n=24). 92 control serum samples were obtained from healthy volunteers. An additional cohort of 24 patients with RA undergoing treatment with either methotrexate (MTX) alone (n=13) or methotrexate in combination with Infliximab (INF) (n=11) [28] were collected before treatment as well as 6, 18 and 52 weeks post treatment. Disease activity score (DAS 28), erythrocyte sedimentation rate (ESR) and C-reactive protein (CRP) were measured for each patient at the same time points, i.e. 0, 6, 18 an 52 weeks post treatment. All patients attended the Rheumatology Clinic at Charing Cross Hospital, London. An independent cohort from the US included serum samples from 81 RA patients, taken at baseline in a clinical trial at the Omaha Veterans Affairs Medical Centre, University of Nebraska, USA, and 82 serum samples from healthy volunteers. All RA patients met the American College of Rheumatology (ACR) classification criteria (43).

Peptides

Fifteen cyclic 15 to 23-mer peptides were synthesised at Cambridge Research Biochemicals (Cleveland, UK). The peptide sequences corresponded to amino acid sequences in human α-enolase (SwissProt accession number P06733) or *P. gingivalis* enolase (SwissProt accession number AAQ66821), with the addition of cysteine residues at the amino- and carboxy-termini and the exchange of citrulline for arginine residues at certain positions, as shown in Tablet and Table 2 below.

TABLE 1

Peptides used in this Example

| Peptide name | Corresponding amino acids in human α-enolase | Peptide sequence |
|---|---|---|
| 1A (CEP-1) | 5-21 | ckiha-X-eifds-X-gnptvec (SEQ ID NO: 9) |
| 1A *P. gingivalis* | 5-21 | ckiig-X-eilds-X-gnptvec (SEQ ID NO: 16) |
| 1B | 5-21 | ckiha-R-eifds-X-gnptvec (SEQ ID NO: 10) |
| 1C | 5-21 | ckiha-X-eifds-R-gnptvec (SEQ ID NO: 11) |
| 1D | 5-21 | ckiha-R-eifds-R-gnptvec (SEQ ID NO: 12) |
| 2 | 22-38 | cvdlftskglf-X-aavpsgc (SEQ ID NO: 17) |

TABLE 1-continued

Peptides used in this Example

| Peptide name | Corresponding amino acids in human α-enolase | Peptide sequence |
|---|---|---|
| 3 | 44-64 | cyealel-X-dndkt-X-ymgkgvskc (SEQ ID NO: 18) |
| 4 | 125-142 | cekgvply-X-hiadlagnsec (SEQ ID NO: 19) |
| 5 | 177-194 | cnf-X-eam-X-igaevyhnlknc (SEQ ID NO: 20) |
| 6 | 252-270 | cf-X-sgkydldfkspddps-X-yc (SEQ ID NO: 21) |
| 7 | 362-379 | cangwgvmvsh-X-sgetedtc (SEQ ID NO: 22) |
| 8 | 405-421 | cakynqll-X-ieeelgskac (SEQ ID NO: 23) |
| 9 | 422-434 | ckfag-X-nf-X-nplakc (SEQ ID NO: 24) |
| 10 | 313-331 | ciqvvgddltvtnpk-X-iakac (SEQ ID NO: 25) |
| 11 | 324-341 | cnpk-X-iakavnekscncllc (SEQ ID NO: 26) |

The names (column 1), the corresponding amino acids in human α-enolase (column 2) and the sequences (column 3) of the 15 cyclic peptides (1A, 1B, 1C, 1D, 2-9) used in this study. X = citrulline. Table 1

ELISA 96-well plates (Maxisorp; Nunc, Roskilde, Denmark) were coated with α-enolase peptides at 10 μg/ml (diluted in a 50 mM carbonate buffer, pH 9.6), or with carbonate buffer alone, and incubated over night at 4° C. Wells were washed with PBS-Tween (0.05%) and blocked with 2% BSA (diluted in PBS) for 3 hours at room temperature. Sera were diluted 1:50 in RIA-buffer (10 mM Tris, 1% BSA, 350 mM NaCl, 1% Triton-X, 0.5% Na-deoxychlate, 0.1% SDS) supplemented with 10% FCS, added in duplicates and incubated for 1.5 hour at room temperature. Plates were washed as described above and incubated with peroxidase-conjugated mouse anti-human IgG (Hybridoma Reagent Laboratory, Baltimore, USA) (diluted 1:1000 in RIA-buffer, 10% FCS) for 1 hour at room temperature. After a final wash (PBS-Tween, 0.05%), bound antibodies were detected with TMB substrate (KPL, Maryland, USA). The reaction was stopped by the addition of 1M $H_2SO_4$ and absorbance measured at 450 nm in a Multiscan Ascent microplate reader (Thermo Labsystems). A control serum was included on all plates to correct for plate-to-plate variation. Background $OD_{450}$ (wells coated with only carbonate buffer) was subtracted from peptide $OD_{450}$ for every serum tested. Values above 0.1 were taken as positive. ELISA on the US serum samples were performed in a similar manner, but with 2% BSA in carbonate buffer as background, and with an OD cut-off of 0.2 for positive samples. Anti-CCP antibody status was analysed using the CCP2 kit (Eurodiagnostica, Malmo, Sweden), according to the manufacturer's instructions.

Inhibition Assays

Inhibition experiments were performed in liquid phase on six anti-CEP-1 positive RA serum samples or on solid phase using serum from nine double positive (anti-CEP-1 and CCP positive) RA patients. Sera were either pre-incubated for 2 hours in RIA-buffer containing increasing concentrations (0, 1, 10 and 100 µg/ml) of CEP-1, control peptide 1D, peptide 4, peptide 7, peptide 9 or peptide 11, or pre-absorbed on plates coated with CEP-1, carbonate buffer alone or pre-absorbed on commercial CCP2 plates. To eliminate antigen-antibody complexes, the liquid phase mixtures were centrifuged at 13 000 rpm, for 15 minutes, before the supernatants were transferred to CEP-1-coated plates and assessed as described above Inhibition of binding to CEP-1, for serum samples pre-absorbed to CCP, was calculated in relation to the maximum inhibition, which by definition was set to 100% for samples pre-incubated with CEP-1.

Generation of Rabbit Anti-Peptide 1A (CEP-1) Antibodies

A rabbit polyclonal anti-peptide 1 (anti-CEP-1) antibody was generated at Cambridge Research Biochemicals. Briefly; 2 rabbits were immunised subcutaneously every two weeks, for 10 weeks, with 200 µg KLH-conjugated Peptide 1A (peptide/KLH ratio 1:1) in FIA per boost. Blood was collected seven days after each injection and sera analysed for presence of anti-Peptide 1A antibodies. When antibody titres had reached significant levels, animals were sacrificed and blood harvested. The crude antisera were purified by affinity chromatography on a thiopropyl sepharose column conjugated to Peptide 1A. Anti-Peptide 1A specific antibodies were eluted by triethylamine (TEA) followed by glycine and further depleted of non-specific antibodies with a thiopropyl sepharose column, conjugated to the control peptide (peptide D1) containing native arginines instead of citrulline). Alternatively, the crude antisera were depleted of cross-reactive antibodies by chromatography on a thiopropyl sepharose column conjugated to peptide 1D. The unbound fraction was affinity purified by affinity chromatography on a second thiopropyl sepharose column conjugated to Peptide 1A. Anti-Peptide 1A specific antibodies were eluted by triethylamine (TEA) followed by glycine and further depleted of non-specific antibodies by three subsequent passages through the depleting column Purified anti-peptide 1 antibodies, 0.39 mg/ml, were collected as the unbound fraction from the depleting column and stored at −20° C. until further use.

Purification of Human Anti-Peptide 1A (Anti CEP-1) Antibodies

Serum, from an RA-patient with high titres of anti-Peptide 1A (anti CEP-1) antibodies, was circulated through a thiopropyl sepharose column, derivatised with Peptide 1A. Bound antibodies were eluted, after repeated PBS-washes, using 3M GuHCl. Purified anti-Peptide 1A antibodies were dialysed against PBS and stored at −20° C. until further use.

ELISA to Assess CEP-1-Specificity of Affinity Purified Anti-CEP-1 Antibodies

Affinity purified anti-CEP-1 antibodies (rabbit and human) were tested for their anti-CEP-1-specificity in serial dilutions (starting at 1:50 for the rabbit anti-CEP-1 antibody and at 1:2 for the human anti-CEP-1 antibody) on plates coated with peptide 1A or peptide 1D, and assayed as described above in the ELISA section Lysing of Bacteria

*P. gingivalis* was cultured in Trypticase soy broth, supplemented with bovine haemin (50 µg/ml) and menadione (50 µg/ml), harvested by centrifugation and subjected to sonication in the presence of a protease inhibitor cocktail (Roche) before being freeze dried. *P. gingivalis* was later re-dissolved in 0.1M Tris-HCl, pH 7.6. Cultures of *Streptococcus pyogenes* were boiled and kept at −20° C. until further lysed by sonication and a 10 minutes incubation with lysozyme (2 mg/ml) and mutanolysin (200 units/ml) at 37° C. The Streptococcal lysate was then centrifuged at 13 000 rpm for 15 minutes to remove insoluble material. Protein concentrations were determined using the Bradford assay (Bio-Rad Laboratories, Munchen).

In Vitro Deimination

Bacterial lysates and non-neuronal α-enolase (Hytest, Turku, Finland) were diluted to a concentration of 0.9 mg/ml in PAD-buffer (0.1 M Tris-HCl, pH 7.6, 10 mM $CaCl_2$, 5 mM dithiothreitol) and incubated with rabbit skeletal PAD (Sigma), at a concentration of 2 U/mg protein, for 2 hours at 50° C. Citrullination was terminated by the addition of 20 mM EDTA. Control proteins were either treated similarly, apart from the addition of PAD, or by direct addition of EDTA in the absence CaCl and PAD. All samples were stored at −20° C. until further use.

Immunoblotting

Bacterial lysates were separated on 4-12% NuPAGE Bis-Tris gels (Invitrogen, Paisley, Renfrewshire, UK) and transferred to nitrocellulose membranes. Non-specific binding was blocked with 5% non-fat milk (diluted in PBS-Tween, 0.05%) overnight at 4° C. before incubation with the primary antibody (rabbit anti-enolase IgG, diluted 1:200, (Santa Cruz Biotechnology, Santa Cruz, Calif., USA) or rabbit anti-Peptide 1A antibody, diluted 1:25, or non-diluted human anti-Peptide 1A antibody) for 1.5 hour at room temperature. Membranes were washed in PBS-Tween (0.05%) and incubated with peroxidase-conjugated secondary antibody (swine anti-rabbit IgG, diluted 1:3000, (Dako, Denmark) or mouse anti-human IgG, diluted 1:1000, (Hybridoma Reagent Laboratory, Baltimore, USA) for 1 hour at room temperature. Following another wash, membranes were developed using the enhanced chemiluminescence technique (Amersham Biosciences, Little Chalfont, Buckinghamshire, UK). Citrullinated proteins were detected using the anti-citrulline (modified) detection kit (Upstate, Lake Placid, N.Y., USA) in accordance with the manufacturer's instructions.

Statistical Analysis

All data were evaluated using the Mann-Whitney U-test for independent groups.

Results

Figure 1:
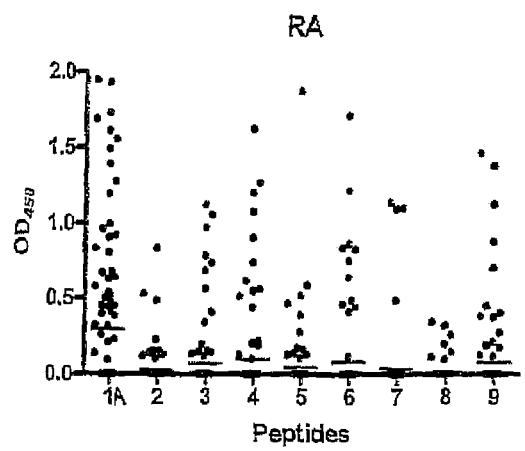
FIGS. 1A-C are charts showing IgG responses to citrullinated α-enolase peptides in rheumatoid arthritis (RA) patients (n=102) (FIG. 1A); non-RA patient controls (n=92) (FIG. 1B), and healthy controls (n=92) (FIG. 1C). IgG was measured by ELISA and data presented as peptide $OD_{450}$ with the background (carbonate buffer) $OD_{450}$ subtracted.
Figure 1:
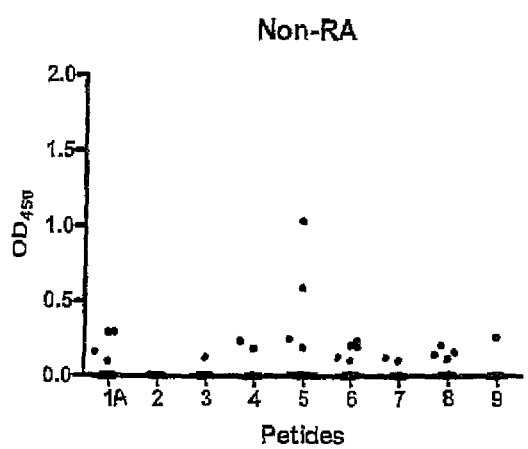
Figure 1:
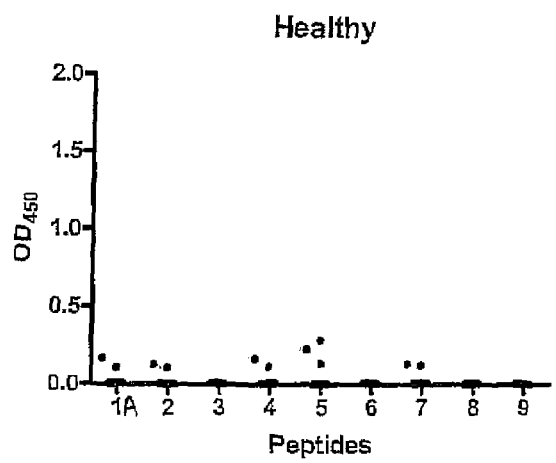
Figure 9:
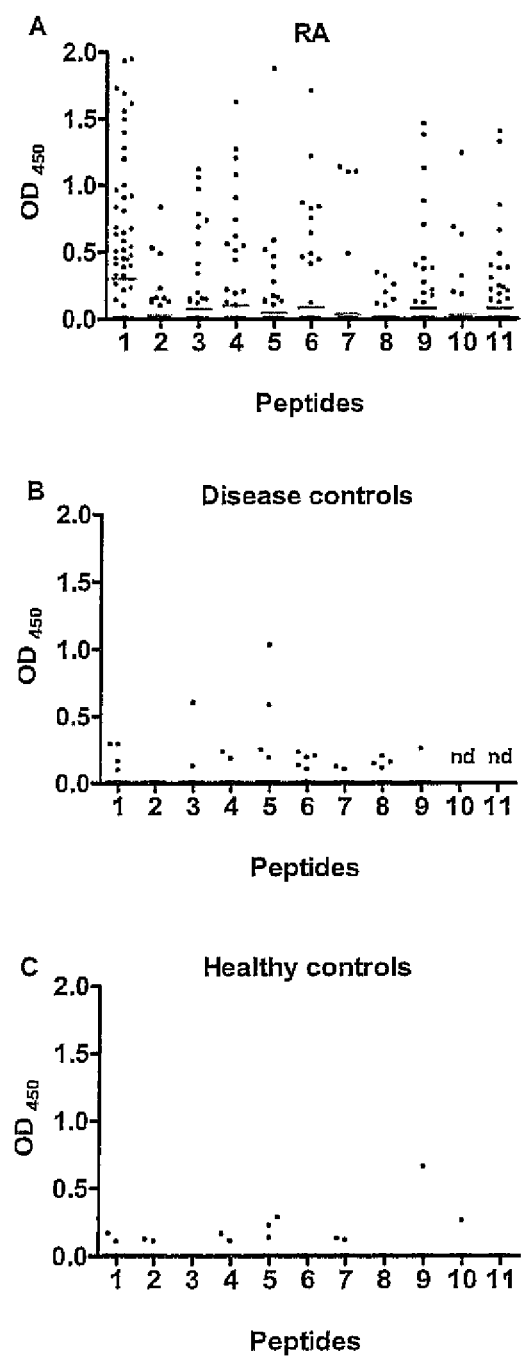

Detection of a Specific Antibody Response to Citrullinated α-Enolase Peptides in Patients with RA Nine or eleven (in relation to FIGS. 9 to 16) cyclic citrullinated peptides (Table 1 and Table 2), covering 15 of the 17 arginine residues within α-enolase, were selected on the basis of either containing more than one potential citrulline residue within a 20 amino acid sequence, or by the demonstration (by mass spectrometry) that arginines had been deiminated to citrulline in vitro in our previous study [29]. These citrullinated peptides are identified as Peptide 1A and Peptides 2 to 11 in Table 1. Each was synthesised and tested for reactivity in 102 RA-patients, 92 or 110 disease controls and 92 healthy controls. Results demonstrated that 64% of patients with RA, but 15% of the controls (18% with the 92 control group), had an IgG immune response to one or several citrullinated α-enolase peptides. The pattern of reactivity in RA patients varied, with the majority of patients having an antibody response to multiple citrullinated α-enolase peptides. The antibodies seen in the controls, on the other hand, mainly reacted with one of the peptides (ie was mainly restricted to one of the peptides), and the IgG antibody levels were significantly lower than those observed in patients with RA (FIG. 9 and FIG. 1).

TABLE 2

Antibody-reactivity to different α-enolase peptides.

| Peptide | | % positive (cut-off: OD$_{450}$ = 0.1) | | |
|---|---|---|---|---|
| | | | Disease | Healthy |
| Name | Sequence | RA | controls | controls |
| | | (n = 102) | (n = 110) | (n = 92) |
| 1A(CEP-1) | ckiha-X-eifds-X-gnptvec (SEQ ID NO: 9) | 37 | 3 | 2 |
| 1A P. gingivalis | ckiig-X-eilds-X-gnptvec (SEQ ID NO: 16) | 34 | nd | nd |
| 1B | ckiha-R-eifds-X-gnptvec (SEQ ID NO: 10) | 40 | nd | nd |
| 1C | ckiha-X-eifds-R-gnptvec (SEQ ID NO: 11) | 20 | nd | nd |
| 1D | ckiha-R-eifds-R-gnptvec (SEQ ID NO: 12) | 5 | 2 | 3 |
| 2 | cvdlftskglf-X-aavpsgc (SEQ ID NO: 17) | 10 | 0 | 2 |
| 3 | cyealel-X-dndkt-X-ymgkgvskc (SEQ ID NO: 18) | 15 | 2 | 0 |
| 4 | cekgvply-X-hiadlagnsec (SEQ ID NO: 19) | 16 | 2 | 2 |
| 5 | cnf-X-eam-X-igaevyhnlknc (SEQ ID NO: 20) | 11 | 4 | 3 |
| 6 | cf-X-sgkydldfkspddps-X-yc (SEQ ID NO: 21) | 12 | 5 | 0 |
| 7 | cangwgvmvsh-X-sgetedtc (SEQ ID NO: 22) | 4 | 2 | 2 |
| 8 | cakyngll-X-ieeelgskac (SEQ ID NO: 23) | 7 | 4 | 0 |
| 9 | ckfag-X-nf-X-nplakc (SEQ ID NO: 24) | 15 | 1 | 1 |
| 10 | cigvvgddltvtnpk-X-iakac (SEQ ID NO: 25) | 6 | nd | 1 |
| 11 | cnpk-X-iakavnekscncllc (SEQ ID NO: 26) | 18 | nd | 0 |

Identification of an Immunodominant Epitope within Citrullinated α-Enolase

Figure 3:
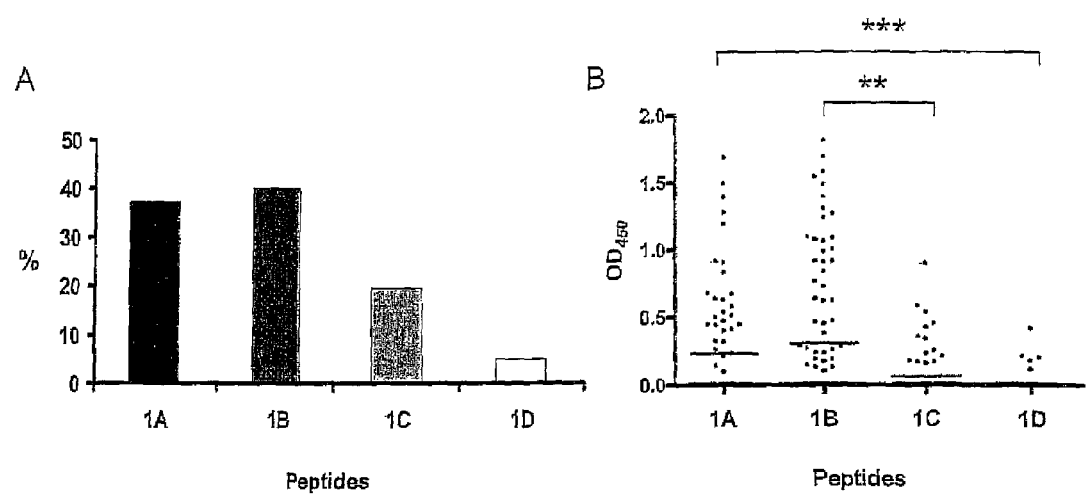

Peptide 1A was the immunodominant peptide, with a sensitivity of 37.3% in RA and a specificity of 97% (FIG. 2). In studies using the larger control group, peptide 1A reacted with 2% of the health controls and 3% of the disease controls (Table 2). Peptide 1A consists of a region of human alpha-enolase KIHAXEIFDSXGNPTVE (SEQ ID NO: 7), and N- and C-terminal cysteine residues to facilitate cyclisation. The X residues in Peptide 1A are both citrulline. However, alpha-enolase might naturally contain an arginine in place of citrulline at one or both of these positions. To map the antibody epitope further and to investigate the citrulline dependence of this antibody response, another three cyclic peptides (Peptide 1B, 1C and 1D) were synthesised (Table 1 and 2). The low reactivity towards control Peptide 1D, which does not contain any citrulline residues, demonstrates the importance of citrulline in this B-cell epitope. The larger percentage of RA-patients positive for antibodies to peptide 1B (40%) as compared to Peptide 1C (20%), as well as the higher antibody levels to Peptide 1B than to Peptide 1C, indicates that it is the second citrulline residue, rather than the first, that is most important for the antibody recognition (FIG. 3 and FIG. 10). Both Peptide 1A and 1B can be considered to be immunodominant peptides. Peptide 1A, containing both citrullinated residues, was chosen for further study and referred to as citrullinated α-enolase peptide-1 (CEP-1).

ACPA-Production in Anti-CCP Negative RA-Patients

Anti-CCP2 antibodies in the same serum samples gave a sensitivity of 71% with a specificity of 98% when assayed by "Immunoscan RA" (Catalogue No. RA-96RT) from Eurodiagnostica AB, Medeon, SE-205 12 Malmo, Sweden. Interestingly, 7 (23%) of the anti-CCP negative RA-patients were positive in the citrullinated α-enolase peptide (CEP-1) based ELISA (data not shown). Hence, combining anti-CCP and anti-citrullinated α-enolase peptide results increased the overall sensitivity to 77.5% for ACPA in this cohort.

The Diagnostic Sensitivity and Specificity of the Anti-CEP-1 ELISA is Confirmed in an Independent Cohort of Patients with RA To confirm that the high levels of antibodies to CEP-1 were not a peculiarity of the patients in our study, we tested 81 patients with RA and 82 healthy controls from a US cohort in the anti-CEP-1 antibody ELISA. To compare the data with the UK cohort, the OD of the 98$^{th}$ percentile of controls was used as the cut-off point for positive samples. The sensitivity was increased to 62% in the US RA population, with a specificity of 98% (FIG. 11). Disease controls were not examined in this part of the study.

RA Patients Have Anti-CEP-1-Specific, as Well as CCP Cross-Reactive Antibodies

Figure 12:
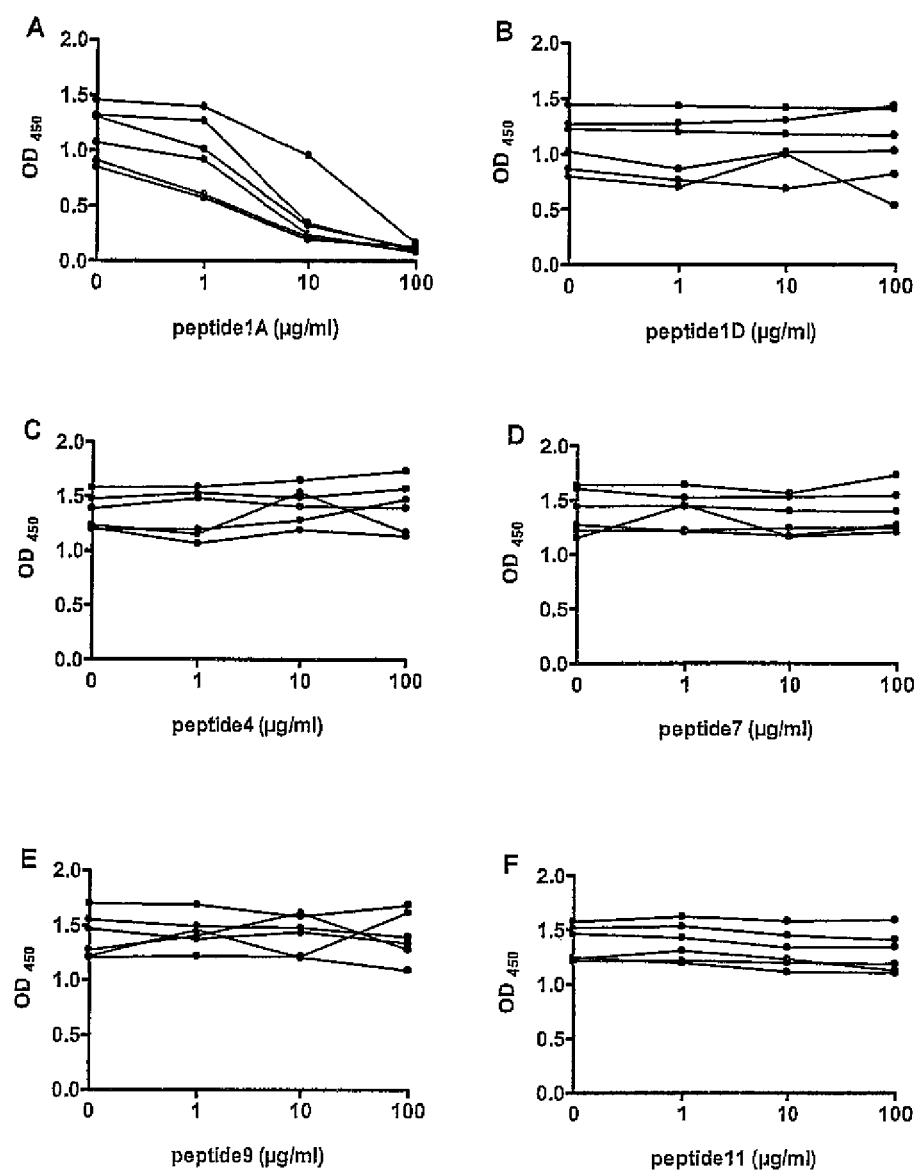

The epitope-specificity of the anti-CEP-1 antibody response was tested in two separate inhibition assays. In the first experiment inhibition of binding to CEP-1 was evaluated in sera from six anti-CEP-1 positive rheumatoid patients using liquid phase. There was a dose-dependent inhibition by the homologous peptide, while no inhibition was seen by the arginine-containing control peptide 1D or by citrullinated α-enolase peptides 4, 7, 9 and 11 (FIG. 12). In the second experiment, where we examined cross-reactivity to CCP, it was necessary to use the commercially available CCP2 plates in a solid phase assay, because the sequences of the peptides used in the assay have not been published. In nine double positive (anti-CEP-1 positive and anti-CCP positive) RA samples, pre-absorption on CCP plates showed inhibition of anti-CEP-1 binding varying from 0%, in two of the sera, rising to a maximum of 53% in one sample (FIG. 13). Since there is almost no cross-reactivity in the majority of sera investigated the CEP-1 sequence does not appear to be present in the CCP2 mix. There may be a sequence in the CCP2 mix that shows some cross-reactivity with some of the anti-CEP-1-specific antibodies in a minority (4/9) of the RA sera.

Anti-Peptide 1A Antibody Levels Decrease in Response to Combination Therapy

Figure 4:
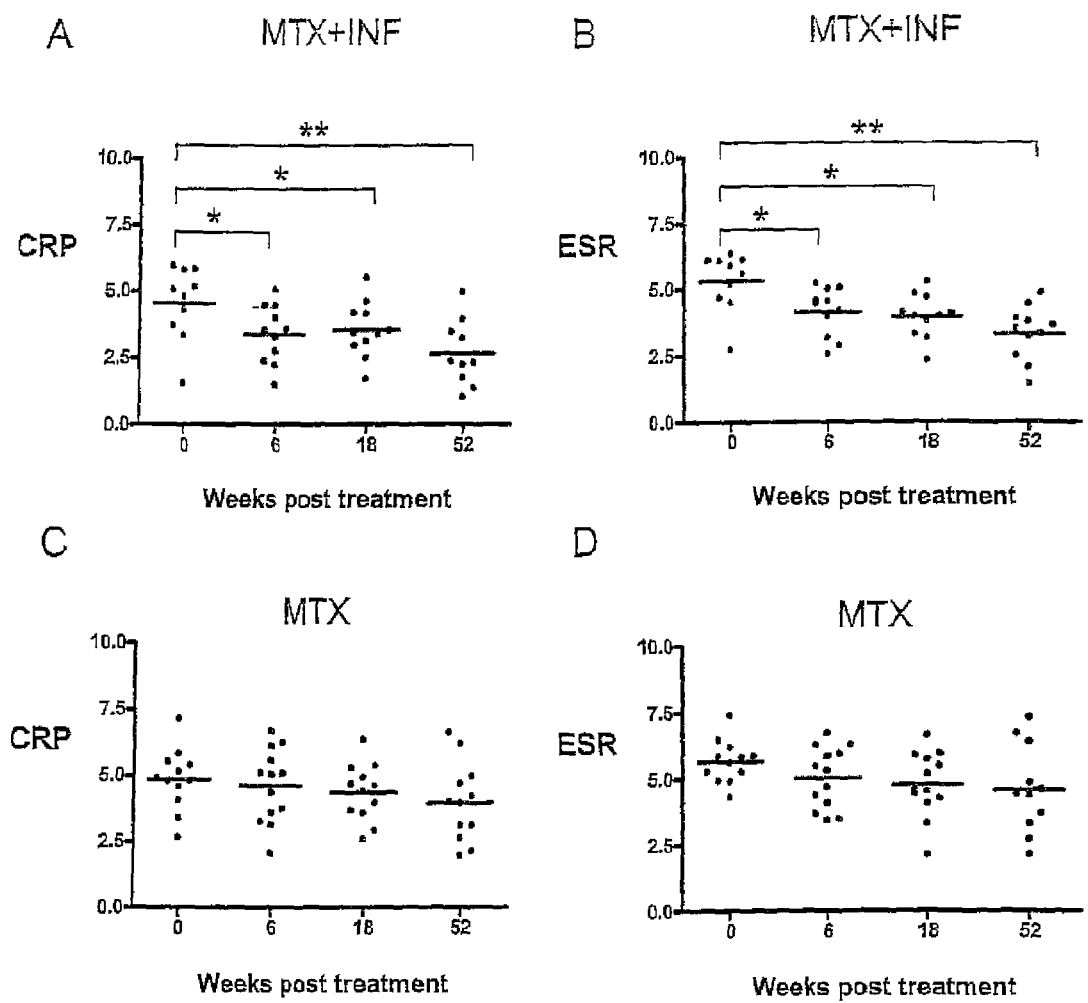
Figure 5:
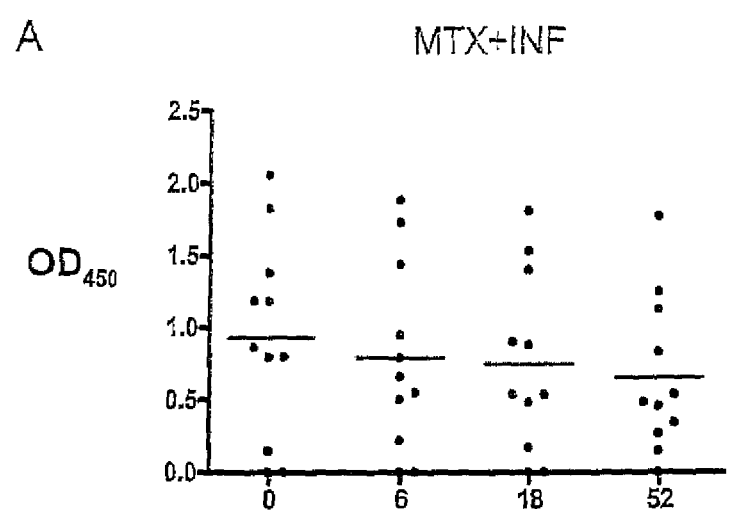
Figure 5:
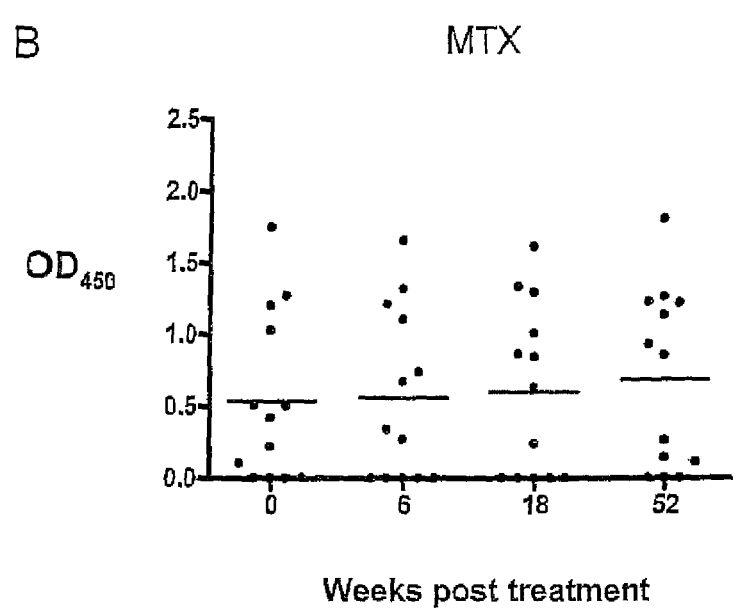

In a small cohort of 24 patients with RA, anti-Peptide 1A and anti-CCP antibody levels were measured over time in response to different treatment strategies. 13 patients were treated with methotrexate (MTX), whilst 11 patients received a combination therapy of MTX and Infliximab (INF). Nine patients in each group were positive for anti-Peptide 1A antibodies at the start of the study, giving a higher sensitivity (75%) than in the larger cohort. The same patients in the MTX+INF-group and 10 out of 13 patients in the MTX-group were also positive for CCP at this time point. Average DAS28 (CRP and ESR) scores were similar in the two groups pre-treatment and did not change significantly 6, 18 or 52 weeks post treatment in the MTX-group, but they decreased in the MTX+INF-group (FIG. 4). A trend towards lower anti-Peptide 1A antibody levels was observed over time in response to combination therapy while the opposite was true for single MTX-therapy. However, neither of these changes reached statistical significance (FIG. 5). Anti-CCP levels did not change significantly over time in either of the two treatment groups (data not shown).

High Sequence Similarity Between Human and Bacterial Peptide 1

The sequence similarity between human and bacterial enolase is around 50%, when comparing the whole protein. However, when comparing the sequence for Peptide 1, the similarity is much higher; 65% for *Streptococcus pyogenes* (SwissProt accession number AAX71649.1) and 82% for *Porphyromonas gingivalis* (SwissProt accession number AAQ66821). For the nine amino acids spanning the immunodominant epitope on Peptide 1, the sequence similarity is even higher at 89% and 100% for *Streptococcus pyogenes* and *Porphyromonas gingivalis* respectively, as shown below.

TABLE 3

Sequence similarities, presented as percentages, between human α-enolase and bacterial enolases

| Species | Whole protein (aa 1-434) | Peptide 1 (aa 5-21) | Immunodominant epitope (aa13-21) | Peptide 1 sequence |
|---|---|---|---|---|
| Human | | | | kiha-R-eifds-R-gnptve (SEQ ID NO. 14) |
| S. pyogenes | 46% | 65% | 89% | dvya-R-evlds-R-gnptle (SEQ ID NO. 27) |
| P. gingivalis | 51% | 82% | 100% | kiig-R-eilds-R-gnptve (SEQ ID NO. 28) |

Percentage similarities are shown for the whole protein (column 2), Peptide 1 (column 3) and the immunodominant epitope (column 4). The Peptide 1 sequence alignment for human and bacterial enolase is shown in column 5.

Generation of Anti-Peptide 1A Antibodies

Figure 6:
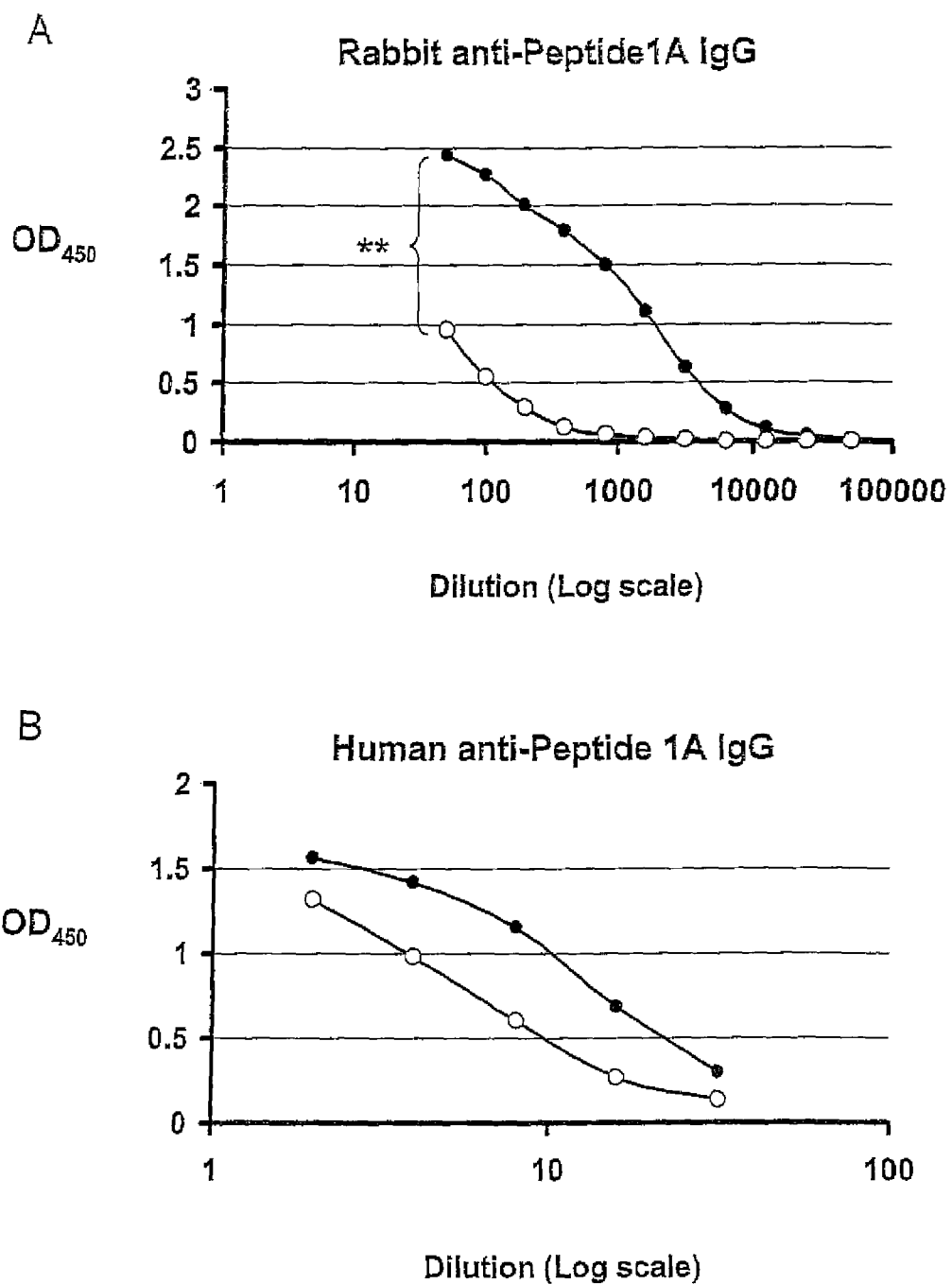

Polyclonal anti-human Peptide 1A antibodies were raised in rabbits, and human anti-Peptide 1A antibodies were purified from serum from a patient with RA. Specificity for Peptide 1A was analysed by ELISA; serial dilutions of the rabbit polyclonal antibody showed a high Peptide 1A-specificity, while affinity purified human immunoglobulins also showed reactivity with the arginine-containing control-peptide (FIG. 6).

Human Anti-Peptide 1A Antibodies Cross-React with Bacterial Enolase

Figure 16:
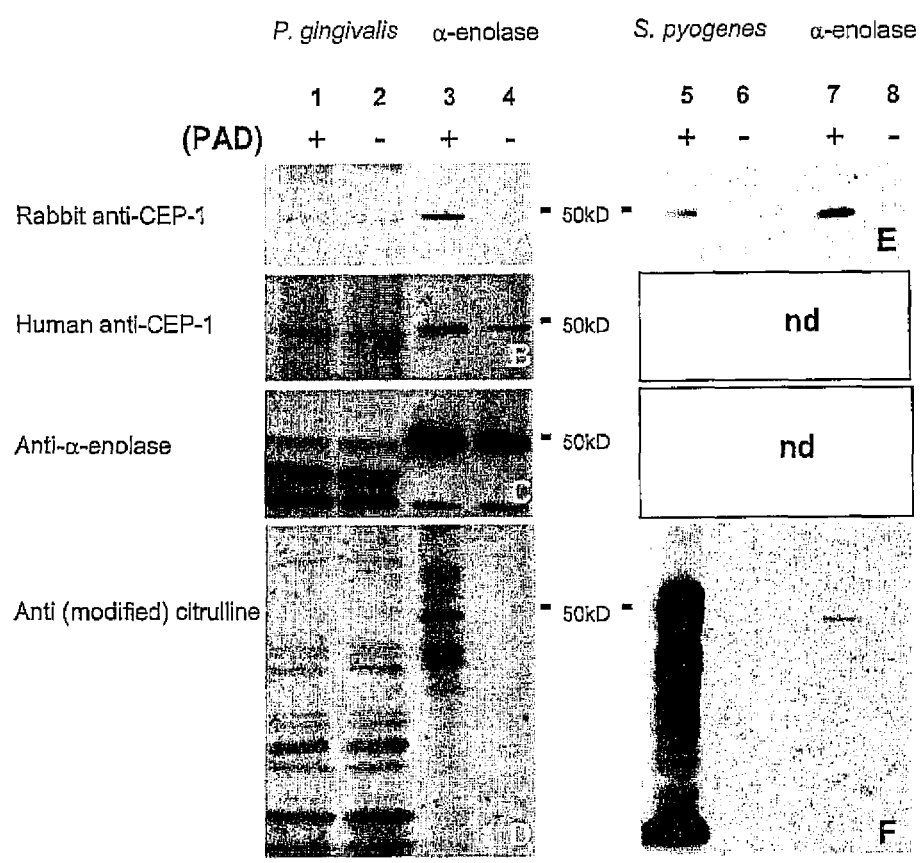

*Streptococcus pyogenes* and *Porphyromonas gingivalis* lysates were in vitro treated with PAD and blotted with anti-Peptide 1A antibodies. A band, which comigrated with purified human enolase at a molecular weight of 50 kD, was visualised in the lysates treated with PAD, but not in the untreated lysates (FIG. 16).

RA Patients Have Antibodies to *P. gingivalis* CEP-1 and Purified Anti-CEP-1 Antibodies Cross-React with Bacterial Enolase We tested the 102 RA patients from the UK cohort for reactivity with the *P. gingivalis* version of CEP-1 and 34% were found positive (Table 2), with similar IgG antibody levels as observed for the human version of this peptide (data not shown). In addition, serum samples from the US cohort were analysed for anti-*P. gingivalis* CEP-1-reactivity, and 54% of patients with RA and 2% of healthy controls were positive. This antibody response correlated strongly ($r^2=0.803$, $p<0.0001$) with the antibody response directed towards the human version of CEP-1 (FIG. 14). To investigate whether antibodies, directed to the immunodominant epitope of human α-enolase, also recognised epitopes in *P. gingivalis* enolase, bacterial lysates were in vitro treated with PAD, or left untreated, before immunoblotted with affinity purified anti-CEP-1 antibodies. These antibodies were generated in rabbits or purified from rheumatoid sera and their specificity for CEP-1 was analysed by ELISA. Serial dilutions of the rabbit polyclonal antibody showed a high CEP-1-specificity (FIG. 15A), while affinity purified human immunoglobulins also showed reactivity with the arginine-containing control-peptide (FIG. 15B). Western blots, using the purified anti-CEP-1 antibodies, showed a band, which co-migrated with citrullinated human α-enolase at a molecular weight of 50 kDa, in both the PAD-treated and the untreated *P. gingivalis* lysates (FIGS. 16A and B). This observation demonstrates, not only the presence of the CEP-1 epitope in *P. gingivalis* lysates, but also indicates endogenous citrullination which was confirmed using an anti-citrulline (modified) detection kit (FIG. 16D). In this experiment the levels of citrullination were low, requiring prolonged exposure of the blot to demonstrate it. Addition of exogenous PAD made no detectable difference to the amount of citrullination in the *P. gingivalis* polypeptides. This apparent resistance of the lysate to exogenous PAD was repeatable but unexplained and was not investigated further. A rabbit anti-human enolase antibody was used to demonstrate presence of bacterial enolase (FIG. 16C). In lysates from *S. pyogenes*, a bacterium that does not express PAD, the rabbit anti-CEP-1 antibody bound a protein of 50 kDa in the PAD-treated lysate but not in the untreated lysate (FIG. 16E). The anti-citrulline (modified) blot also confirmed that citrullinated proteins were restricted to the PAD-treated *S. pyogenes* lysate (FIG. 16F). Control blots, using goat anti-rabbit IgG, mouse anti-human IgG, or the anti-modified citrulline antibody on partially modified membranes, were all negative (data not shown).

Discussion

Here we report on the identification of a dominant B cell epitope in citrullinated α-enolase, CEP-1, reactive with 37%-62% of rheumatoid patient sera, and 2% of healthy controls. This epitope shows high sequence similarity to bacterial enolase and affinity-purified antibodies, specific for this epitope, react with both human and bacterial forms of the molecule. These data provide a new model for bacterial infection priming the autoimmune response in RA.

RA is associated with polyclonal B cell activation and autoantibody production, of which ACPA are the most specific. Recent publications provide evidence of a pathogenic involvement for these autoantibodies in RA. Petkova et al have, for example, demonstrated that passive transfer of plasma or serum from RA patients induced arthritis in mice deficient in the low-affinity inhibitory Fc receptor, FcγRIIB [44], and Kuhn et al showed that administration of ACPA enhanced the severity of arthritis in an experimental model of collagen-induced arthritis [45].

Since RA is a heterogeneous disease, where only four out of the seven ACR criteria have to be fulfilled for the diagnosis, it is likely that there are different subpopulations, with distinct etiopathological features. Two subgroups can, for example, clearly be distinguished based on the presence of ACPA [32]. In addition, as individual RA sera vary in their reactivity with a range of citrullinated peptides [32], it is possible that the underlying disease mechanisms, including the disease-driving antigen, differ also within the ACPA positive group.

In the present study we have focused on the anti-citrullinated α-enolase positive group within the ACPA positive subpopulation. We have previously characterised citrullinated α-enolase as a candidate physiological target for ACPA [29]. Using immunoblotting of whole protein, we found that 46% of patients with RA reacted with citrullinated α-enolase, of which seven (13%) also recognized the non-citrullinated protein. Fifteen percent of healthy controls reacted with both forms of the molecule and we speculated that this was due to reactivity with non-citrullinated epitopes. By testing serum samples from RA, disease control patients and healthy individuals, for reactivity with different citrullinated α-enolase peptides, we have now identified dominant peptides, Peptide 1A and 1B, with a sensitivity of nearly 40%. The specificity of this assay is very high at 97% or 98%. To confirm that this sensitivity, and high specificity, were not a peculiarity of the sera used at our institution we also tested 81 RA samples, and 82 healthy control samples, from a separate unit and found that the sensitivity was higher at 62%, with a specificity of 98%. This difference may be due to the fact that the US population was taken from patients participating in clinical trials, and therefore may have had more active disease than the UK cohort, which was derived from patients attending a routine clinic, many of whom were on treatment. Antibodies to native α-enolase have also been demonstrated in SLE and Behçet's disease (33, 34). In our study, patients with these diagnoses were uniformly negative for anti-CEP-1 antibodies, again supporting the concept that this epitope has specificity for patients with RA.

Importantly, 23% of anti-CCP negative RA patient serum samples were positive for citrullinated α-enolase, indicating that the ELISA, based on citrullinated α-enolase peptides, has the potential to complement the anti-CCP assay to increase the overall sensitivity for diagnosis of the disease. More importantly, it is possible that the subset of patients with this antibody have a distinct disease phenotype. In the small group of patients examined longitudinally there was a fall in the anti-Peptide 1A antibody in the group responding to treatment with infliximab and MTX, but not in the group treated with methotrexate alone. This may indicate that anti-Peptide 1A antibodies could be of value in monitoring response to treatment or possibly even predicting the response to therapy with anti-TNF. Prospective studies with much larger populations of patients are required to address this issue.

The importance of citrulline in the anti-Peptide 1A antibody response was demonstrated by the low degree of reactivity to the arginine-containing control peptide. However, it was also clear that neighbouring amino acids constitute important antigenic determinants, since the response to the other citrullinated α-enolase peptides was much weaker. The two amino acids, serine and glycine, flanking the second citrulline residue in CEP-1 have previously been reported to enhance ACPA recognition and binding (32, 35). We find that peptide 1B, containing the Ser-Cit-Gly-motif, had a higher sensitivity than peptide 1C, which lacks this motif. Our inhibition experiments demonstrate that anti-CEP-1 antibodies do not cross-react with other citrullinated α-enolase peptides, supporting the concept that citrullinated α-enolase is a true autoantigen in RA, with multiple epitopes driving the autoimmune response. The concordance between anti-CEP-1 and anti-CCP antibodies, as well as the results from our inhibition experiments, showing a variable degree of cross-reactivity between the two antigens, suggests that antibodies to citrullinated α-enolase may be one of a family of citrullinated autoantigens which is, at least in part, screened for by the anti-CCP assay. It appears that some anti-CEP-1 antibodies do not cross-react with CCP, while others do. Some patients have anti-CEP1 antibodies that cross-react with CCP to a certain degree (up to 53%), while other patients have anti-CEP-1 antibodies that do not cross-react with CCP at all. CEP-1 is not just a surrogate marker (surrogate antigen) for another citrullinated antigen (which is screened for by the CCP assay), but some of the anti-CEP-1 antibody response is detected by the CCP assay. It is possible that there is a degree of cross-reactivity at certain time points in the disease course, while later on, after affinity maturation of the anti-CEP-1 antibody response, this cross-reactivity is lost and the differences that we see between patients is explained by patients in different phases of the disease. Different antigens might drive the ACPA response in different patients; in patients where there is no cross-reactivity between CCP and CEP-1, citrullinated alpha-enolase might be the driving autoantigen (and the anti-CCP antibodies might be the result of epitope spreading), while in patients where there is cross-reactivity, other citrullinated antigens might be driving the immune response.

The anti-Peptide 1A antibody response could be the result of cross-reactivity with a yet unidentified protein, however, peptide 1A has no significant sequence similarity to other known human proteins, suggesting that citrullinated α-enolase is a true autoantigen.

Our data so far, using two independent cohorts of RA patients and appropriate normal and disease controls, support the concept that citrullinated α-enolase is a true autoantigen and that the sequence of the immunodominant peptide representing CEP-1 is important in the pathogenesis of the disease in the proportion of patients that have the antibody. Modification of coating conditions, the use of different configurations of peptides and a standard curve to ensure accurate quantification and reproducibility may increase the sensitivity of the assay. These refinements, together with further analysis of large cohorts, are expected to confirm that antibodies to CEP-1 define a specific clinical or immunogenetic subset of RA.

In light of the hypothesis that RA may be precipitated by infection, it was intriguing to find that the nine amino acids spanning the immunodominant epitope of Peptide 1A was 100% identical to citrullinated enolase encoded by *P. gingivalis*. *P. gingivalis* is a gram-negative bacterium that causes adult periodontitis (AP), a disease which shares many features with RA. Like RA, AP is a chronic inflammatory disorder where accumulation of immune cells leads to local production of pro-inflammatory cytokines, such as TNF and IL1-β, metalloproteinases (MMPs) and prostaglandins, which results in tissue swelling and degradation (reviewed in [36, 37]). Interestingly, RA is four times more common in patients with periodontitis than in the normal population [38]. Higher levels of antibodies to *P. gingivalis* [39] as well as a higher prevalence of advanced forms of periodontal destruction have also been reported in RA patients compared to controls. Finally, both RF-production and CCP-production has been associated with periodontal disease (36, 40). These data could imply a common underlying dysregulation of the host's immune response in the two conditions. But there is also a striking genetic similarity between the two diseases in that the both are associated with the HLA-SE (41, 42). This, together with the fact that *P. gingivalis* is the only bacterium known to synthesise its own PAD enzyme, (28) lends support to another hypothesis; that *P. gingivalis* may be 'the septic stimulus' in RA, as proposed by Rosenstein et al (37). Therefore individuals with periodontal infection may already be exposed to citrullinated antigens, including citrullinated bacterial enolase. In the genetic context of the HLA-SE, and in the presence of danger signals, this could result in a pathological immune response with the formation of ACPA. If an unspecific arthritis developed at a later time point, accompanied by citrullination of synovial proteins, anti-CEP-1 antibodies could cross-react with citrullinated proteins in the joint, amplify the inflammatory process and cause RA.

We were in fact able to demonstrate such antibody cross-reactivity between human and bacterial enolase. Not only did RA patients have antibodies reactive with the *P. gingivalis* version of CEP-1, but anti-CEP-1 antibodies, raised in rabbits or purified from an RA patient, bound *P. gingivalis* enolase in vitro. The observation that purified anti-CEP-1 antibodies bound a 50 kDa protein, co-migrating with citrullinated human α-enolase, in both PAD-treated and untreated *P. gingivalis* lysates, but only in PAD-treated *S. pyogenous* lysates, indicates that endogenous citrullination had occurred in *P. gingivalis*. This interesting finding was also supported by the demonstration of citrullinated proteins in the 'native' lysate of *P. gingivalis*. Hence, based on our data, we propose that autoimmunity in the subset of RA patients with a humoral immune response to CEP-1 is primed by infection with bacteria and that tolerance is broken by citrullinated bacterial enolase. Cross-reactivity with citrullinated human α-enolase within the joint then leads to the chronic destructive inflammation that characterises RA.

REFERENCES

1. Schellekens, G. A., Visser, H., de Jong, B. A., van den Hoogen, F. H., Hazes, J. M., Breedveld, F. C., and van Venrooij, W. J. 2000. The diagnostic properties of rheumatoid arthritis antibodies recognizing a cyclic citrullinated peptide. Arthritis Rheum 43:155-163.
2. van Venrooij, W. J., Hazes, J. M., and Visser, H. 2002. Anticitrullinated protein/peptide antibody and its role in the diagnosis and prognosis of early rheumatoid arthritis. Neth J Med 60:383-388.
3. Kinloch, A., Lundberg, K., and Venables, P. 2006. The pathogenic role of antibodies to citrullinated proteins in rheumatoid arthritis. Expert Rev Clin Immunol 2:365-375.
4. Kuhn, K. A., Kulik, L., Tomooka, B., Braschler, K. J., Arend, W. P., Robinson, W. H., and Holers, V. M. 2006. Antibodies against citrullinated proteins enhance tissue injury in experimental autoimmune arthritis. J Clin Invest 116:961-973.
5. Nielen, M. M., van Schaardenburg, D., Reesink, H. W., van de Stadt, R. J., van der Horst-Bruinsma, I. E., de Koning, M. H., Habibuw, M. R., Vandenbroucke, J. P., and Dijkmans, B. A. 2004. Specific autoantibodies precede the symptoms of rheumatoid arthritis: a study of serial measurements in blood donors. Arthritis Rheum 50:380-386.
6. Rantapaa-Dahlqvist, S., de Jong, B. A., Berglin, E., Hallmans, G., Wadell, G., Stenlund, H., Sundin, U., and van Venrooij, W. J. 2003. Antibodies against cyclic citrullinated peptide and IgA rheumatoid factor predict the development of rheumatoid arthritis. Arthritis Rheum 48:2741-2749.
7. Forslind, K., Ahlmen, M., Eberhardt, K., Hafstrom, I., and Svensson, B. 2004. Prediction of radiological outcome in early rheumatoid arthritis in clinical practice: role of antibodies to citrullinated peptides (anti-CCP). Ann Rheum Dis 63:1090-1095.
8. Jansen, L. M., van Schaardenburg, D., van der Horst-Bruinsma, I., van der Stadt, R. J., de Koning, M. H., and Dijkmans, B. A. 2003. The predictive value of anti-cyclic citrullinated peptide antibodies in early arthritis. J Rheumatol 30:1691-1695.

9. Kastbom, A., Strandberg, G., Lindroos, A., and Skogh, T. 2004. Anti-CCP antibody test predicts the disease course during 3 years in early rheumatoid arthritis (the Swedish TIRA project). Ann Rheum Dis 63:1085-1089.

10. Saraux, A., Berthelot, J. M., Devauchelle, V., Bendaoud, B., Chales, G., Le Henaff, C., Thorel, J. B., Hoang, S., Jousse, S., Baron, D., et al. 2003. Value of antibodies to citrulline-containing peptides for diagnosing early rheumatoid arthritis. J Rheumatol 30:2535-2539.

11. Vencovsky, J., Machacek, S., Sedova, L., Kafkova, J., Gatterova, J., Pesakova, V., and Ruzickova, S. 2003. Autoantibodies can be prognostic markers of an erosive disease in early rheumatoid arthritis. Ann Rheum Dis 62:427-430.

12. Kroot, E. J., de Jong, B. A., van Leeuwen, M. A., Swinkels, H., van den Hoogen, F. H., van't H of, M., van de Putte, L. B., van Rijswijk, M. H., van Venrooij, W. J., and van Riel, P. L. 2000. The prognostic value of anti-cyclic citrullinated peptide antibody in patients with recent-onset rheumatoid arthritis. Arthritis Rheum 43:1831-1835.

13. Meyer, O., Labarre, C., Dougados, M., Goupille, P., Cantagrel, A., Dubois, A., Nicaise-Roland, P., Sibilia, J., and Combe, B. 2003. Anticitrullinated protein/peptide antibody assays in early rheumatoid arthritis for predicting five year radiographic damage. Ann Rheum Dis 62:120-126.

14. Tamai, M., Kawakami, A., Uetani, M., Takao, S., Tanaka, F., Nakamura, H., Iwanaga, N., Izumi, Y., Arima, K., Aratake, K., et al. 2006. The presence of anti-cyclic citrullinated peptide antibody is associated with magnetic resonance imaging detection of bone marrow oedema in early stage rheumatoid arthritis. Ann Rheum Dis 65:133-134.

15. Vallbracht, I., Rieber, J., Oppermann, M., Forger, F., Siebert, U., and Helmke, K. 2004. Diagnostic and clinical value of anti-cyclic citrullinated peptide antibodies compared with rheumatoid factor isotypes in rheumatoid arthritis. Ann Rheum Dis 63:1079-1084.

16. van Gaalen, F. A., van Aken, J., Huizing a, T. W., Schreuder, G. M., Breedveld, F. C., Zanelli, E., van Venrooij, W. J., Verweij, C. L., Toes, R. E., and de Vries, R. R. 2004. Association between HLA class II genes and autoantibodies to cyclic citrullinated peptides (CCPs) influences the severity of rheumatoid arthritis. Arthritis Rheum 50:2113-2121.

17. Vossenaar, E. R., Smeets, T. J., Kraan, M. C., Raats, J. M., van Venrooij, W. J., and Tak, P. P. 2004. The presence of citrullinated proteins is not specific for rheumatoid synovial tissue. Arthritis Rheum 50:3485-3494.

18. Moscarello, M. A., Wood, D. D., Ackerley, C., and Boulias, C. 1994. Myelin in multiple sclerosis is developmentally immature. J Clin Invest 94:146-154.

19. Ishigami, A., Ohsawa, T., Hiratsuka, M., Taguchi, H., Kobayashi, S., Saito, Y., Murayama, S., Asaga, H., Toda, T., Kimura, N., et al. 2005. Abnormal accumulation of citrullinated proteins catalyzed by peptidylarginine deiminase in hippocampal extracts from patients with Alzheimer's disease. J Neurosci Res 80:120-128.

20. Makrygiannakis, D., Af Klint, E., Lundberg, I. E., Lofberg, R., Ulfgren, A. K., Klareskog, L., and Catrina, A. I. 2006. Citrullination is an inflammation dependent process. Ann Rheum Dis.

21. Klareskog, L., Stolt, P., Lundberg, K., Kallberg, H., Bengtsson, C., Grunewald, J., Ronnelid, J., Harris, H. E., Ulfgren, A. K., Rantapaa-Dahlqvist, S., et al. 2006. A new model for an etiology of rheumatoid arthritis: smoking may trigger HLA-DR (shared epitope)-restricted immune reactions to autoantigens modified by citrullination. Arthritis Rheum 54:38-46.

22. van der Helm-van Mil, A. H., Verpoort, K. N., Breedveld, F. C., Huizinga, T. W., Toes, R. E., and de Vries, R. R. 2006. The HLA-DRB1 shared epitope alleles are primarily a risk factor for anti-cyclic citrullinated peptide antibodies and are not an independent risk factor for development of rheumatoid arthritis. Arthritis Rheum 54:1117-1121.

23. Pedersen, M., Jacobsen, S., Klarlund, M., Pedersen, B. V., Wiik, A., Wohlfahrt, J., and Frisch, M. 2006. Environmental risk factors differ between rheumatoid arthritis with and without auto-antibodies against cyclic citrullinated peptides. Arthritis Res Ther 8:R133.

24. Origuchi, T., Eguchi, K., Kawabe, Y., Yamashita, I., Mizokami, A., Ida, H., and Nagataki, S. 1995. Increased levels of serum IgM antibody to staphylococcal enterotoxin B in patients with rheumatoid arthritis. Ann Rheum Dis 54:713-720.

25. Takahashi, Y., Murai, C., Shibata, S., Munakata, Y., Ishii, T., Ishii, K., Saitoh, T., Sawai, T., Sugamura, K., and Sasaki, T. 1998. Human parvovirus B19 as a causative agent for rheumatoid arthritis. Proc Natl Acad Sci USA 95:8227-8232.

26. Blaschke, S., Schwarz, G., Moneke, D., Binder, L., Muller, G., and Reuss-Borst, M. 2000. Epstein-Barr virus infection in peripheral blood mononuclear cells, synovial fluid cells, and synovial membranes of patients with rheumatoid arthritis. J Rheumatol 27:866-873.

27. Saal, J. G., Steidle, M., Einsele, H., Muller, C. A., Fritz, P., and Zacher, J. 1992. Persistence of B19 parvovirus in synovial membranes of patients with rheumatoid arthritis. Rheumatol Int 12:147-151.

28. McGraw, W. T., Potempa, J., Farley, D., and Travis, J. 1999. Purification, characterization, and sequence analysis of a potential virulence factor from *Porphyromonas gingivalis*, peptidylarginine deiminase Infect Immun 67:3248-3256.

29. Kinloch, A., Tatzer, V., Wait, R., Peston, D., Lundberg, K., Donatien, P., Moyes, D., Taylor, P. C., and Venables, P. J. 2005. Identification of citrullinated alpha-enolase as a candidate autoantigen in rheumatoid arthritis. Arthritis Res Ther 7:R1421-1429.

30. Albert, L. J., and Inman, R. D. 1999. Molecular mimicry and autoimmunity. N Engl J Med 341:2068-2074.

31. Huizing a, T. W., Amos, C. I., van der Helm-van Mil, A. H., Chen, W., van Gaalen, F. A., Jawaheer, D., Schreuder, G. M., Wener, M., Breedveld, F. C., Ahmad, N., et al. 2005. Refining the complex rheumatoid arthritis phenotype based on specificity of the HLA-DRB1 shared epitope for antibodies to citrullinated proteins. Arthritis Rheum 52:3433-3438.

32. Schellekens, G. A., de Jong, B. A., van den Hoogen, F. H., van de Putte, L. B., and van Venrooij, W. J. 1998. Citrulline is an essential constituent of antigenic determinants recognized by rheumatoid arthritis-specific autoantibodies. J Clin Invest 101:273-281.

33. Pratesi, F., Moscato, S., Sabbatini, A., Chimenti, D., Bombardieri, S., and Migliorini, P. 2000. Autoantibodies specific for alpha-enolase in systemic autoimmune disorders. J Rheumatol 27:109-115.

34. Lee, K. H., Chung, H. S., Kim, H. S., Oh, S. H., Ha, M. K., Baik, J. H., Lee, S., and Bang, D. 2003. Human alpha-enolase from endothelial cells as a target antigen of anti-endothelial cell antibody in Behcet's disease. Arthritis Rheum 48:2025-2035.

35. Girbal-Neuhauser, E., Durieux, J. J., Arnaud, M., Dalbon, P., Sebbag, M., Vincent, C., Simon, M., Senshu, T., Masson-Bessiere, C., Jolivet-Reynaud, C., et al. 1999. The epitopes targeted by the rheumatoid arthritis-associated antifilaggrin autoantibodies are posttranslationally generated on various sites of (pro)filaggrin by deimination of arginine residues. J Immunol 162:585-594.
36. Mercado, F. B., Marshall, R. I., and Bartold, P. M. 2003. Inter-relationships between rheumatoid arthritis and periodontal disease. A review. J Clin Periodontol 30:761-772.
37. Rosenstein, E. D., Greenwald, R. A., Kushner, L. J., and Weissmann, G. 2004. Hypothesis: the humoral immune response to oral bacteria provides a stimulus for the development of rheumatoid arthritis. Inflammation 28:311-318.
38. Mercado, F., Marshall, R. I., Klestov, A. C., and Bartold, P. M. 2000. Is there a relationship between rheumatoid arthritis and periodontal disease? J Clin Periodontol 27:267-272.
39. Ogrendik, M., Kokino, S., Ozdemir, F., Bird, P. S., and Hamlet, S. 2005. Serum antibodies to oral anaerobic bacteria in patients with rheumatoid arthritis. MedGenMed 7:2.
40. Havemose-Poulsen, A., Westergaard, J., Stoltze, K., Skjodt, H., Danneskiold-Samsoe, B., Locht, H., Bendtzen, K., and Holmstrup, P. 2006. Periodontal and hematological characteristics associated with aggressive periodontitis, juvenile idiopathic arthritis, and rheumatoid arthritis. J Periodontol 77:280-288.
41. Katz, J., Goultschin, J., Benoliel, R., and Brautbar, C. 1987. Human leukocyte antigen (HLA) DR4. Positive association with rapidly progressing periodontitis. J Periodontol 58:607-610.
42. Marotte, H., Farge, P., Gaudin, P., Alexandre, C., Mougin, B., and Miossec, P. 2006. The association between periodontal disease and joint destruction in rheumatoid arthritis extends the link between the HLA-DR shared epitope and severity of bone destruction. Ann Rheum Dis 65:905-909.
43. Arnett, F. C., Edworthy, S. M., Bloch, D. A., McShane, D. J., Fries, J. F., Cooper, N. S., Healey, L. A., Kaplan, S. R., Liang, M. H., Luthra, H. S., et al. 1988. The American Rheumatism Association 1987 revised criteria for the classification of rheumatoid arthritis. Arthritis Rheum 31:315-324.
44. Petkova, S. B., Konstantinov, K. N., Sproule, T. J., Lyons, B. L., Awwami, M. A. and Roopenian, D. C., Human antibodies induce arthritis in mice deficient in the low-affinity inhibitory IgG receptor Fc gamma RIIB. J Exp Med 2006. 203: 275-280.
45 Kuhn, K. A., Kulik, L., Tomooka, B., Braschler, K. J., Arend, W. P., Robinson, W. H. and Holers, V. M., Antibodies against citrullinated proteins enhance tissue injury in experimental autoimmune arthritis. J Clin Invest 2006. 116: 961-973.

EXAMPLE 2

Sera from 29 patients diagnosed with systemic lupus erythromatosus (SLE) were tested by ELISA for reactivity with 11 citrullinated α-enolase peptides, namely Peptide 1A, 1B, 1D and Peptides 2 to 9 as shown in Table 1. The ELISA assay was as described in Example 1.

The quantity of antibody, from each patient sample, binding to each peptide, is reflected by the OD (450 nm) in the ELISA assay. The OD (450 nm) corresponding to the background (buffer only) was subtracted. The results, after subtraction of background, are depicted in FIG. 8A. All OD (450 nm) values below 0.1 were considered negative (=0).

The percentages of SLE patients scored as positive for antibodies to each of the 11 citrullinated peptides were calculated, as shown in FIG. 9B. 6.9% of SLE sera was scored as positive for antibodies to Peptide 1A (2 patients); 3.4% of SLE sera was scored as positive for antibodies to Peptide 6 (1 patient) and a further 3.4% of SLE sera was scored as positive for antibodies to Peptide 7.

The percentage of SLE patients positive for any of the 11 citrullinated peptides was calculated as 13.8%.

Sera from the 29 SLE patients were also tested for antibodies to cyclic citrullinated peptides using the commerically available anti-CCP ELISA. All patients were negative for such anti-CCP antibodies.

EXAMPLE 3

Sera from healthy controls and 511 rheumatoid arthritis patients from the Swedish EIRA (Epidemiological Investigation of Rheumatoid Arthritis) cohort (Stolt et al, Quantification of the influence of cigarette smoking on RA, Ann Rheum Dis, 2003; 62:835-841), were tested for antibodies to cyclic citrullinated peptides using the commercially available anti-CCP ELISA. At least 600 healthy controls were screened and, amongst these, a rare population that were CCP positive (n=16) were identified. Two of these CCP positive individuals have developed RA since the blood samples were collected.

Sera from the 511 rheumatoid arthritis patients, 16 CCP positive healthy controls and 126 CCP negative healthy controls were also screened by ELISA for reactivity with CEP-1 (Peptide 1A) as described in Example 1. The rheumatoid arthritis patients were divided into CCP positive (n=410) and CCP negative (n=101) groups.

Sixty percent of CCP+ RA were also positive for anti-CEP-1 antibodies. Interestingly, 17% of CCP− RA patients had anti-CEP-1 antibodies. Only 0.8% of the CCP− healthy controls were CEP-1+, while 25% of CCP+ healthy controls were also CEP-1+. The data are illustrated in FIG. 17.

EXAMPLE 4

A

A serum sample would be collected from a patient with arthritis and assayed for anti-citrullinated α-enolase peptides using the method of the invention, and anti-CCP2 antibodies using a commercially available ELISA. If the sample was found to be negative for anti-CCP2 antibodies, but positive for anti-citrullinated enolase peptide antibodies, the physician would interpret this result and diagnose the arthritis as rheumatoid arthritis. Other clinical indications may be used by the physician to assist in arriving at a diagnosis.

B

A serum sample would be collected from a patient with rheumatoid arthritis and assayed for anti-citrullinated enolase peptides using the method of the invention. If the sample was positive in this test, the physician would interpret this result and diagnose a more severe form of disease. Other clinical indications may be used by the physician to assist in arriving at a diagnosis. The patient will be given a more careful follow-up and more aggressive treatment than if the sample had been scored as negative in the test.

C

A serum sample would be collected from a patient with early stage rheumatoid arthritis and assayed for anti-citrullinated enolase peptides using the method of the invention. If the sample was positive in this test, the physician would interpret this result and prescribe treatment with an antibiotic such doxycycline. The patient may also be prescribed with conventional drugs, such as anti-TNF, to be used contemporaneously with the antibiotic.

D

A serum sample would be collected from a patient and assayed for anti-citrullinated enolase peptides using the method of the invention. If the sample was positive in this test, the physician would interpret this result and prescribe a novel treatment developed as a result of improved understanding of the pathogenesis of rheumatoid arthritis. Other clinical indications may be used by the physician to assist in determining a suitable course of therapy.

The contents of each of the references cited herein are incorporated by reference in their entirety, for all purposes.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

---

The invention claimed is:

1. A method for detection of the presence of antibody, comprising:
   a) exposing a citrullinated enolase peptide to a sample from an individual, wherein the citrullinated enolase peptide has an amino acid sequence consisting of fewer than fifty but at least five amino acids of the amino acid sequence of a region of human α-enolase encompassing amino acids 14 to 16 of human α-enolase in which amino acid 14 is serine, amino acid 15 is citrulline, and amino acid 16 is glycine, or a variant thereof with at least 95% sequence identity to said region of human α-enolase which variant retains the serine at amino acid 14, citrulline at amino acid 15, and glycine at amino acid 16, wherein the citrullinated enolase peptide optionally has a cysteine residue N-terminal and/or C-terminal to said region of human α-enolase, and b) detecting antibody which has bound to the peptide, wherein variants of the region of human α-enolase are defined as variants having an amino acid sequence consisting of fewer than fifty but at least five amino acids, wherein at one or more positions in such sequence, there are amino acid insertions, deletions, or substitutions, relative to the corresponding positions of the full length human α-enolase sequence.

2. The method of claim 1, further comprising exposing a control peptide to a sample from the same individual and detecting antibody which has bound to the control peptide, wherein the control peptide is identical to the citrullinated enolase peptide except that:

(a) the residue corresponding to human α-enolase amino acid 15 is replaced by a residue other than citrulline, and (b) where the citrullinated enolase peptide comprises a residue corresponding to amino acid 9 of human α-enolase, which residue is citrulline, the residue corresponding to amino acid 9 of human α-enolase in the control peptide is citrulline, or another residue.

3. The method of claim 2 wherein one or both amino acid residues of the control peptide corresponding to amino acid residues 15 or 9 of human α-enolase is arginine.

4. The method of claim 2 wherein:

(a) the citrullinated enolase peptide comprises or consists of KIHAXEIFDSXGNPTVE (SEQ ID NO. 7) and the control peptide comprises KIHAXEIFDSRGNPTVE (SEQ ID NO. 13) or KIHAREIFDSRGNPTVE (SEQ ID NO. 14), wherein X is citrulline, or (b) the citrullinated enolase peptide comprises or consists of KIHAREIFDSXGNPTVE (SEQ ID NO. 8) and the control peptide comprises or consists of KIHAREIFDSRGNPTVE (SEQ ID NO. 12), wherein X is citrulline.

5. The method of claim 1, further comprising testing a sample from the same individual for antibodies which bind to cyclic citrullinated peptides which peptides are not citrullinated enolase peptides with an amino acid sequence comprising the amino acid sequence of a region of human α-enolase consisting of five to 150 amino acids encompassing amino acids 14 to 16 of human α-enolase in which amino acid 15 is citrulline.

6. The method of claim 1, further comprising exposing the citrullinated enolase peptide to a control sample and detecting antibody which has bound to the peptide.

7. The method of claim 6, wherein the control sample is from one or more individuals not suffering from RA.

8. The method of claim 1, wherein the individual is a human.

9. The method of claim 1, wherein the sample is serum.

10. The method of claim 1, wherein the citrullinated enolase peptide is CKIHAXEIFDSXGNPTVEC (SEQ ID NO. 9) or CKIHAREIFDSXGNPTVEC (SEQ ID NO. 10), where X is citrulline, and wherein the citrullinated enolase peptide is cyclic.

11. The method of claim 1, wherein the citrullinated enolase peptide is a cyclic peptide.

12. The method of claim 1, wherein the detecting antibody which has bound to the peptide is carried out using an ELISA assay or a Western Blot assay.

13. The method of claim 12, wherein the assay is an ELISA assay.

14. The method of claim 1:

wherein the citrullinated enolase peptide is immobilized on a solid support.

\* \* \* \* \*

SEQUENCE LISTING

```
<160> NUMBER OF SEQ ID NOS: 31

<210> SEQ ID NO 1
<211> LENGTH: 21
<212> TYPE: PRT
<213> ORGANISM: Artificial Sequence
<220> FEATURE:
<223> OTHER INFORMATION: Schellekens cyclic protein
<220> FEATURE:
<221> NAME/KEY: UNSURE
<222> LOCATION: (9)..(9)
<223> OTHER INFORMATION: citrulline

<400> SEQUENCE: 1

His Gln Cys His Gln Glu Ser Thr Xaa Gly Arg Ser Arg Gly Arg Cys
1               5                   10                  15

Gly Arg Ser Gly Ser
            20

<210> SEQ ID NO 2
<211> LENGTH: 8
<212> TYPE: PRT
<213> ORGANISM: Homo sapiens

<400> SEQUENCE: 2

Phe Arg Ala Ala Val Pro Ser Gly
1               5

<210> SEQ ID NO 3
<211> LENGTH: 8
<212> TYPE: PRT
<213> ORGANISM: Homo sapiens

<400> SEQUENCE: 3

Ala Asn Phe Arg Glu Ala Met Arg
1               5

<210> SEQ ID NO 4
<211> LENGTH: 8
<212> TYPE: PRT
<213> ORGANISM: Homo sapiens

<400> SEQUENCE: 4

Ala Lys Phe Ala Gly Arg Asn Phe
1               5

<210> SEQ ID NO 5
<211> LENGTH: 8
<212> TYPE: PRT
<213> ORGANISM: Homo sapiens
```

<400> SEQUENCE: 5

Arg Tyr Met Gly Lys Gly Val Ser
1               5

<210> SEQ ID NO 6
<211> LENGTH: 434
<212> TYPE: PRT
<213> ORGANISM: Homo sapiens

<400> SEQUENCE: 6

Met Ser Ile Leu Lys Ile His Ala Arg Glu Ile Phe Asp Ser Arg Gly
1               5                   10                  15

Asn Pro Thr Val Glu Val Asp Leu Phe Thr Ser Lys Gly Leu Phe Arg
            20                  25                  30

Ala Ala Val Pro Ser Gly Ala Ser Thr Gly Ile Tyr Glu Ala Leu Glu
        35                  40                  45

Leu Arg Asp Asn Asp Lys Thr Arg Tyr Met Gly Lys Gly Val Ser Lys
    50                  55                  60

Ala Val Glu His Ile Asn Lys Thr Ile Ala Pro Ala Leu Val Ser Lys
65                  70                  75                  80

Lys Leu Asn Val Thr Glu Gln Glu Lys Ile Asp Lys Leu Met Ile Glu
                85                  90                  95

Met Asp Gly Thr Glu Asn Lys Ser Lys Phe Gly Ala Asn Ala Ile Leu
            100                 105                 110

Gly Val Ser Leu Ala Val Cys Lys Ala Gly Ala Val Glu Lys Gly Val
        115                 120                 125

Pro Leu Tyr Arg His Ile Ala Asp Leu Ala Gly Asn Ser Glu Val Ile
    130                 135                 140

Leu Pro Val Pro Ala Phe Asn Val Ile Asn Gly Gly Ser His Ala Gly
145                 150                 155                 160

Asn Lys Leu Ala Met Gln Glu Phe Met Ile Leu Pro Val Gly Ala Ala
                165                 170                 175

Asn Phe Arg Glu Ala Met Arg Ile Gly Ala Glu Val Tyr His Asn Leu
            180                 185                 190

Lys Asn Val Ile Lys Glu Lys Tyr Gly Lys Asp Ala Thr Asn Val Gly
        195                 200                 205

Asp Glu Gly Gly Phe Ala Pro Asn Ile Leu Glu Asn Lys Glu Gly Leu
    210                 215                 220

Glu Leu Leu Lys Thr Ala Ile Gly Lys Ala Gly Tyr Thr Asp Lys Val
225                 230                 235                 240

Val Ile Gly Met Asp Val Ala Ala Ser Glu Phe Phe Arg Ser Gly Lys
                245                 250                 255

Tyr Asp Leu Asp Phe Lys Ser Pro Asp Asp Pro Ser Arg Tyr Ile Ser
            260                 265                 270

Pro Asp Gln Leu Ala Asp Leu Tyr Lys Ser Phe Ile Lys Asp Tyr Pro
        275                 280                 285

Val Val Ser Ile Glu Asp Pro Phe Asp Gln Asp Asp Trp Gly Ala Trp
    290                 295                 300

Gln Lys Phe Thr Ala Ser Ala Gly Ile Gln Val Val Gly Asp Asp Leu
305                 310                 315                 320

Thr Val Thr Asn Pro Lys Arg Ile Ala Lys Ala Val Asn Glu Lys Ser
                325                 330                 335

Cys Asn Cys Leu Leu Leu Lys Val Asn Gln Ile Gly Ser Val Thr Glu
            340                 345                 350

```
Ser Leu Gln Ala Cys Lys Leu Ala Gln Ala Asn Gly Trp Gly Val Met
        355                 360                 365

Val Ser His Arg Ser Gly Glu Thr Glu Asp Thr Phe Ile Ala Asp Leu
    370                 375                 380

Val Val Gly Leu Cys Thr Gly Gln Ile Lys Thr Gly Ala Pro Cys Arg
385                 390                 395                 400

Ser Glu Arg Leu Ala Lys Tyr Asn Gln Leu Leu Arg Ile Glu Glu Glu
                405                 410                 415

Leu Gly Ser Lys Ala Lys Phe Ala Gly Arg Asn Phe Arg Asn Pro Leu
                420                 425                 430

Ala Lys

<210> SEQ ID NO 7
<211> LENGTH: 17
<212> TYPE: PRT
<213> ORGANISM: Homo sapiens
<220> FEATURE:
<221> NAME/KEY: UNSURE
<222> LOCATION: (5)..(5)
<223> OTHER INFORMATION: citrulline
<220> FEATURE:
<221> NAME/KEY: UNSURE
<222> LOCATION: (11)..(11)
<223> OTHER INFORMATION: citrulline

<400> SEQUENCE: 7

Lys Ile His Ala Xaa Glu Ile Phe Asp Ser Xaa Gly Asn Pro Thr Val
1               5                   10                  15

Glu

<210> SEQ ID NO 8
<211> LENGTH: 17
<212> TYPE: PRT
<213> ORGANISM: Homo sapiens
<220> FEATURE:
<221> NAME/KEY: UNSURE
<222> LOCATION: (11)..(11)
<223> OTHER INFORMATION: citrulline

<400> SEQUENCE: 8

Lys Ile His Ala Arg Glu Ile Phe Asp Ser Xaa Gly Asn Pro Thr Val
1               5                   10                  15

Glu

<210> SEQ ID NO 9
<211> LENGTH: 19
<212> TYPE: PRT
<213> ORGANISM: Homo sapiens
<220> FEATURE:
<221> NAME/KEY: UNSURE
<222> LOCATION: (6)..(6)
<223> OTHER INFORMATION: citrulline
<220> FEATURE:
<221> NAME/KEY: UNSURE
<222> LOCATION: (12)..(12)
<223> OTHER INFORMATION: citrulline

<400> SEQUENCE: 9

Cys Lys Ile His Ala Xaa Glu Ile Phe Asp Ser Xaa Gly Asn Pro Thr
1               5                   10                  15

Val Glu Cys
```

-continued

```
<210> SEQ ID NO 10
<211> LENGTH: 19
<212> TYPE: PRT
<213> ORGANISM: Homo sapiens
<220> FEATURE:
<221> NAME/KEY: UNSURE
<222> LOCATION: (12)..(12)
<223> OTHER INFORMATION: citrulline

<400> SEQUENCE: 10

Cys Lys Ile His Ala Arg Glu Ile Phe Asp Ser Xaa Gly Asn Pro Thr
1               5                   10                  15

Val Glu Cys

<210> SEQ ID NO 11
<211> LENGTH: 19
<212> TYPE: PRT
<213> ORGANISM: Homo sapiens
<220> FEATURE:
<221> NAME/KEY: UNSURE
<222> LOCATION: (6)..(6)
<223> OTHER INFORMATION: citrulline

<400> SEQUENCE: 11

Cys Lys Ile His Ala Xaa Glu Ile Phe Asp Ser Arg Gly Asn Pro Thr
1               5                   10                  15

Val Glu Cys

<210> SEQ ID NO 12
<211> LENGTH: 19
<212> TYPE: PRT
<213> ORGANISM: Homo sapiens

<400> SEQUENCE: 12

Cys Lys Ile His Ala Arg Glu Ile Phe Asp Ser Arg Gly Asn Pro Thr
1               5                   10                  15

Val Glu Cys

<210> SEQ ID NO 13
<211> LENGTH: 17
<212> TYPE: PRT
<213> ORGANISM: Homo sapiens
<220> FEATURE:
<221> NAME/KEY: UNSURE
<222> LOCATION: (5)..(5)
<223> OTHER INFORMATION: citrulline

<400> SEQUENCE: 13

Lys Ile His Ala Xaa Glu Ile Phe Asp Ser Arg Gly Asn Pro Thr Val
1               5                   10                  15

Glu

<210> SEQ ID NO 14
<211> LENGTH: 17
<212> TYPE: PRT
<213> ORGANISM: Homo sapiens

<400> SEQUENCE: 14

Lys Ile His Ala Arg Glu Ile Phe Asp Ser Arg Gly Asn Pro Thr Val
1               5                   10                  15

Glu
```

```
<210> SEQ ID NO 15
<211> LENGTH: 24
<212> TYPE: PRT
<213> ORGANISM: Homo sapiens
<220> FEATURE:
<221> NAME/KEY: UNSURE
<222> LOCATION: (4)..(4)
<223> OTHER INFORMATION: citrulline
<220> FEATURE:
<221> NAME/KEY: UNSURE
<222> LOCATION: (11)..(11)
<223> OTHER INFORMATION: citrulline

<400> SEQUENCE: 15

Ile His Ala Xaa Glu Glu Ile Phe Asp Ser Xaa Gly Asn Pro Thr Val
1               5                   10                  15

Glu Val Asp Leu Phe Thr Ser Lys
            20

<210> SEQ ID NO 16
<211> LENGTH: 19
<212> TYPE: PRT
<213> ORGANISM: Homo sapiens
<220> FEATURE:
<221> NAME/KEY: UNSURE
<222> LOCATION: (6)..(6)
<223> OTHER INFORMATION: citrulline
<220> FEATURE:
<221> NAME/KEY: UNSURE
<222> LOCATION: (12)..(12)
<223> OTHER INFORMATION: citrulline

<400> SEQUENCE: 16

Cys Lys Ile Ile Gly Xaa Glu Ile Leu Asp Ser Xaa Gly Asn Pro Thr
1               5                   10                  15

Val Glu Cys

<210> SEQ ID NO 17
<211> LENGTH: 19
<212> TYPE: PRT
<213> ORGANISM: Homo sapiens
<220> FEATURE:
<221> NAME/KEY: UNSURE
<222> LOCATION: (12)..(12)
<223> OTHER INFORMATION: citrulline

<400> SEQUENCE: 17

Cys Val Asp Leu Phe Thr Ser Lys Gly Leu Phe Xaa Ala Ala Val Pro
1               5                   10                  15

Ser Gly Cys

<210> SEQ ID NO 18
<211> LENGTH: 23
<212> TYPE: PRT
<213> ORGANISM: Homo sapiens
<220> FEATURE:
<221> NAME/KEY: UNSURE
<222> LOCATION: (8)..(8)
<223> OTHER INFORMATION: citrulline
<220> FEATURE:
<221> NAME/KEY: UNSURE
<222> LOCATION: (14)..(14)
<223> OTHER INFORMATION: citrulline
```

-continued

<400> SEQUENCE: 18

Cys Tyr Glu Ala Leu Glu Leu Xaa Asp Asn Asp Lys Thr Xaa Tyr Met
1               5                   10                  15

Gly Lys Gly Val Ser Lys Cys
            20

<210> SEQ ID NO 19
<211> LENGTH: 20
<212> TYPE: PRT
<213> ORGANISM: Homo sapiens
<220> FEATURE:
<221> NAME/KEY: UNSURE
<222> LOCATION: (9)..(9)
<223> OTHER INFORMATION: citrulline

<400> SEQUENCE: 19

Cys Glu Lys Gly Val Pro Leu Tyr Xaa His Ile Ala Asp Leu Ala Gly
1               5                   10                  15

Asn Ser Glu Cys
            20

<210> SEQ ID NO 20
<211> LENGTH: 20
<212> TYPE: PRT
<213> ORGANISM: Homo sapiens
<220> FEATURE:
<221> NAME/KEY: UNSURE
<222> LOCATION: (4)..(4)
<223> OTHER INFORMATION: citrulline
<220> FEATURE:
<221> NAME/KEY: UNSURE
<222> LOCATION: (8)..(8)
<223> OTHER INFORMATION: citrulline

<400> SEQUENCE: 20

Cys Asn Phe Xaa Glu Ala Met Xaa Ile Gly Ala Glu Val Tyr His Asn
1               5                   10                  15

Leu Lys Asn Cys
            20

<210> SEQ ID NO 21
<211> LENGTH: 21
<212> TYPE: PRT
<213> ORGANISM: Homo sapiens
<220> FEATURE:
<221> NAME/KEY: UNSURE
<222> LOCATION: (3)..(3)
<223> OTHER INFORMATION: citrulline
<220> FEATURE:
<221> NAME/KEY: UNSURE
<222> LOCATION: (19)..(19)
<223> OTHER INFORMATION: citrulline

<400> SEQUENCE: 21

Cys Phe Xaa Ser Gly Lys Tyr Asp Leu Asp Phe Lys Ser Pro Asp Asp
1               5                   10                  15

Pro Ser Xaa Tyr Cys
            20

<210> SEQ ID NO 22
<211> LENGTH: 20
<212> TYPE: PRT
<213> ORGANISM: Homo sapiens
<220> FEATURE:
<221> NAME/KEY: UNSURE
<222> LOCATION: (12)..(12)
<223> OTHER INFORMATION: citrulline

```
<400> SEQUENCE: 22

Cys Ala Asn Gly Trp Gly Val Met Val Ser His Xaa Ser Gly Glu Thr
1               5                   10                  15

Glu Asp Thr Cys
            20

<210> SEQ ID NO 23
<211> LENGTH: 19
<212> TYPE: PRT
<213> ORGANISM: Homo sapiens
<220> FEATURE:
<221> NAME/KEY: UNSURE
<222> LOCATION: (9)..(9)
<223> OTHER INFORMATION: citrulline

<400> SEQUENCE: 23

Cys Ala Lys Tyr Asn Gln Leu Leu Xaa Ile Glu Glu Glu Leu Gly Ser
1               5                   10                  15

Lys Ala Cys

<210> SEQ ID NO 24
<211> LENGTH: 15
<212> TYPE: PRT
<213> ORGANISM: Homo sapiens
<220> FEATURE:
<221> NAME/KEY: UNSURE
<222> LOCATION: (6)..(6)
<223> OTHER INFORMATION: citrulline
<220> FEATURE:
<221> NAME/KEY: UNSURE
<222> LOCATION: (9)..(9)
<223> OTHER INFORMATION: citrulline

<400> SEQUENCE: 24

Cys Lys Phe Ala Gly Xaa Asn Phe Xaa Asn Pro Leu Ala Lys Cys
1               5                   10                  15

<210> SEQ ID NO 25
<211> LENGTH: 21
<212> TYPE: PRT
<213> ORGANISM: Homo sapiens
<220> FEATURE:
<221> NAME/KEY: UNSURE
<222> LOCATION: (16)..(16)
<223> OTHER INFORMATION: citrulline

<400> SEQUENCE: 25

Cys Ile Gln Val Val Gly Asp Asp Leu Thr Val Thr Asn Pro Lys Xaa
1               5                   10                  15

Ile Ala Lys Ala Cys
            20

<210> SEQ ID NO 26
<211> LENGTH: 20
<212> TYPE: PRT
<213> ORGANISM: Homo sapiens
<220> FEATURE:
<221> NAME/KEY: UNSURE
<222> LOCATION: (5)..(5)
<223> OTHER INFORMATION: citrulline

<400> SEQUENCE: 26

Cys Asn Pro Lys Xaa Ile Ala Lys Ala Val Asn Glu Lys Ser Cys Asn
1               5                   10                  15

Cys Leu Leu Cys
            20
```

```
<210> SEQ ID NO 27
<211> LENGTH: 17
<212> TYPE: PRT
<213> ORGANISM: Streptococcus pyogenes

<400> SEQUENCE: 27

Asp Val Tyr Ala Arg Glu Val Leu Asp Ser Arg Gly Asn Pro Thr Leu
1               5                   10                  15

Glu

<210> SEQ ID NO 28
<211> LENGTH: 17
<212> TYPE: PRT
<213> ORGANISM: Porphyromonas gingivalis

<400> SEQUENCE: 28

Lys Ile Ile Gly Arg Glu Ile Leu Asp Ser Arg Gly Asn Pro Thr Val
1               5                   10                  15

Glu

<210> SEQ ID NO 29
<211> LENGTH: 5
<212> TYPE: PRT
<213> ORGANISM: Homo sapiens
<220> FEATURE:
<221> NAME/KEY: UNSURE
<222> LOCATION: (4)..(4)
<223> OTHER INFORMATION: citrulline

<400> SEQUENCE: 29

Phe Asp Ser Xaa Gly
1               5

<210> SEQ ID NO 30
<211> LENGTH: 5
<212> TYPE: PRT
<213> ORGANISM: Homo sapiens
<220> FEATURE:
<221> NAME/KEY: UNSURE
<222> LOCATION: (3)..(3)
<223> OTHER INFORMATION: citrulline

<400> SEQUENCE: 30

Asp Ser Xaa Gly Asn
1               5

<210> SEQ ID NO 31
<211> LENGTH: 5
<212> TYPE: PRT
<213> ORGANISM: Homo sapiens
<220> FEATURE:
<221> NAME/KEY: UNSURE
<222> LOCATION: (2)..(2)
<223> OTHER INFORMATION: citrulline

<400> SEQUENCE: 31

Ser Xaa Gly Asn Pro
1               5
```